United States Patent
Browning

(10) Patent No.: US 8,182,413 B2
(45) Date of Patent: May 22, 2012

(54) METHOD FOR FIBROUS ANCHORING OF A PELVIC SUPPORT

(75) Inventor: James Browning, Glasgow (GB)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/163,509

(22) Filed: Jun. 17, 2011

(65) Prior Publication Data

US 2011/0237868 A1   Sep. 29, 2011

Related U.S. Application Data

(63) Continuation of application No. 11/324,028, filed on Dec. 30, 2005, which is a continuation-in-part of application No. 10/510,488, filed as application No. PCT/GB03/01573 on Apr. 11, 2003, now abandoned.

(60) Provisional application No. 60/393,969, filed on Jul. 5, 2002.

(30) Foreign Application Priority Data

Apr. 11, 2002   (GB) .................................. 0208359.0

(51) Int. Cl.
*A61F 2/02* (2006.01)
(52) U.S. Cl. ........................................... 600/37; 600/30
(58) Field of Classification Search ............. 600/29–31, 600/37; 606/151–158
See application file for complete search history.

(56) References Cited

U.S. PATENT DOCUMENTS

| | | | |
|---|---|---|---|
| 2,738,790 A | 3/1956 | Todt, Sr. et al. | |
| 3,054,406 A | 9/1962 | Usher | |
| 3,124,136 A | 3/1964 | Usher | |
| 3,182,662 A | 5/1965 | Shirodkar | |
| 3,311,110 A | 3/1967 | Singerman et al. | |
| 3,384,073 A | 5/1968 | Van Winkle, Jr. | |
| 3,472,232 A | 10/1969 | Earl | |
| 3,580,313 A | 5/1971 | McKnight | |
| 3,763,860 A | 10/1973 | Clarke | |
| 3,789,828 A | 2/1974 | Schulte | |
| 3,858,783 A | 1/1975 | Kapitanov et al. | |
| 3,888,975 A | 6/1975 | Ramwell | |
| 3,911,911 A | 10/1975 | Scommegna | |
| 3,913,573 A | 10/1975 | Gutnick | |
| 3,916,899 A | 11/1975 | Theeuwes et al. | |
| 3,924,633 A | 12/1975 | Cook et al. | |

(Continued)

FOREIGN PATENT DOCUMENTS

DE   2305815 A1   8/1974

(Continued)

OTHER PUBLICATIONS

Narik and Palmrich, "A simplified sling operation suitable for routine use," Am. J. Obstet. Gynecol., 1962, 84:400-405.

(Continued)

*Primary Examiner* — Charles A Marmor, II
*Assistant Examiner* — Catherine E Burk
(74) *Attorney, Agent, or Firm* — Faegre Baker Daniels LLP

(57) ABSTRACT

A method for supporting a urethra of a patient includes making an incision on an upper wall of a vagina of the patient and inserting a first end of a surgical implant through the incision and on a first side of a urethra of the patient. The first end of the surgical implant has a first fixing zone with a retaining portion that is formed of a fiber entanglement and a mesh.

12 Claims, 59 Drawing Sheets

U.S. PATENT DOCUMENTS

| | | |
|---|---|---|
| 3,993,058 A | 11/1976 | Hoff |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,233,968 A | 11/1980 | Shaw, Jr. |
| 4,235,238 A | 11/1980 | Ogiu et al. |
| 4,246,660 A | 1/1981 | Wevers |
| 4,441,497 A | 4/1984 | Paudler |
| 4,444,933 A | 4/1984 | Columbus et al. |
| 4,509,516 A | 4/1985 | Richmond |
| 4,632,100 A | 12/1986 | Somers et al. |
| 4,633,873 A | 1/1987 | Dumican et al. |
| 4,646,731 A | 3/1987 | Brower |
| 4,655,221 A | 4/1987 | Devereux |
| 4,775,380 A | 10/1988 | Seedhom et al. |
| 4,857,041 A | 8/1989 | Annis et al. |
| 4,865,031 A | 9/1989 | O'Keeffe |
| 4,873,976 A | 10/1989 | Schreiber |
| 4,920,986 A | 5/1990 | Biswas |
| 4,938,760 A | 7/1990 | Burton et al. |
| 5,013,292 A | 5/1991 | Lemay |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,149,329 A | 9/1992 | Richardson |
| 5,188,636 A | 2/1993 | Fedotov |
| 5,207,694 A | 5/1993 | Broome |
| 5,209,756 A | 5/1993 | Seedhom et al. |
| 5,250,033 A | 10/1993 | Evans et al. |
| 5,256,133 A | 10/1993 | Spitz |
| 5,259,835 A | 11/1993 | Clark et al. |
| 5,281,237 A | 1/1994 | Gimpelson |
| 5,328,077 A | 7/1994 | Lou |
| 5,336,239 A | 8/1994 | Gimpelson |
| 5,337,736 A | 8/1994 | Reddy |
| 5,342,376 A | 8/1994 | Ruff |
| 5,362,294 A | 11/1994 | Seitzinger |
| 5,368,595 A | 11/1994 | Lewis |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,434,146 A | 7/1995 | Labrie et al. |
| 5,439,467 A | 8/1995 | Benderev et al. |
| 5,456,711 A | 10/1995 | Hudson |
| 5,486,197 A | 1/1996 | Le et al. |
| 5,507,754 A | 4/1996 | Green et al. |
| 5,507,796 A | 4/1996 | Hasson |
| 5,520,700 A | 5/1996 | Beyar et al. |
| 5,522,896 A | 6/1996 | Prescott |
| 5,544,664 A | 8/1996 | Benderev et al. |
| 5,549,619 A | 8/1996 | Peters et al. |
| 5,562,685 A | 10/1996 | Mollenauer et al. |
| 5,562,689 A | 10/1996 | Green et al. |
| 5,569,273 A | 10/1996 | Titone et al. |
| 5,571,139 A | 11/1996 | Jenkins, Jr. |
| 5,591,163 A | 1/1997 | Thompson |
| 5,611,515 A | 3/1997 | Benderev et al. |
| 5,628,756 A | 5/1997 | Barker, Jr. et al. |
| 5,633,286 A | 5/1997 | Chen |
| 5,645,568 A | 7/1997 | Chervitz et al. |
| 5,647,836 A | 7/1997 | Blake, III et al. |
| 5,669,935 A | 9/1997 | Rosenman et al. |
| 5,683,349 A | 11/1997 | Makower et al. |
| 5,695,525 A | 12/1997 | Mulhauser et al. |
| 5,697,931 A | 12/1997 | Thompson |
| 5,697,978 A | 12/1997 | Sgro |
| 5,720,766 A | 2/1998 | Zang et al. |
| 5,749,884 A | 5/1998 | Benderev et al. |
| 5,766,221 A | 6/1998 | Benderev et al. |
| 5,807,403 A | 9/1998 | Beyar et al. |
| 5,816,258 A | 10/1998 | Jervis |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,851,229 A | 12/1998 | Lentz et al. |
| 5,860,425 A | 1/1999 | Benderev et al. |
| 5,899,909 A | 5/1999 | Claren et al. |
| 5,904,692 A | 5/1999 | Steckel et al. |
| 5,919,232 A | 7/1999 | Chaffringeon et al. |
| 5,922,026 A | 7/1999 | Chin |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Beyar et al. |
| 5,988,171 A | 11/1999 | Sohn et al. |
| 5,997,554 A | 12/1999 | Thompson |
| 6,010,447 A | 1/2000 | Kardjian |
| 6,030,393 A | 2/2000 | Corlew |
| 6,031,148 A | 2/2000 | Hayes et al. |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,306 A | 4/2000 | Spielberg |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,090,116 A | 7/2000 | D'Aversa et al. |
| 6,106,545 A | 8/2000 | Egan |
| 6,110,101 A | 8/2000 | Tihon et al. |
| 6,117,067 A | 9/2000 | Gil-Vernet |
| 6,159,207 A | 12/2000 | Yoon |
| 6,162,962 A | 12/2000 | Hinsch et al. |
| 6,168,611 B1 | 1/2001 | Rizvi |
| 6,190,401 B1 | 2/2001 | Green et al. |
| 6,197,036 B1 | 3/2001 | Tripp et al. |
| 6,200,330 B1 | 3/2001 | Benderev et al. |
| 6,221,005 B1 | 4/2001 | Bruckner et al. |
| 6,231,496 B1 | 5/2001 | Wilk et al. |
| 6,245,082 B1 | 6/2001 | Gellman et al. |
| 6,264,676 B1 | 7/2001 | Gellman et al. |
| 6,267,772 B1 | 7/2001 | Mulhauser et al. |
| 6,273,852 B1 | 8/2001 | Lehe et al. |
| 6,287,316 B1 | 9/2001 | Agarwal et al. |
| 6,292,700 B1 | 9/2001 | Morrison et al. |
| 6,302,840 B1 | 10/2001 | Benderev |
| 6,306,079 B1 | 10/2001 | Trabucco |
| 6,319,264 B1 * | 11/2001 | Tormala et al. ............... 606/151 |
| 6,328,686 B1 | 12/2001 | Kovac |
| 6,328,744 B1 | 12/2001 | Harari et al. |
| 6,334,446 B1 | 1/2002 | Beyar |
| 6,352,553 B1 | 3/2002 | van der Burg et al. |
| 6,355,065 B1 | 3/2002 | Gabbay |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,408,656 B1 | 6/2002 | Ory et al. |
| 6,418,930 B1 | 7/2002 | Fowler |
| 6,443,964 B1 | 9/2002 | Ory et al. |
| 6,475,139 B1 | 11/2002 | Miller |
| 6,478,727 B2 | 11/2002 | Scetbon |
| 6,478,791 B1 | 11/2002 | Carter et al. |
| 6,482,214 B1 | 11/2002 | Sidor, Jr. et al. |
| 6,491,703 B1 | 12/2002 | Ulmsten |
| 6,494,887 B1 | 12/2002 | Kaladelfos |
| 6,494,906 B1 | 12/2002 | Owens |
| 6,502,578 B2 | 1/2003 | Raz et al. |
| 6,506,190 B1 | 1/2003 | Walshe |
| 6,527,802 B1 | 3/2003 | Mayer |
| 6,530,943 B1 | 3/2003 | Hoepffner et al. |
| 6,544,273 B1 | 4/2003 | Harari et al. |
| 6,575,897 B1 | 6/2003 | Ory et al. |
| 6,575,998 B2 | 6/2003 | Beyar |
| 6,582,443 B2 | 6/2003 | Cabak et al. |
| 6,592,515 B2 | 7/2003 | Thierfelder et al. |

| | | |
|---|---|---|
| 6,596,001 B2 | 7/2003 | Stormby et al. |
| 6,599,235 B2 | 7/2003 | Kovac |
| 6,599,318 B1 | 7/2003 | Gabbay |
| 6,599,323 B2 | 7/2003 | Melican et al. |
| 6,612,977 B2 | 9/2003 | Staskin et al. |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,652,450 B2 | 11/2003 | Neisz et al. |
| 6,652,595 B1 | 11/2003 | Nicolo |
| 6,666,817 B2 | 12/2003 | Li |
| 6,669,706 B2 | 12/2003 | Schmitt et al. |
| 6,669,735 B1 | 12/2003 | Pelissier |
| 6,673,010 B2 | 1/2004 | Skiba et al. |
| 6,679,896 B2 | 1/2004 | Gellman et al. |
| 6,689,047 B2 | 2/2004 | Gellman |
| 6,691,711 B2 | 2/2004 | Raz et al. |
| 6,695,855 B1 | 2/2004 | Gaston |
| 6,702,827 B1 | 3/2004 | Lund et al. |
| 6,737,371 B1 | 5/2004 | Planck et al. |
| 6,755,781 B2 | 6/2004 | Gellman |
| 6,786,861 B1 | 9/2004 | Pretorius |
| 6,830,052 B2 | 12/2004 | Carter et al. |
| 6,884,212 B2 | 4/2005 | Thierfelder et al. |
| 6,911,003 B2 | 6/2005 | Anderson et al. |
| 6,932,759 B2 | 8/2005 | Kammerer et al. |
| 6,936,052 B2 | 8/2005 | Gellman et al. |
| 6,960,160 B2 | 11/2005 | Browning |
| 7,025,063 B2 | 4/2006 | Snitkin et al. |
| 7,070,556 B2 | 7/2006 | Anderson et al. |
| 7,070,558 B2 | 7/2006 | Gellman et al. |
| 7,094,199 B2 | 8/2006 | Petros et al. |
| 7,112,171 B2 | 9/2006 | Rocheleau et al. |
| 7,112,210 B2 * | 9/2006 | Ulmsten et al. ................ 606/151 |
| 7,140,956 B1 | 11/2006 | Korovin et al. |
| 7,156,858 B2 | 1/2007 | Schuldt-Hempe et al. |
| 7,204,802 B2 | 4/2007 | De Leval |
| 7,229,404 B2 | 6/2007 | Bouffier |
| 7,288,063 B2 | 10/2007 | Petros et al. |
| 7,290,410 B2 | 11/2007 | Meneghin et al. |
| 7,297,102 B2 | 11/2007 | Smith et al. |
| 7,326,213 B2 | 2/2008 | Benderev et al. |
| 7,347,812 B2 | 3/2008 | Mellier |
| 7,387,634 B2 | 6/2008 | Benderev |
| 7,395,822 B1 | 7/2008 | Burton et al. |
| 7,410,460 B2 | 8/2008 | Benderev |
| 7,500,945 B2 | 3/2009 | Cox et al. |
| 7,517,313 B2 | 4/2009 | Thierfelder et al. |
| 7,527,633 B2 | 5/2009 | Rioux |
| 7,559,885 B2 | 7/2009 | Merade et al. |
| 7,594,921 B2 | 9/2009 | Browning |
| 7,601,118 B2 | 10/2009 | Smith et al. |
| 7,611,454 B2 | 11/2009 | De Leval |
| 7,614,258 B2 | 11/2009 | Cherok et al. |
| 7,621,864 B2 | 11/2009 | Suslian et al. |
| 7,628,156 B2 | 12/2009 | Astani et al. |
| 7,673,631 B2 | 3/2010 | Astani et al. |
| 7,686,760 B2 | 3/2010 | Anderson et al. |
| 7,722,528 B2 | 5/2010 | Arnal et al. |
| 7,740,576 B2 | 6/2010 | Hodroff et al. |
| 7,789,821 B2 | 9/2010 | Browning |
| 7,815,662 B2 | 10/2010 | Spivey et al. |
| 7,927,342 B2 | 4/2011 | Rioux |
| 7,975,698 B2 | 7/2011 | Browning |
| 7,981,022 B2 | 7/2011 | Gellman et al. |
| 8,007,430 B2 | 8/2011 | Browning |
| 8,016,741 B2 | 9/2011 | Weiser et al. |
| 8,016,743 B2 | 9/2011 | Romero Maroto |
| 8,047,983 B2 | 11/2011 | Browning |
| 2001/0000533 A1 | 4/2001 | Kovac |
| 2001/0018549 A1 | 8/2001 | Scetbon |
| 2001/0039423 A1 | 11/2001 | Skiba et al. |
| 2001/0049467 A1 | 12/2001 | Lehe et al. |
| 2001/0049538 A1 | 12/2001 | Trabucco |
| 2001/0051815 A1 | 12/2001 | Esplin |
| 2001/0053916 A1 | 12/2001 | Rioux |
| 2002/0005204 A1 | 1/2002 | Benderev et al. |
| 2002/0007222 A1 | 1/2002 | Desai |
| 2002/0022841 A1 | 2/2002 | Kovac |
| 2002/0028980 A1 | 3/2002 | Thierfelder et al. |
| 2002/0042658 A1 | 4/2002 | Tyagi |
| 2002/0049503 A1 | 4/2002 | Milbocker |
| 2002/0052612 A1 | 5/2002 | Schmitt et al. |
| 2002/0052654 A1 | 5/2002 | Darois et al. |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |
| 2002/0078964 A1 | 6/2002 | Kovac et al. |
| 2002/0082619 A1 | 6/2002 | Cabak et al. |
| 2002/0083949 A1 | 7/2002 | James |
| 2002/0091298 A1 | 7/2002 | Landgrebe |
| 2002/0091373 A1 | 7/2002 | Berger |
| 2002/0099258 A1 * | 7/2002 | Staskin et al. ................ 600/29 |
| 2002/0099259 A1 | 7/2002 | Anderson et al. |
| 2002/0099260 A1 | 7/2002 | Suslian et al. |
| 2002/0103542 A1 | 8/2002 | Bilbo |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0119177 A1 | 8/2002 | Bowman et al. |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 * | 10/2002 | Neisz et al. ................ 606/151 |
| 2002/0183588 A1 | 12/2002 | Fierro |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz et al. |
| 2003/0023137 A1 | 1/2003 | Gellman |
| 2003/0023138 A1 | 1/2003 | Luscombe |
| 2003/0036676 A1 | 2/2003 | Scetbon |
| 2003/0050530 A1 | 3/2003 | Neisz et al. |
| 2003/0065246 A1 | 4/2003 | Inman et al. |
| 2003/0065402 A1 | 4/2003 | Anderson et al. |
| 2003/0078468 A1 | 4/2003 | Skiba et al. |
| 2003/0100954 A1 | 5/2003 | Schuldt-Hempe et al. |
| 2003/0130670 A1 | 7/2003 | Anderson et al. |
| 2003/0149440 A1 | 8/2003 | Kammerer et al. |
| 2003/0171644 A1 | 9/2003 | Anderson et al. |
| 2003/0176875 A1 | 9/2003 | Anderson et al. |
| 2003/0191360 A1 | 10/2003 | Browning |
| 2003/0199732 A1 | 10/2003 | Suslian et al. |
| 2003/0212305 A1 | 11/2003 | Anderson et al. |
| 2003/0220538 A1 | 11/2003 | Jacquetin |
| 2004/0029478 A1 | 2/2004 | Planck et al. |
| 2004/0034373 A1 | 2/2004 | Schuldt-Hempe et al. |
| 2004/0039453 A1 | 2/2004 | Anderson et al. |
| 2004/0097974 A1 | 5/2004 | De Leval |
| 2004/0144395 A1 | 7/2004 | Evans et al. |
| 2004/0172048 A1 | 9/2004 | Browning |
| 2004/0231678 A1 | 11/2004 | Fierro |
| 2004/0243166 A1 | 12/2004 | Odermatt et al. |
| 2004/0249240 A1 | 12/2004 | Goldmann et al. |
| 2004/0249373 A1 | 12/2004 | Gronemeyer et al. |
| 2004/0249397 A1 | 12/2004 | Delorme et al. |
| 2004/0249473 A1 | 12/2004 | Delorme et al. |
| 2005/0000524 A1 | 1/2005 | Cancel et al. |
| 2005/0004576 A1 | 1/2005 | Benderev |
| 2005/0080317 A1 | 4/2005 | Merade |
| 2005/0107805 A1 | 5/2005 | Bouffier et al. |
| 2005/0240076 A1 | 10/2005 | Neisz et al. |
| 2005/0277806 A1 | 12/2005 | Cristalli |
| 2005/0278037 A1 | 12/2005 | Delorme et al. |
| 2006/0025649 A1 | 2/2006 | Smith et al. |
| 2006/0025783 A1 | 2/2006 | Smith et al. |
| 2006/0041185 A1 | 2/2006 | Browning |
| 2006/0058578 A1 | 3/2006 | Browning |
| 2006/0089524 A1 | 4/2006 | Chu |
| 2006/0089525 A1 | 4/2006 | Mamo et al. |

| | | | | | | |
|---|---|---|---|---|---|---|
| 2006/0130848 A1 | 6/2006 | Carey | | FR | 2811218 E | 11/2000 |
| 2006/0205995 A1 | 9/2006 | Browning | | FR | 2787990 A1 | 4/2001 |
| 2006/0264698 A1 | 11/2006 | Kondonis et al. | | GB | 0378288 A | 8/1932 |
| 2007/0015953 A1 | 1/2007 | MacLean | | RU | 2187251 C1 | 8/2002 |
| 2007/0020311 A1 | 1/2007 | Browning | | RU | 2196518 C2 | 1/2003 |
| 2007/0032695 A1 | 2/2007 | Weiser | | SU | 1225547 A1 | 4/1986 |
| 2007/0032881 A1 | 2/2007 | Browning | | SU | 1342486 A1 | 10/1987 |
| 2007/0059199 A1 | 3/2007 | Labuschagne | | SU | 1475607 A1 | 4/1989 |
| 2007/0149555 A1 | 6/2007 | Kase et al. | | WO | WO9100714 A1 | 1/1991 |
| 2007/0219606 A1 | 9/2007 | Moreci et al. | | WO | WO9317635 A1 | 9/1993 |
| 2008/0021263 A1 | 1/2008 | Escude et al. | | WO | WO9319678 A2 | 10/1993 |
| 2008/0161837 A1 | 7/2008 | Toso et al. | | WO | WO9533454 A1 | 12/1995 |
| 2008/0167518 A1 | 7/2008 | Burton et al. | | WO | WO9603091 A1 | 2/1996 |
| 2008/0196729 A1 | 8/2008 | Browning | | WO | WO9606567 A1 | 3/1996 |
| 2008/0200751 A1 | 8/2008 | Browning | | WO | WO9713465 A1 | 4/1997 |
| 2009/0123522 A1 | 5/2009 | Browning | | WO | WO9722310 A2 | 6/1997 |
| 2009/0137862 A1 | 5/2009 | Evans et al. | | WO | WO9743982 A1 | 11/1997 |
| 2009/0171377 A1 | 7/2009 | Intoccia et al. | | WO | WO9819606 A1 | 5/1998 |
| 2009/0221868 A1 | 9/2009 | Evans | | WO | WO9835606 A2 | 8/1998 |
| 2009/0287229 A1 | 11/2009 | Ogdahl | | WO | WO9835616 A1 | 8/1998 |
| 2010/0022822 A1 | 1/2010 | Walshe | | WO | WO9835632 A1 | 8/1998 |
| 2010/0056856 A1 | 3/2010 | Suslian et al. | | WO | WO9857590 A1 | 12/1998 |
| 2010/0113869 A1 | 5/2010 | Goldman | | WO | WO9916381 A1 | 4/1999 |
| 2010/0130814 A1 | 5/2010 | Dubernard | | WO | WO9952450 A1 | 10/1999 |
| 2010/0198002 A1 | 8/2010 | O'Donnell | | WO | WO9959477 A1 | 11/1999 |
| 2010/0222794 A1 | 9/2010 | Browning | | WO | WO0007520 A1 | 2/2000 |
| 2010/0256442 A1 | 10/2010 | Ogdahl et al. | | WO | WO0013601 A1 | 3/2000 |
| 2010/0274074 A1 | 10/2010 | Khamis et al. | | WO | WO0015141 A1 | 3/2000 |
| 2010/0280308 A1 | 11/2010 | Browning | | WO | WO0018319 A1 | 4/2000 |
| 2010/0298630 A1 | 11/2010 | Wignall | | WO | WO0038784 A1 | 7/2000 |
| 2011/0021868 A1 | 1/2011 | Browning | | WO | WO0057812 A1 | 10/2000 |
| 2011/0034759 A1 | 2/2011 | Ogdahl et al. | | WO | WO0064370 A1 | 11/2000 |
| 2011/0105833 A1 | 5/2011 | Gozzi et al. | | WO | WO0074594 A1 | 12/2000 |
| 2011/0124954 A1 | 5/2011 | Ogdahl et al. | | WO | WO0074613 A1 | 12/2000 |
| 2011/0124956 A1 | 5/2011 | Mujwid et al. | | WO | WO0074633 A2 | 12/2000 |
| 2011/0201872 A1 | 8/2011 | Browning | | WO | WO0106951 A1 | 2/2001 |
| 2011/0230705 A1 | 9/2011 | Browning | | WO | WO0126581 A1 | 4/2001 |
| 2011/0230708 A1 | 9/2011 | Browning | | WO | WO0139670 A1 | 6/2001 |
| 2011/0230709 A1 | 9/2011 | Browning | | WO | WO0145589 A1 | 6/2001 |
| 2011/0237865 A1 | 9/2011 | Browning | | WO | WO0152729 A2 | 7/2001 |
| 2011/0237866 A1 | 9/2011 | Browning | | WO | WO0156499 A1 | 8/2001 |
| 2011/0237867 A1 | 9/2011 | Browning | | WO | WO0180773 A1 | 11/2001 |
| 2011/0237869 A1 | 9/2011 | Browning | | WO | WO0202031 A1 | 1/2002 |
| 2011/0237870 A1 | 9/2011 | Browning | | WO | WO0226108 A2 | 4/2002 |
| 2011/0237873 A1 | 9/2011 | Browning | | WO | WO0228312 A1 | 4/2002 |
| 2011/0237874 A1 | 9/2011 | Browning | | WO | WO0230293 A1 | 4/2002 |
| 2011/0237875 A1 | 9/2011 | Browning | | WO | WO0232284 A2 | 4/2002 |
| 2011/0237876 A1 | 9/2011 | Browning | | WO | WO0232346 A1 | 4/2002 |
| 2011/0237877 A1 | 9/2011 | Browning | | WO | WO0234124 A2 | 5/2002 |
| 2011/0237878 A1 | 9/2011 | Browning | | WO | WO0239890 A2 | 5/2002 |
| 2011/0237879 A1 | 9/2011 | Browning | | WO | WO02060371 A1 | 8/2002 |
| 2011/0238095 A1 | 9/2011 | Browning | | WO | WO02065921 A1 | 8/2002 |
| 2011/0245594 A1 | 10/2011 | Browning | | WO | WO02065944 A1 | 8/2002 |
| FOREIGN PATENT DOCUMENTS | | | | WO | WO02069781 A2 | 9/2002 |
| DE | 4220283 A1 | 12/1993 | | WO | WO02071953 A2 | 9/2002 |
| DE | 4304353 A1 | 4/1994 | | WO | WO02078552 A1 | 10/2002 |
| DE | 10019604 C2 | 6/2002 | | WO | WO02078568 A1 | 10/2002 |
| EP | 0009072 A1 | 4/1980 | | WO | WO02078571 A2 | 10/2002 |
| EP | 0024781 B1 | 8/1984 | | WO | WO02098340 A1 | 12/2002 |
| EP | 0024780 B1 | 10/1984 | | WO | WO03002027 A1 | 1/2003 |
| EP | 0248544 B1 | 4/1991 | | WO | WO03013392 A1 | 2/2003 |
| EP | 0139286 B1 | 8/1991 | | WO | WO03057074 A2 | 7/2003 |
| EP | 0470308 A1 | 2/1992 | | WO | WO03022260 B1 | 10/2003 |
| EP | 0557964 A1 | 9/1993 | | WO | WO03086205 A2 | 10/2003 |
| EP | 0632999 A1 | 1/1995 | | WO | WO03092546 A2 | 11/2003 |
| EP | 0650703 A1 | 5/1995 | | WO | WO03094781 A1 | 11/2003 |
| EP | 0706778 A1 | 4/1996 | | WO | WO2004002370 A1 | 1/2004 |
| EP | 1093758 A1 | 4/2001 | | WO | WO2004002379 A1 | 1/2004 |
| EP | 0719527 B1 | 8/2001 | | WO | WO2004004600 A1 | 1/2004 |
| EP | 0643945 B1 | 3/2002 | | WO | WO2004012626 A1 | 2/2004 |
| EP | 1060714 B1 | 8/2006 | | WO | WO2004098461 A2 | 11/2004 |
| EP | 1274370 B1 | 9/2006 | | WO | WO2005018494 A1 | 3/2005 |
| EP | 1296614 B1 | 9/2006 | | WO | WO2005112842 A1 | 12/2005 |
| EP | 0797962 B2 | 9/2009 | | WO | WO2006015031 A2 | 2/2006 |
| FR | 1274370 A | 10/1961 | | WO | WO2006015042 A1 | 2/2006 |
| FR | 2712177 A1 | 5/1995 | | WO | WO2006136625 A1 | 12/2006 |
| FR | 2732582 A1 | 10/1997 | | WO | WO2007059199 A2 | 5/2007 |
| FR | 2735015 A1 | 2/1998 | | | | |

| | | |
|---|---|---|
| WO | WO2007149555 A2 | 12/2007 |
| WO | WO2008007086 A2 | 1/2008 |
| WO | WO2008018494 A1 | 2/2008 |

OTHER PUBLICATIONS

Nichols, "The Mersilene Mesh Gauze-Hammock For Severe Urinary Stress Incontinence," Obstet. Gynecol., 1973, 41 (1):88-93.
Nicita, Giulio, (1998), "A New Operation for Genitourinary Prolapse," The Journal of Urology, 160:741-745.
Nickel et al., "Evaluation of a Transpelvic Sling Procedure With and Without Colpolsuspension for Treatment of Female Dogs With Refractory Urethral Sphincter Mechanism Incompetence," Veterinary Surgery, 1998, 27:94-104.
Norris et al., "Use of Synthetic Material in Sling Surgery: A Minimally Invasive Approach," J. Endocrinology, 1996, 10 (3):227-230.
Novak, "Abdonomovaginal Techniques," Gynecological Surgical Technique, 1977, Piccin Editore, Padua, 5 pages.
O'Donnell, "Combined Raz Urethral Suspension and McGuire Pubovaginal Sling for Treatment of Complicated Stress Urinary Incontinence," J. Arkansas Medical Society, 1992, 88(8):389.
Parra and Shaker, "Experience with a Simplified Technique for the Treatment of Female Stress Urinary Incontinence," British Journal of Urology, 1990, 66:615-617.
Pelosi II and Pelosi III, "New transobturator sling reduces risk of injury," OBG Management, 2003, pp. 17-37.
Pelosi III and Pelosi, "Pubic Bone Suburethral Stabilization Sling: Laparoscopic Assessment of a Transvaginal Operation for the Treatment of Stress Urinary Incontinence," Journal of Laparoendoscopic & Advanced Surgical Techniques, 1999, 9(1):45-50.
Penson and Raz, "Why Anti-incontinence Surgery Succeeds or Fails," Female Urology, 1996, Raz (ed.), W.B. Saunders Company, Chapter 41, pp. 435-442.
Pereyra et al., "Pubourethral Supports in Perspective: Modified Pereyra Procedure for Urinary Incontinence," Obstet Gynecol., 1982, 59:643-648.
Petros and Konsky, "Anchoring the midurethra restores bladder-neck anatomy and continence," The Lancet, 1999, 354:997-998.
Petros and Ulmsten, "An analysis of rapid pad testing and the history for the diagnosis of stress incontinence," Acta Obstet. Gynecol. Scand., 1992, 71:529-536.
Petros and Ulmsten, "An Anatomical Basis for Success and Failure of Female Incontinence Surgery," Scand. J. Urol. Nephrol., 1993, (Suppl. 3):55-60.
Petros and Ulmsten, "An Integral Theory and Its Method for the Diagnosis and Management of Female Urinary Incontinence," 153 Scand. J. Urol. Nephrol. 1, 64 (1993).
Petros and Ulmsten, "An Integral Theory of Female Urinary Incontinence," Acta Obstet. Gynecol. Scand., 1990, 69 (Suppl.153):7-31.
Petros and Ulmsten, "Bladder Instability in Women: A Premature Activation of the Micturition Reflex," Neurourology and Urodynamics, 1993, 12:235-239.
Petros and Ulmsten, "Cough Transmission Ratio: An Indicator of Suburethral Vaginal Wall Tension Rather than Urethral Closure?" Acta Obstet. Gynecol. Scand., 1990, 69(Suppl. 153):37-38.
Petros and Ulmsten, "Cure of Stress Incontinence by Repair of External Anal Sphincter," Acta. Obstet. Gynecol Scand., 1990, 69(Suppl. 153):75.
Petros and Ulmsten, "Cure of Urge Incontinence by the Combined Intravaginal Sling and Tuck Operation," Acta Obstet. Gynecol. Scand., 1990, 69(Suppl. 153)61-62.
Petros and Ulmsten, "Further Development of the Intravaginal Slingplasty Procedure—IVS III—(with midline "tuck")," Scand. J. Urol. Nephrol., 1993, Suppl. 153:69-71.
Petros and Ulmsten, "Non Stress Non Urge Female Urinary Incontinence—Diagnosis and Cure: A Preliminary Report," Acta Obstet. Gynecol. Scand., 1990, 69(Suppl. 153):69-70.
Petros and Ulmsten, "Part I: Theoretical, Morphological, Radiographical Correlations and Clinical Perspective," Scand. J. Urol. Nephrol., 1993, Suppl. 153:5-28.
Petros and Ulmsten, "Part II:The Biomechanics of Vaginal Tissue and supporting Ligaments with Special Relevance to the Pathogenesis of Female Urinary Incontinence," Scand. J. Urol. Nephrol., 1993, Suppl. 153:29-40.

Petros and Ulmsten, "Part III: Surgical Principles Deriving from the Theory," Scand. J. Urol. Nephrol., 1993, Suppl. 153:41-52.
Petros and Ulmsten, "Part IV: Surgical Applications of the Theory—Development of the Intravaginal Sling Plasty (IVS) Procedure," Scand. J. Urol. Nephrol., 1993, Suppl. 153:53-54.
Petros and Ulmsten, "Pinch Test for Diagnosis of Stress Urinary Incontinence," Acta Obstet. Gynecol. Scand., 1990, 69(Suppl. 153):33-35.
Petros and Ulmsten, "Pregnancy Effects on the Intravaginal Sling Operation," Acta Obstet. Gynecol. Scand., 1990, 69 (Suppl.153):77-78.
Petros and Ulmsten, "The Combined Intravaginal Sling and Tuck Operation. An Ambulatory Procedure for Cure of Stress and Urge Incontinence," Acta Obstet. Gynecol. Scand., 1990, 69(Suppl. 153):53-59.
Petros and Ulmsten, "The Development of the Intravaginal Slingplasty Procedure: IVS II—(with bilateral "tucks")," Scand. J. Urol. Nephrol., 1993, Suppl. 153:61-67.
Petros and Ulmsten, "The Free Graft Procedure for Cure of the Tethered Vagina Syndrome," Scand. J. Urol. Nephrol., 1993, Suppl. 153:85-87.
Petros and Ulmsten, "The Further Development of the Intravaginal Slingplasty Procedure: IVS IV—(with "double-breasted" unattached vaginal flap repair and "free" vaginal tapes)," Scand. J. Urol. Nephrol., 1993, Suppl. 153:73-79.
Petros and Ulmsten, "The Intravaginal Slingplasty Procedure: IVS VI—further development of the "double-breasted" vaginal flap repair—attached flap," Scand. J. Urol. Nephrol., 1993, Suppl. 153:81-84.
Petros and Ulmsten, "The Posterior Fornix Syndrome: A Multiple Symptom Complex of Pelvin Pain and Abnormal Urinary Symptoms Deriving from Laxity in the Posterior Fornix of Vagina," Scand. J. Urol. Nephrol., 1993, Suppl. 153:89-93.
Petros and Ulmsten, "The Role of a Lax Posterior Vaginal Fornix in the Causation of Stress and Urgency Symptoms: a Preliminary Report," Acta Obstet. Gynecol. Scand., 1990, 69(Suppl. 153):71-73.
Petros and Ulmsten, "The Tethered Vagina Syndrome, Post Surgical Incontinence and I-Plasty Operation for Cure," Acta Obstet. Gynecol Scand., 1990, 69(Suppl.153):63-67.
Petros and Ulmsten, "The Tuck Procedure: A Simplified Vaginal Repair for Treatment of Female Urinary Incontinence," Acta Obstet. Gynecol. Scand., 1990, 69(Suppl.153):41-42.
Petros and Ulmsten, "Urethral Pressure Increase on Effort Originates From Within the Urethra, and Continence From Musculovaginal Closure," Neurourology and Urodynamics, 1995, 14:337-350.
Petros et al., "The Autogenic Ligament Procedure: A Technique for Planned Formation of an Artificial Neo-Ligament," Acta Obstet. Gynecol. Scand., 1990, 69(Suppl. 153):43-51.
Petros, "Development of Generic Models for Ambulatory Vaginal Surgery—a Preliminary Report," Int. Urogynecol. J., 1998, 9:19-27.
Rackley et al., "Tension-free Vaginal Tape and Percutaneous Vaginal Tape Sling Procedures," Techniques in Urology, 2001, 7(2):90-100.
Rackley, "Synthetic slings: Five steps for successful placement—Follow these steps to insert Transvaginal/ Percutaneous slings using vaginal approach alone," Urology Times, 2000, 28:46-49.
Raz et al., "Urological Neurology and Urodynamics," J. Urol., 1992, 148:845-850.
Raz, "Modified Bladder Neck Suspension for Female Stress Incontinence," Urology, 1981, 17(1):82-85.
Richardson et al., "Delayed Reaction to the Dacron Buttress Used in Urethropexy," J. Reproductive Med., 1984, 29 (9):689-692.
Ridley, "Appraisal of the Goebell-Frangenheim-Stoeckel sling procedure," Am. J. Obstet. Gynecol., 1966, 95 (5):714-721.
Schumpelick, V. et at., "Minimized polypropylene mesh for preperitoneal net plasty (PNP) of incisional hernias," Chirurg 70:422-430 (1999).
Holschneider et al., "The Modified Pereyra Procedure in Recurrent Stress Urinary Incontinence: A 15-Year Review," Obstet. Gynecol., 1994, 83:573-578.
Horbach et al., "A Suburethral Sling Procedure with Polytetrafluoroethylene for the Treatment of Genuine Stress Incontinence in Patients with Low Urethral Closure Pressure," Obstet. Gynecol., 1988, 71:648-652.

Horbach, "Suburethral Sling Procedures," Urogynecology and Urodynamics—Theory and Practice, 1996, Williams & Wilkins, pp. 569-579.

Ingelnnan-Sundberg and Ulmsten, "Surgical Treatment of Female Urinary Stress Incontinence," Contr. Gynec. Obstet., 1983, 10:51-69.

International Search Report issued in PCT/GB2007/002589, mailed Jan. 22, 2008, 5 pages.

Jacquetin. Utilisation du "TVT" dans la chirurgie . . . J. Gynecol. Obstet. Biol. Reprod. 29: 242-47 (2000).

Jeffcoate, "The Results of the Aldridge Sling Operation for Stress Incontinence," The Journal of Obstetrics and Gynaecology of the British Empire, 1956, 63:36-39.

Jeter, "The Social Impact of Urinary Incontinence," Female Urology, Raz (ed.), W. B. Saunders Company, 1996, Chapter 7, pp. 80-86.

Karram and Bhatia, "Patch Procedure: Modified Transvaginal Fascia Lata Sling For Recurrent or Severe Stress Urinary Incontinence," Obstet Gynecol., 1990, 75:461-463.

Kerdiles et al., "Bypass via the Obturator Foramen in Reconstructive Arterial Surgery of the Lower Extremities," Ann. Chir. Thorac. Cardio-Vasc., 1974, 13(4):335-341.

Kerr and Staskin, "The Use of Artificial Material for Sling Surgery in the Treatment of Female Stress Urinary Incontinence," Female Urology, 1996, Raz (ed.), W.B. Saunders Company, Chapter 33, pp. 382-391.

Kersey, "The gauze hammock sling operation in the treatment of stress incontinence," Br. J. Obstet. Gynecol., 1983, 90:945-949.

Klinge et al., "Functional and Morphological Evaluation of a Low-Weight, Monofilament Polypropylene Mesh for Hernia Repair," Journal of Biomedical Material Research, Jan. 24, 2002, pp. 129-137.

Klinge, U. et al., "Influence of polyglactin-coating on functional and morphological parameters of polypropylene-mesh modifications for abnormal wall repair," Biomaterials 20 (1999), pp. 613-623.

Klinge, U. et al., "Modified Mesh for Hernia Repair that is Adapted to the Physiology of the Abdominal Wall," Eur J Surg 164:951-960 (1998).

Klinge, U. et al., "Pathophysiology of the abdominal wall," Der Chirurg, (1996),67: 229-233.

Klosterhalfen, B, et al., "Functional and morphological evaluation of different polypropylene-mesh modifications for abdominal wall repair," Biomaterials 19:2235-2246 (1998).

Klosterhalfen, B. et al., "Morphological correlation of the functional mechanics of the abdominal wall after mesh implantation," Langenbecks Arch Chir 382:87-94 (1997).

Klutke et al., "The Anatomy of Stress Incontinence: Magnetic Resonance Imaging of the Female Bladder Neck and Urethra," J. Urol., 1990, 143:563-566.

Klutke et al., "Transvaginal Bladder Neck Suspension to Cooper's Ligament: A Modified Pereyra Procedure," Obstet. Gynecol., 1996, 88:294-297.

Korda et al., "Experience with Silastic Slings for Female Urinary Incontinence," Aust. NZ J. Obstet. Gynaecol., 1989, 29:150-154.

Kovac and Cruikshank, "Pubic Bone Suburethral Stabilization Sling for Recurrent Urinary Incontinence," Obstet. Gynecol., 1997, 89:624-627.

Kovac and Cruikshank, "Pubic bone suburethral stabilization sling: a long-term cure for SUI?" Contemporary OB/GYN, 1998, 43(2):51-72.

Kovac, "Follow-up of the Pubic Bone Suburethral Stabilization Sling Operation for Recurrent Urinary Incontinence (Kovac Procedure)," J. Pelvic Surgery, 1999, 5(3):156-160.

Lazarevski, M.B., Suburethral Duplication of the Vaginal Wall—An Original Operation for Urinary Stress Incontinence in Women, 6 Int'l Urogynecol. J. 73-79 (1995).

Leach et al., "Female Stress Urinary Incontinence Clinical Guidelines Panel Summary Report on Surgical Management of Female Stress Urinary Incontinence," J. Urol., 1997, 158:875-880.

Leach, "Bone Fixation Technique for Transvaginal Needle Suspension," Urology, 1988, 31(5):388-390.

Lichtenstein et al., "The Tension-Free Hernioplasty," Am. J. Surgery, 1989, 157:188-193.

Lipton, S. and Estrin, J., "A Biomechanical Study of the Aponeurotic Iguinal Hernia Repair," Journal of the American College of Surgeons, Jun. 1994, vol. 178, pp. 595-599.

Loughlin et al., "Review of an 8-Year Experience with Modifications of Endoscopic Suspension of the Bladder Neck for Female Stress Urinary Incontinence," J. Urol., 1990, 143:44-45.

Maher, Surgical Management of Anterior Vaginal Wall Prolapse: An Evidence Based Literature Review, 2006.

Mahoney and Whelan, "Use of Obturator Foramen in Iliofemoral Artery Grafting: Case Reports," Annals of Surgery, 1966, 163(2):215-220.

Marshall et al., "The Correction of Stress Incontinence by Simple Vesicourethral Suspension," J. Urol., 2002, 168:1326-1331.

McGuire and Gormley, "Abdominal Fascial Slings," Female Urology, 1996, Raz (ed.), W.B. Saunders Company, Chapter 31, pp. 369-375.

McGuire and Lytton, "Pubovaginal Sling Procedure for Stress Incontinence," J. Urol., 1978, 119:82-84.

McGuire et al., "Experience with Pubovaginal Slings for Urinary Incontinence at the University of Michigan," J. Urol., 1987, 138:525-526.

McGuire, "Abdominal Procedures for Stress Incontinence," Urologic Clinics of North America, 1985, 12(2):285-290.

McIndoe et al., "The Aldridge Sling Procedure in the Treatment of Urinary Stress Incontinence," Aust. NZ J. Obstet. Gynaecol., 1987, 27:238-239.

McKiel, Jr. et al., "Marshall-Marchetti Procedure: Modification," J. Urol., 1966, 96:737-739.

Miklos, Mini Sling Incontinence Treatment—Vagina Plastic Surgery, http://www.miklosandmoore.com/mini_sling.php, Feb. 28, 2011.

MiniArc Single-Incision Sling http://www.americanmedicalsystems.com Mar. 4, 2011.

Moir, "The Gauze-Hammock Operation," The Journal of Obstetrics and Gynaecology of the British Commonwealth, 1968, 75(1):1-9.

Monseur, J., Anatomie Chirurgicale: Les Ligaments Du Perinee Feminin, Sep. 4, 2008.

Moore et al. "Single-Center Retrospective Study of the Technique, Safety, and 12 Month Efficacy or the MiniArc™ Single Incision Sling: A New Minimally Invasive Procedure for Treatment of Female SUI" [Online] 2009, 18, pp. 175-181.

Morgan et al., "The Marlex sling operation for the treatment of recurrent stress urinary incontinence: A 16-year review," Am. J. Obstet. Gynecol., 1985, 151:224-226.

Morgan, "A sling operation, using Marlex polypropylene mesh, for treatment of recurrent stress incontinence," Am. J. Obstet. Gynecol., 1970, 106(3):369-376.

Shaw, W., "An Operation for the Treatment of Stress Incontinence," Br. Med. J. 1949:1070-1073.

Sheiner et al., "An unusual complication of obturator foramen arterial bypass," J. Cardiovasc. Surg., 1969, 10 (4):324-328.

Sirls and Leach, "Use of Fascia Lata for Pubovaginal Sling," Female Urology, 1996, Raz (ed.). W.B. Saunders Company, Chapter 32, pp. 376-381.

Sloan and Barwin, "Stress Incontinence of Urine: A Retrospective Study of the Complications and Late Results of Simple Suprapubic Suburethral Fascial Slings," J. Urol., 1973, 110:533-536.

Spencer et al., "A Comparison of Endoscopic Suspension of the Vesical Neck with Suprapubic Vesicourethropexy for Treatment of Stress Urinary Incontinence," J. Urol., 1987, 137:411-415.

Spinosa, JP et al., Transobturator surgery for female stress incontinence: a comparative anatomical study of outside-in vs. inside-out techniques, BJU Intl., 100(5), pp. 1097-1102 (Nov. 2007).

Stamey, "Endoscopic Suspension of the Vesical Neck for Urinary Incontinence in Females," Annals of Surgery, 1980, 192(4):465-471.

Stanton, "Suprapubic Approaches for Stress Incontinence in Women," J. Am. Geriatrics Soc., 1990, 38(3):348-351.

Staskin et al., "The Gore-tex sling procedure for female sphincteric incontinence: indications, technique, and results," World J. Urol., 1997, 15:295-299.

Stothers et al., "Anterior Vaginal Wall Sling," Female Urology, 1996, Raz (ed.), W.B. Saunders Company, Chapter 35, pp. 395-398.

Ulmsten and Petros, "Intravaginal Slingplasty (IVS): An Ambulatory Surgical Procedure for Treatment of Female Urinary Incontinence," Scand. J. Urol. Nephroi., 1995, 29:75-82.

Ulmsten et al., "A three-year follow up of tension free vaginal tape for surgical treatment of female stress urinary incontinence," Br. J. Obstet. Gynecol., 1999, 106:345-350.

Ulmsten et al., "An Ambulatory Surgical Procedure Under Local Anesthesia for Treatment of Female Urinary Incontinence," Int. Urogynecol. J., 1996, 7:81-86.

Ulmsten et al., "Different Biochemical Composition of Connective Tissue in Continent and Stress Incontinent Women," Acta Obstet. Gynecol. Scand., 1987, 66:455-457.

Ulmsten et al., "The unstable female urethra," Am. J. Obstet. Gynecol., 1982, 144:93-97.

Ulmsten, "Female Urinary Incontinence—A Symptom, Not a Urodynamic Disease. Some Theoretical and Practical Aspects on the Diagnosis and Treatment of Female Urinary Incontinence," Int. Urogynecol. J., 1995, 6:2-3.

Ulstem et al., "A Multicenter Study of Tension-Free Vaginal Tape (TVT) for Surgical Treatment of Stress Urinary Incontinence," Int. Urogynecol. J., 1998, 9:210-213.

U.S. Appl. No. 13/149,994, filed Jun. 1, 2011.
U.S. Appl. No. 10/106,086, filed Mar. 25, 2002.
U.S. Appl. No. 11/199,061, filed Aug. 8, 2005.
U.S. Appl. No. 60/279,794, filed Mar. 29, 2001.
U.S. Appl. No. 60/302,929, filed Jul. 3, 2001.
U.S. Appl. No. 60/307,836, filed Jul. 25, 2001.
U.S. Appl. No. 60/322,309, filed Sep. 14, 2001.
U.S. Appl. No. 60/362,806, filed Mar. 7, 2002.
U.S. Appl. No. 60/380,797, filed May 14, 2002.
U.S. Appl. No. 60/393,969, filed Jul. 5, 2002.
U.S. Appl. No. 60/402,007, filed Aug. 8, 2002.
U.S. Appl. No. 60/414,865, filed Sep. 30, 2002.

Webster and Kreder, "Voiding Dysfunction Following Cystourethropexy: Its Evaluation and Management," J. Urol., 1990, 144:670-673.

Weidemann, Small Intestinal Submucosa for Pubourethral Sling Suspension for the Treatment of Stress Incontinence: First Histopathological Results in Humans, Jul. 2004.

Winter, "Peripubic Urethropexy for Urinary Stress Incontinence In Women," Urology, 1982, 20(4):408-411.

Woodside and Borden, "Suprapubic Endoscopic Vesical Neck Suspension for the Management of Urinary Incontinence in Myelodysplastic Girls," J. Urol., 1986, 135:97-99.

Written Opioion issued in PCT/GB2007/002589, mailed Jan. 22, 2008, 5 pages.

Zacharin and Hamilton, "Pulsion Enterocele: Long-Term Results of an Abdominoperineal Technique," Obstet. Gynecol., 1980, 55(2):141-148.

Zacharin, "The suspensory mechanism of the female urethra," J. Anat., 1963, 97(3):423-427.

Abdel-fattah, Mohamed et al. Evaluation of transobturator tapes (E-TOT) study: randomised prospective single-blinded study comparing inside-out vs. outside-in transobturator tapes in management of urodynamic stress incontinence: Short term outcomes, European Journal of Obstetrics & Gynecology and Reproductive Biology (2009).

Aldridge, "Transplantation of Fascia for Relief of Urinary Stress Incontinence," Am. J. Obstet. Gynecol., 1942, 44:398-411.

Araki et al., "The Loop-Loosening Procedure for Urination Difficulties After Stamey Suspension of the Vesical Neck," J. Urol., 1990, 144:319-323.

Asmussen and Ulmsten, "Simultaneous Urethro-Cystometry with a New Technique," Scand. J. Urol. Nephrol., 1976, 10:7-11.

Beck and McCormick, "Treatment of Urinary Stress Incontinence with Anterior Colporrhaphy," Obstetrics and Gynecology, 1982, 59(3):271-274.

Benderev, "A Modified Percutaneous Outpatient Bladder Neck Suspension System," J. Urol., 1994, 152:2316-2320.

Benderev, "Anchor Fixation and Other Modifications of Endoscopic Bladder Neck Suspension," Urology, 1992, 40 (5):409-418.

Bergman and Elia, "Three surgical procedures for genuine stress incontinence: Five-year follow-up of a prospective randomized study," Am. J. Obstet. Gynecol., 1995, 173:66-71.

BioArc SP Sling Kit, www.AmericanMedicalSystems.com, 2006.

BioArc(R) SP Sling Kit: 12 Step Procedure, American Medical Systems Inc. Online Brochure 2006, 2 pages.

Blaivas and Jacobs, "Pubovaginal Fascial Sling for the Treatment of Complicated Stress Urinary Incontinence," J. Urol., 1991, 145:1214-1218.

Blaivas and Salinas, "Type III Stress Urinary Incontinence: Importance of Proper Diagnosis and Treatment," American College of Surgeons Surgical Forum, 1984, 70.sup.th Annual Clinical Congress, San Francisco, CA, vol. XXXV, pp. 473-474.

Botros, Cystocele and Rectocele Repair: More Success With Mesh? Jun. 2006.

Bryans, "Marlex gauze hammock sling operation with Cooper's ligament attachment in the management of recurrent urinary stress incontinence," Am. J. Obstet. Gynecol., 1979, 133(3):292-294.

Burch, "Urethrovaginal fixation to Cooper's ligament for correction of stress incontinence, cystocele, and prolapse," Am. J. Obstet. Gynecol., 1961, 81(2):281-290.

Certified copy of priority document for GB Application No. 0025068.8, filed Oct. 12, 2000, 38 pages.

Certified copy of priority document for GB Application No. 0208359.0, filed Apr. 11, 2002, 50 pages.

Certified copy of priority document for GB Application No. 0411360.1, filed May 21, 2004, 31 pages.

Chen, Biologic Grafts and Synthetic Meshes in Pelvic Reconstructive Surgery, Jun. 2007.

Choe and Staskin, "Gore-Tex Patch Sling: 7 Years Later," Urology, 1999, 54:641-646.

Chopra et al., "Technique of Rectangular Fascial Sling," Female Urology, 1996, Raz (ed.), W.B. Saunders Company, Chapter 34, pp. 392-394.

Dargent, D. et al., Pose d'un ruban sous uretral oblique par voie obturatrice dans le traitement de L'incontinence urinary feminine [English "Insertion of a transobturator oblique suburethral sling in the treatment of female urinary incontinence"], Gynecol. Obstet. Ferril. 14, pp. 576-582 (2002) [including English translation at the beginning of document].

Das and Palmer, "Laparoscopic Colpo-Suspension," J. Urol., 1995, 154:1119-1121.

de Leval, J., "Novel Surgical Technique for the Treatment of Female Stress Urinary Continence: Transobturator Vaginal Tape Inside-Out," European Urology, 2003, 44:724-730.

DeBord, James R., (1998), "The Historical Development of Prosthetics in Hernia Surgery," Surgical Clinics of North America, 78(6): 973-1006.

Decter, "Use of the Fascial Sling for Neurogenic Incontinence: Lessons Learned," J. Urol., 1993, 150:683-686.

Delmore, E. et al., La bandelette trans-obturatrice: Un procede mini-invasif pour traiter l'incontinence urinaire d'effort de la femme, Progres en Urologie, vol. 11, pp. 1306-1313 (2001) [including English translation at the beginning of document].

deTayrac, et al. Prolapse repair by vaginal route using . . . Int. Urogynecol. J. (published online May 13, 2006).

Dwyer, Transvaginal repair of anterior and posterior compartment prolapse with Atrium polypropylene mesh, BJOG: An International Journal of Obstetrics & Gynaecology, Aug. 2004.

Enzelsberger et al., "Urodynamic and Radiologic Parameters Before and After Loop Surgery for Recurrent Urinary Stress Incontinence," Acta Obstet. Gynecol. Scand., 1990, 69:51-54.

Eriksen et al., "Long-Term Effectiveness of the Burch Colposuspension in Female Urinary Stress Incontinence," Acta Obstet. Gynecol. Scand., 1990, 69:45-50.

Falconer et al., "Clinical Outcome and Changes in Connective Tissue Metabolism After Intravaginal Slingplasty in Stress Incontinent Women," Int. Urogynecol. J., 1996, 7:133-137.

Falconer et al., "Influence of Different Sling Materials on Connective Tissue Metabolism in Stress Urinary Incontinent Women," Int. Urogynecol. J., 2001, (Suppl. 2):S19-S23.

Gilja et al., "A Modified Raz Bladder Neck Suspension Operation (Transvaginal Burch)," J. Urol., 1995, 153:1455-1457.

Gittes and Loughlin, "No-Incision Pubovaginal Suspension for Stress Incontinence," J. Urol., 1987, 138:568-570.

Gruss, "The Obturator Bypass. Indications. Techniques. Outcomes," Chirurgie, 1971, 97:220-226.

Guida and Moore, "The Surgeon At Work. Obturator Bypass Technique," Surgery, Gynecology & Obstetrics, 1969, pp. 1307-1315.

Handa et al., "Banked Human Fascia Lata for the Suburethral Sling Procedure: A Preliminary Report," Obstet. Gynecol., 1996, 88:1045-1049.

Hardiman, et al. Cystocele repair using polypropylene mesh. Br. J. Obstet. Gynaecol. 107: 825-26 (2000).

Henriksson and Ulmsten, "A urodynamic evaluation of the effects of abdominal urethrocystopexy and vaginal sling urethroplasty in women with stress incontinence," Am. J. Obstet. Gynecol., 1978, 131:77-82.

Hodgkinson and Kelly, "Urinary Stress Incontinence in the Female. III. Round-ligament technique for retropubic suspension of the urethra," Obstet. Gynecol., 1957, 10:493-499.

* cited by examiner (n)

(o)

(p)

(q)

METHOD FOR FIBROUS ANCHORING OF A PELVIC SUPPORT

CROSS-REFERENCE TO RELATED APPLICATIONS

This application is a continuation of U.S. patent application Ser. No. 11/324,028, filed Dec. 30, 2005, which is a continuation-in-part of U.S. patent application Ser. No. 10/510,488, filed Mar. 28, 2005, now abandoned, which is a U.S. national stage application of International Patent Application No. PCT/GB03/01573, filed Apr. 11, 2003, which claims priority to and the benefit of U.S. Provisional Patent Application No. 60/393,969, filed Jul. 5, 2002, and Great Britain Patent Application No. 0208359.0, filed Apr. 11, 2002. This application claims priority to each of the foregoing applications and incorporates each of the foregoing applications herein by reference, in their entireties and for all purposes. This application incorporates each of the following applications herein by reference, in their entireties and for all purposes: U.S. patent application Ser. No. 11/199,061, filed Aug. 8, 2005, issued as U.S. Pat. No. 7,789,821 on Sep. 7, 2010, which is a continuation of U.S. patent application Ser. No. 10/398,992, filed Apr. 11, 2003, issued as U.S. Pat. No. 6,960,160 on Nov. 1, 2005, which is a U.S. national stage application of International Patent Application No. PCT/GB01/04554, filed Oct. 12, 2001, which claims priority to and the benefit of Great Britain Patent Application No. 0025068.8, filed Oct. 12, 2000.

FIELD OF THE INVENTION

This invention relates to an apparatus and method for treating female urinary incontinence and, in particular, to a surgical implant having a sling that passes under the urethra in use and supports the urethra to alleviate incontinence, along with related apparatus and methods for inserting the surgical implant in the body.

BACKGROUND OF THE INVENTION

Urinary incontinence affects a large number of women and, consequently, various approaches have been developed to treat female urinary incontinence. Those skilled in the art will be familiar with approaches ranging from pelvic floor exercises to surgical techniques such as Burch colposuspension and Stamey type endoscopic procedures in which the sutures are placed so as to elevate the bladder neck.

One known procedure positions a sling loosely under the urethra. It is generally understood that this treatment alleviates urinary incontinence by occluding the mid-urethra (for example at a time of raised abdominal pressure by coughing or the like).

As is known, a sling is provided in the body using two large curved needles which are provided at each end of the sling, where the sling comprises a long mesh or tape. Each of the needles is carried on an insertion tool (which is basically a handle facilitating manipulation of the needles). The mesh or tape is usually made of knitted polypropylene (such as Prolene®). The mesh or tape is generally covered with a plastics sleeve or polyethene envelope to aid smooth insertion, the mesh or tape having rough surfaces to aid retention in the body.

An incision is made in the anterior vaginal wall and the first of the needles is passed through the incision, past one side of the urethra, behind the pubic bone, through the rectus sheath and out through the lower anterior abdominal wall. Likewise, the second needle is passed through the incision, past the other side of the urethra, behind the pubic bone, through the rectus sheath and out through the lower abdominal wall. The needles are separated from their respective insertion tools and also from the mesh or tape such that only the tape and its plastics sleeve are left in the body, passing from a first exit point in the lower abdominal wall, through the rectus sheath, behind the pubic bone, under the urethra, back behind the pubic bone, back through the rectus sheath and out through a second exit point in the lower abdominal wall.

The plastics sleeve is then removed from the tape and the tape adjusted to a suitable tension (such that the tape provides a sling that passes loosely under the urethra, as described above) by maneuvering the free ends of the tape outside the exit points in the lower abdominal wall whilst the urethra is held using a rigid catheter inserted therein. The tape is then cut such that it just falls short of protruding from the exit points in the lower abdominal wall. The exit points and the incision in the upper vaginal wall are then closed by sutures. The tape is held in position by virtue of friction between the tape's rough edges and the surrounding body tissue (such as the rectus sheath and the body tissue behind the pubic bone) and subsequent natural adhesion of the tape with the body tissue as it re-grows around the mesh material.

Whilst highly effective in treating urinary incontinence, this procedure has a number of problems. One such problem is that the needles used for inserting the tape are comparatively large, with the needles having, for example, a diameter of around 5-6 mm and a length of around 200 mm. As well as causing concern for patients viewing such needles before or during the procedure (which is carried out under local anesthetic), this can also lead to a high vascular injury rate.

Similarly, the requirement that the needles exit the lower abdominal wall is disadvantageous due to the trauma to the patient in this area and pain of such abdominal wounds. A further disadvantage is that the tape comprises a relatively large foreign body mass to be retained within the patient and this can lead to related inflammation, infection translocation, erosion, fistula and such like.

Similarly, the nature of the large needles and tape, along with the tools required to insert these in the body, lead to the procedure having a relatively high cost.

In another known procedure which may be used to correct urinary incontinence, as shown in FIGS. 24 and 25, an incision is made in the perineal skin over a patient's first obturator foramen 134 and an incision 117 is made in the wall of the patient's vagina 116, a surgical instrument is inserted through the cutaneous incision, over the first obturator foramen 134 and passed through the obturator foramen (134) at a "safe" zone (138) close to the inferior pubic ramus (140), through the obturator muscle, and through the vaginal incision. A surgical implant is attached to the surgical instrument and the surgical instrument with the implant attached is retracted such that one end of the implant is pulled out of the body via the incision over the obturator foramen. A second incision is provided over the patient's second obturator foramen and the procedure repeated such that the implant is provided under the urethra 118 with a first end of the implant extending out of the first incision made over the first obturator foramen and a second end of the implant extending out of the second incision made over the second obturator foramen.

The requirement that the needles exit the body over the obturator foramen is disadvantageous due to the trauma to the patient in this area and pain of such wounds. A further disadvantage is that the implant comprises a relatively large foreign body mass to be retained within the patient and this can lead to related inflammation, infection translocation, erosion, fistula and such like. Furthermore, anatomical damage to nerves and blood vessels may occur during procedures which penetrate the obturator foramen.

SUMMARY OF THE INVENTION

I.

According to one aspect of the present invention there is provided a surgical implant for supporting the urethra, the implant comprising: a suburethral support suspended between at least two soft tissue anchors attached at either side of the suburethral support, each soft tissue anchor having retaining means for retaining each anchor in tissue and suspending means for suspending each side of the suburethral support from a soft tissue anchor such that the suburethral support passes under the urethra in use.

In one embodiment, a method of supporting a urethra comprises the steps of: introducing a surgical implant comprising first and second soft tissue anchors and a suburethral support portion therebetween into at least one incision made on the upper wall of a vagina; inserting the first soft tissue anchor on a first side of the urethra behind the pubic bone, and inserting the second soft tissue anchor on a second side of the urethra behind the pubic bone, such that the suburethral support is suspended from the soft tissue anchor and supports the urethra. Each of the first and second soft tissue anchors are inserted in and fix in the soft tissue of the perineum without penetrating the obturator foramen.

In another embodiment, a method of supporting a urethra comprises the steps of: introducing a surgical implant into at least one incision made on the upper wall of a vagina the surgical implant comprising first and second ends and a suburethral support section therebetween; inserting a first end of the surgical implant on a first side of the urethra and positioning the first end into soft tissue of the perineum without penetrating the obturator foramen; and inserting a second end of the surgical implant on a second side of the urethra and positioning the second end into the soft tissue of the perineum without penetrating the obturator foramen such that the suburethral support section is positioned under the urethra and provides support thereto.

In another embodiment, a method of supporting a urethra comprises: mechanically coupling, with a surgical implant, a first soft tissue portion of a perineum on a first side of the urethra to a second soft tissue portion of the perineum on a second side of the urethra, wherein the urethra is positioned between the first and second tissue portion, and orientating a portion of the surgical implant underneath the urethra to provide support thereto, wherein the obturator foramen is not penetrated.

In an embodiment of the surgical implant of the present invention the soft tissue anchor is capable of anchoring in the soft tissue of the perineum.

Preferably the soft tissue anchors comprise soft tissue anchors capable of anchoring in tissue of the retropubic space and/or tissue of the perineum at multiple points via a Christmas tree type configuration of deflectable wings.

A soft tissue anchor according to these embodiments comprises a central portion and the retaining means includes a plurality of projections the projections extending radially from the central portion along a substantial portion of the length of the central portion allowing fixation at a plurality of layers.

Preferably the projections extend radially from the central portion at an angle inclined toward the second end of the central portion.

Preferably the projections are of a shape that they are able to provide additive traction to the soft tissue anchor and allow it to grip fibro-fatty soft tissue and blood vessels of the paraurethral tunnel below the level of the rectus sheath and/or the soft tissue of the perineum.

In a preferred embodiment of the surgical implant the retaining means are moveable from an inserting position to a retaining position.

It is preferable if at least one of the retaining means of the implant is moveable from a collapsed position to an extended position as it enables the retaining means to actively move into tissue in at least one layer of the tissue following suitable location of the implant. The movement of the retaining means from a collapsed position to an extended position allows the means to move into and be retained in tissue which has been undisturbed or which has not been disrupted during placement of the implant. The collapsed position of the implant can be achieved by rolling up, folding, bending, or enclosing the implant in a restrained position.

It is more preferable if the retaining means can be moved from a collapsed position to an extended position at two or more layers in the tissue as this provides for gripping of the tissue by the implant at multiple sites which may require increased force to be used to dislodge the soft tissue anchors of the implant from the anchored positions in the fibro-fatty soft tissue of the retropubic space or from the soft tissue of the perineum.

Suitably the retaining means may be at least one projection which can project from the implant into the tissues of the retropubic space or the soft tissue of the perineum in at least one plane the projection being moveable from a collapsed position to an extended position.

In particular embodiments of the implant the retaining means comprise a plurality of projections extending laterally from the longitudinal axis of the implant.

Suitably the projections may extend from the longitudinal axis of the implant such that they point away from the bladder when the implant is positioned such that the suburethral support passes under the urethra.

In particular embodiments of the implant the projections may be curved such that they point away from bladder when the implant is positioned such that the suburethral support passes under the urethra.

In particular embodiments of the implant, the implant may be curved such that the longitudinal edges of the soft tissue anchors of the implant and thus the retaining means in use are directed away from the bladder.

In embodiments of the surgical implant wherein the retaining means are mechanical in nature in an inserting position the mechanical means are collapsed and in a retaining position the mechanical retaining means are in an extended position.

In embodiments of the surgical implant wherein the retaining means are chemical in nature, for example glue, in an inserting position the glue is in a state which minimizes its adhesion to the surrounding tissue and in a retaining position the glue is in a state which allows the glue to adhere to the surrounding fibro-fatty tissue in the retropubic space or in the soft tissue of the perineum. Thus in moving from an inserting position to a retaining position the presentation or the nature of the glue is changed to cause the glue to adhere the implant to the surrounding tissue.

The glue may be encapsulated (inserting position) within a capsule such that the glue cannot interact with the tissue during placement of the implant. When the implant is suitably located, the capsule of glue may be burst (retaining position) to release the glue and allow the implant to be fixed to the surrounding tissue.

In particular embodiments the glue is held in a releasable container. The glue containing releasable container may prevent the glue interacting with surrounding tissues until an appropriate point in the surgical procedure. At this point the surgeon may use means, for example a point on the introducing tool to release the glue from the container, for example by puncturing the container and enabling the glue to adhere the implant to the surrounding tissue.

Alternatively in particular embodiments of the implant the glue may be activated by some means, for example heat, light, cold or ultrasound. The implant may be moved into the fibro-fatty tissue of the retropubic space or the soft tissue of the perineum without the glue adhering the implant to the surrounding tissue (inserting position) then following the activation of the glue or change in state of the glue by some means, not limited to heat, light, cold or ultrasound, the glue will adhere the implant to the surrounding tissues (retaining position).

It is preferable if the implant has minimal mass to reduce the likelihood of inflammation or rejection of the implant when it is located in the body. Further, it is preferable that the implant comprises as little material as allows support of the urethra during periods of increased intra-abdominal pressure to minimize the abrasion or the urethra and the likelihood of adhesions forming at the urethra.

In addition, it is advantageous if the tissue anchors and the suburethral support are integral with each other as it allows easier manufacture of the implant. As the distance from the supporting region under the urethra to the fixing points in the fibro-fatty tissue of the retropubic space and/or in the soft tissue of perineum are relatively short in comparison to the distances between the suburethral support and the fixing points described in the implants of the prior art, the overall size of the implant of the present invention can be reduced.

The production of an implant from a portion of tape material is advantageous as it allows easier manufacture than implants comprising multiple portions comprising of different materials which have to be fixed together. This design minimizes the risk of failure of the implant due to the simplicity of the implant and provides for easier packaging and sterilization of the implant.

The soft tissue anchors of the implant must be anchored in the tissues of the retropubic space or the tissue of the perineum with adequate tensile strength to counter dislodging by coughing until suitable integration of tissue occurs with the implant.

At least two forces are exerted on the surgical implant portion which extends under the urethra. A first force is the force exerted by the urethra during increased intra-abdominal pressure. The surgical implant has to be secured in the fibro-fatty tissue of the retropubic space or the soft tissue of the perineum such that it is capable of supporting the urethra and occluding the urethra at periods of increased intra-abdominal pressure, to minimize incontinence.

A second force is the force exerted on the surgical implant during periods of increased intra-abdominal pressure which acts in a direction opposite to the direction in which the anchors are inserted into the retropubic space or the soft tissue of the perineum. This force can be considered to be a force of dislodgement.

Suitably the implant is anchored in the fibro-fatty tissues of the retropubic space and/or the soft tissue of the perineum such that the implant can resist forces of dislodgement created during periods of increased intra-abdominal pressure.

Coughing and other causes of increased abdominal pressure typically cause increased pressures of around 200-400 cm water. This has been determined by the Applicant to be equivalent to around a force of 3.75 N through each tape arm.

Suitably the implant is anchored in the fibro-fatty tissues of the retropubic space or soft tissue of the perineum such that the implant can resist forces of dislodgement created during periods of increased intra-abdominal pressure of up to 3 N.

In particular embodiments, the implant may be anchored in the fibro-fatty tissues of the retropubic space or soft tissue of the perineum such that the implant can resist forces of dislodgement of up to 5 N.

In further embodiments the implant may be anchored in the fibro-fatty tissues of the retropubic space or soft tissue of the perineum such that it can resist forces of dislodgement of up to 10 N.

In embodiments of the implant a soft tissue anchor may comprise a plurality of retaining means.

In embodiments of the implant a soft tissue anchor may be tapered.

Curvature of the longitudinal edges of the soft tissue anchor such that they are directed away from the bladder minimizes medial presentation of the retaining means such as projections to the bladder minimizing erosion of the bladder.

In a particular embodiment of the implant a soft tissue anchor may be shaped as a serrated arrowhead wherein the base portion of the arrowhead is conjoined to the suburethral support.

The serrated arrowhead may be provided by cutting a flat tape such that the serration's of the arrowhead exist in two dimensions only.

Suitably the soft tissue anchor may have a pointed end at a first end, a base portion at a second end, wherein the longitudinal edges extend between the pointed end and the base and the longitudinal edges are notched to provide a row of projections extending outward from the longitudinal edges.

In other words the anchor may have a pointed tip at a first end and a base portion at a second end, the first end being the end of the anchor furthest from the suburethral support and the base portion being conjoined to the suburethral support. The longitudinal edges of the anchor extend from the pointed tip to the base wherein the longitudinal edges are notched to from a row of tooth like projections extending from the longitudinal edge.

In yet a further embodiment the soft tissue anchor may comprise a substantially flat head the bottom surface nearest the suspending means of the flat head providing the retaining means which, in use is held in the rectus sheath.

In a further embodiment the soft tissue anchor may comprise a sharp point allowing it to pierce or penetrate the rectus sheath, and retaining means comprising a surface or protrusion directed rearwardly with respect to the sharp point which does not cause the soft tissue to part and thus prevents the soft tissue anchor from being pulled back out through the rectus sheath soft tissue in the direction opposite to that in which it is inserted into the soft tissue.

Preferably the sharp point is provided by the apex of a conical head portion and retaining means are provided by a substantially flat base of the conical head.

Suitably a soft tissue anchor as described herein for anchoring into the fibro-fatty tissues of the retropubic space may be used to anchor in the soft tissue of the perineum.

In any embodiment the soft tissue anchor may be comprised of plastics material.

Typically the soft tissue anchor may be comprised of polypropylene.

Alternatively the soft tissue anchor is comprised of absorbable material so as to form temporary fixation in soft tissue.

The soft tissue anchor may comprise a point formed of absorbable material including polyglactin, the sharp point thus capable of facilitating insertion of the anchor, yet being absorbed by the body later.

Preferably the soft tissue anchor may be integral with the suspending means.

More preferably the soft tissue anchor is integrally formed from polypropylene or other polymeric material the attachment between the anchor and the suspending means being formed as a single unit.

An integral construction of the soft tissue anchor and suspending means has the advantage of simplifying the construction of the soft tissue anchor and suspending means, which can reduce the possibility of defective manufacture etc. and reduce costs and the chance of the soft tissue anchor and suspending means becoming detached once implanted in the body.

Alternatively the soft tissue anchor is attached to the suspending means by a thin metal tube crimped or otherwise attached around the suspending means and central portion of the soft tissue anchor.

The suburethral support of the first aspect of the invention passes under the urethra, loosely supporting the urethra, the suburethral support being held in position by suspending means attached to each of its free ends on either side of the urethra, the suspending means being attached at the opposite end to at least one soft tissue anchor.

Preferably the suburethral support is comprised of flat polymer tape.

Preferably the suburethral support has dimensions sufficient only to pass around the urethra.

More preferably the suburethral support has dimensions of length 15-35 mm, width 5-15 mm and thickness 50-350 mm.

In one embodiment the suburethral support has dimensions of length 25 mm, width 10 mm and thickness 100 mm.

Preferably the suburethral support has at least two junctions to attach the suburethral support to the suspending means.

Preferably the distance between the soft tissue anchor(s) and the suburethral support is adjustable.

The surgical implant is preferably of a length in the range 12 cm to 16 cm.

More preferably the soft tissue anchor (or anchors) can be positioned first and the suburethral support then positioned by adjusting the length of the suspending means.

Preferably the suburethral support is provided with at least one attachment tab to which suspending means are releasably or permanently attached.

In particular embodiments of the surgical implant the suburethral support is provided by a mesh. Advantageously when the suburethral support is provided by a mesh, the mesh is resilient to such an extent that it mimics the physiological elasticity of the tissues which would normally support the urethra.

In embodiments of the implant wherein the suburethral support is formed from mesh the strands of the mesh may be spaced apart to form spaces of 1 to 10 mm. Suitably the strands may have a diameter of less than 600 mm. Suitably the strands of the mesh may be arranged to form a warp knit diamond or hexagonal net mesh.

In particular embodiments of the implant the suburethral support may be formed from polyester or polypropylene. Alternatively, the suburethral support may be formed from absorbable material or may be encapsulated by an absorbable coating. In particular embodiments, such a coating may be applied to only one side of the implant.

In further embodiments the suburethral support may be formed from biocomponent microfibres comprising a core and surface material. For example, the surface material may be readily absorbable by the body while the core material may remain in the body for a longer period of time. Suitably the surface material may be polylactic acid and the core material may be polypropylene.

The suburethral support of the implant may be absorbable at a different rate than the soft tissue anchors of the implant, for example the soft tissue anchors may be absorbed within six weeks of implantation, while the soft tissue anchors may remain for 9 months.

Preferably the suburethral support comprises an attachment tab comprising a tunneled element and an aperture, the tunneled element being located at each of the free ends of the suburethral support on either side of the urethra at a position that the suspending means are capable of being introduced through, the tunneled element co-operating with the aperture such that suspending means can be passed through the tunneled element and then through the aperture, the aperture being present on the opposite surface of the suburethral support to that which contacts the urethra the aperture having an edge capable of co-operating with a ring element and the ring element being capable of being fitted around the aperture trapping the suspending means between the ring element and the edge of the aperture such that the suspending means remain fixed in an adjusted position wherein the suburethral support hangs loosely under the urethra.

Alternatively the attachment tab comprises at least one slot through which suspending means can be passed, the suspending means being permanently attached to the slot by tying.

Alternatively the attachment tab comprises jamming slots that the suspending means can be permanently attached by being threaded through the jamming slots such that the suspending means are held in an adjusted position.

Alternatively the suburethral support is capable of being suitably positioned under the urethra by altering the position of the soft tissue anchors within the body such that at least one soft tissue anchor is secured in the soft tissue or in the rectus sheath and a subsequent anchor is inserted into the soft tissue or rectus sheath to a suitable depth such that the suburethral support hangs loosely under the urethra.

Alternatively the suspending means may be attached to the suburethral support by heating such that the suburethral support and/or suspending means melt and form a join.

Alternatively the attachment tabs may have closure means for gripping the suspending means.

The suspending means may be any means suitable for connecting each end of the suburethral support to the soft tissue anchor (or respective soft tissue anchors).

Preferably the suspending means comprises a plastics strip.

Preferably the plastics strip has smooth edges.

Preferably the plastics strip comprises material such as polypropylene or other suitable non-absorbable or absorbable polymer tape.

Preferably the plastics strip is 3-5 mm in width.

Preferably the plastics material comprises pores which extend through the plastics material from a first surface of the plastics material to a second opposite surface of the plastics material said pores ranging in width across the surface of the plastics material from 50 mm to 200 mm, the pores allowing tissue in-growth to secure the strip in the body.

Alternatively the plastics material may comprise pits, that indent but do not extend through the plastics material, on at least one of the surfaces of the plastics material, the pits ranging in width from 50 mm to 200 mm, the pits allowing tissue in-growth to secure the strip in the body.

Preferably the plastics material comprises pits or pores ranging in width across the surface of the plastics material from 100 mm to 150 mm.

Preferably the pits or pores are distributed across the complete surface of the plastics material.

Alternatively the pits or pores are distributed only in a particular portion of the surface of the plastics material.

Preferably the pits or pores are created by post synthesis modification of the plastics material.

More preferably the pits or pores are created by post synthesis treatment of the plastics material by a laser.

Alternatively the pits or pores of between 50-200 mm are created during synthesis of the plastics material by spaces between the waft and weave of mono-filament or multi-filament yarns when the filaments are woven to form a mesh.

Alternatively pits or pores formed during the synthesis of plastics material are formed by the inter-filament spaces created when mono-filaments are twisted to create multi-filaments, the multi-filaments then being woven to form a mesh.

In an embodiment the suspending means is provided with a plurality of microgrooves of width between 0.5-7 μm and of depth 0.25-7 μm on at least one surface of the plastics strip.

Preferably the microgrooves are 5 μm in width and 5 μm in depth.

Preferably the plurality of microgrooves are aligned such that they are substantially parallel with each other.

Preferably the plurality of microgrooves are aligned such that they are separated by ridges which range in size between 1-5 μm in width.

More preferably the microgrooves are separated by ridges of 5 μm in width.

Preferably the ridges are formed by square pillars and the base of the microgroove is substantially perpendicular to the square pillars.

Alternatively the ridges are formed by square pillars and the base of the microgroove is beveled in relation to the pillars.

Preferably the microgrooves are present on at least one surface of the suspending means.

More preferably the microgrooves are present on a plurality of surfaces of the suspending means.

These microgrooves act to orientate and align the proliferating fibroblasts on the surface of the plastics material and cause axial alignment of collagen fibres and formation of at least one strong ordered neoligament.

The orientation and alignment of the proliferating cells is capable of adding mechanical strength to the tissue which forms around the plastics material such that it is more able to support the urethra.

Preferably the suburethral support of the present invention has neither pores, pits or grooves to discourage the formation of peri-urethral adhesions.

Suitably the implant may be comprised of non-absorbable material. Alternatively the implant may be comprised of absorbable material. In particular embodiments of the implant, the implant is comprised of polypropylene.

Preferably the implant is comprised of resilient material such that if the implant is not restrained it adopts the original shape defined during production of the implant.

It would be advantageous if the implant was capable of longitudinal extension such that it still provides suitable support to the urethra during periods of increased abdominal pressure, but is able to move and extend in a similar fashion to tissues which physiologically support the urethra.

In suitable embodiments of the implant, there may be provided a resilient zone wherein the resilient zone provides for the resilient extension of the surgical implant in a longitudinal direction such that the surgical implant behaves in a similar manner to dynamic bodily tissue.

In particular embodiments of the implant the resilient zone is located in at least one of the anchors of the implant.

Alternatively the resilient zone is interposed between an anchor and the suburethral support.

The resilient zone of the implant may be capable of allowing the resilient extension of at least part of the implant due to its geometric design.

Alternatively the resilient zone of the implant may be capable of allowing resilient extension of at least part of the implant due to its micro material design.

In particular embodiments of the implant, the resilient zone of the implant may be capable of allowing the resilient extension of the implant due to a combination of its geometric and micro material design.

The geometric design may include multiple strips of material.

In particular embodiments the geometric design may include multiple strips of material arranged into bows, the bows being capable of deforming and providing resilient extension to the implant.

Alternatively the geometric design may comprise a concertina portion such that a part of the implant can extend in a direction substantially perpendicular to the folds of the concertina.

In other words the implant may comprise a folded portion, the fold perpendicular to the longitudinal axis of the implant, which allows limited extension of the implant in a longitudinal direction. In an extended position a folded portion is moved away from a second folded position. In a closed portion the folded portions are brought together. Different amounts of force in a longitudinal direction may be required to move the concertina portion from a closed to an open position.

Suitably resilient extension of a portion of the implant may occur when an extension force of 1 to 5 N is applied to the implant along its length.

Resilient extension of a portion of the implant may occur when an extension force of 2 to 3 N is applied to the implant along its length.

The resilient zone may provide for the extension of the implant along its longitudinal length of around 2 to 5 mm.

In embodiments of the surgical implant the unextended implant may be of length 6 to 22 cm.

More preferably the unextended implant is of length 8 to 20 cm.

Most preferably the surgical implant is of unextended length 10 to 15 cm.

It will be understood that in embodiments of the implant which do not include a resilient zone, the unextended length is equal to the length of the implant.

In particular embodiments of the implant each soft tissue anchor is of at least 1 cm in length and not greater than 8 cm in length.

Suitably each anchor may be 5 cm in length.

Suitably the suburethral support may be of at least 2 cm in length.

According to a second aspect of the present invention there is provided a method of supporting the urethra comprising the steps of, introducing a surgical implant as described above into an incision made on the upper wall of the vagina, inserting a soft tissue anchor on a first side of the urethra behind the pubic bone, inserting a second soft tissue anchor on a second side of the urethra behind the pubic bone, such that the suburethral support is suspended from the soft tissue anchor and supports the urethra.

The invention also provides the use of the method of supporting the urethra in treating urinary incontinence or uterovaginal prolapse.

In one embodiment of the method the soft tissue anchors are inserted in the rectus sheath.

In an alternative embodiment of the method the soft tissue anchors are inserted in the fibro-fatty soft tissue of the retropubic tissue space and do not penetrate the rectus sheath.

In an alternative embodiment of the method the soft tissue anchors are inserted in and fix in the soft tissue of the perineum.

As indicated above, the above methods have the advantage that only a single vaginal incision is required for introduction of the surgical implant and the need for exit of the surgical implant and thus exit wounds is removed, for example exit wounds in the abdomen or at the obturator foramen are not required.

In particular embodiments of the method wherein the soft tissue anchors are inserted in and fix in the soft tissue of the perineum, the surgical implant does not penetrate the endopelvic fascia.

In none of the embodiments of the method does the surgical implant penetrate of extend through the obturator foramen.

Suitably in one embodiment of the method wherein the soft tissue anchors are inserted and fix in the soft tissue of the perineum there is provided a method of supporting the urethra comprising the steps of: introducing a surgical implant comprising first and second soft tissue anchors and a suburethral support therebetween into at least one incision made on the upper wall of the vagina, inserting a first soft tissue anchor on a first side of the urethra in a lateral direction away from the urethra, inserting a second soft tissue anchor on a second side of the urethra in an opposite lateral direction from the first soft tissue anchor and away from the urethra, such that the suburethral support is suspended from the first and second soft tissue anchors and supports the urethra, wherein each of the first and second soft tissue anchors is positioned in the soft tissue which comprise the perineum.

In another embodiment a method of supporting the urethra comprises the steps of: introducing a surgical implant into at least one incision made on the upper wall of the vagina the surgical implant comprising first and second ends and a suburethral support section therebetween; inserting a first end of the surgical implant on a first side of the urethra and positioning the first end into the soft tissue of the perineum without penetrating the obturator foramen; inserting a second end of the surgical implant on a second side of the urethra and positioning the second end into the soft tissue of the perineum without penetrating the obturator foramen such that the suburethral support section is positioned under the urethra and provides support thereto.

In a further embodiment the method of supporting a urethra, comprises the steps of: introducing a first end of a surgical implant into at least one incision made in a vaginal wall, the surgical implant comprising first and second ends and a suburethral portion there between; inserting the first end of the surgical implant on a first side of the urethra and positioning the first end into tissue of a perineum without penetrating the endopelvic fascia; introducing the second end of a surgical implant into the at least one incision made in a vaginal wall; inserting a second end of the surgical implant on a second side of the urethra and positioning the second end into tissue of the perineum without penetrating the endopelvic fascia such that the suburethral support portion is positioned underneath the urethra and provides support thereto.

Suitably a portion of the surgical implant grips at least one of first and second soft tissue portions of the perineum.

Suitably location of a first soft tissue anchor on a first side of the urethra in a first tissue of a perineum and a second soft tissue on a second side of the urethra in a second tissue of the perineum, wherein the urethra is positioned between said first and second soft tissue portions and the surgical implant is positioned underneath the urethra to provide support thereto, mechanically couples a first tissue of the perineum to the second tissue of the perineum.

In this method no part of the surgical implant penetrates the obturator foramen. In particular, no part of the surgical implant extends through the obturator foramen.

The soft tissue anchor(s) or ends do not penetrate or fix into bone.

In one embodiment of the method of anchoring the soft tissue anchors in the soft tissue of the perineum, a soft tissue anchor of an implant is inserted through an incision in an upper wall of a vagina and inserted towards a first obturator foramen behind an inferior pubic ramus until about half of the length of the implant is inserted. The soft tissue anchor of the implant is thus placed such that the soft tissue anchor is located in the soft tissue of the perineum. A second soft tissue anchor may then be inserted into the vaginal incision and inserted towards a second obturator foramen behind an inferior pubic ramus until the second half of the implant is inserted. The second soft tissue anchor of the implant is thus placed such that the soft tissue anchor is located in the soft tissue of the perineum.

In an embodiment of the method a first end of a surgical implant may be inserted through an incision in an upper wall of a vagina and inserted towards a first obturator foramen behind an inferior pubic ramus such that around 7 cm of the implant is inserted. A second end of a surgical implant may then be inserted through an incision in an upper wall of a vagina and inserted towards a second obturator foramen behind an inferior pubic ramus such that around 7 cm of the implant is inserted.

The locating of a soft tissue anchor in the soft tissue of the perineum may be advantageous as it is less likely that the bladder may be perforated than in retropubic methods where the needle passage is medial and therefore near to the bladder.

Typically the suburethral support is placed midurethra, without tension, but in a position to support the urethra. However, as will be understood by those skilled in the art, the suburethral support may be positioned at an alternative suitable anatomical location such as to be therapeutically effective should for example the midurethra be damaged or have significant scar tissue.

In an embodiment of the method, the soft tissue anchors do not penetrate the obturator muscle.

II.

The present invention relates to an apparatus and method for treating female urinary incontinence. In particular, the invention provides a surgical implant that passes under the urethra in use and supports the urethra, the implant being anchored in the retropubic space is provided.

Urinary incontinence affects a large number of women and, consequently, various approaches have been developed to treat female urinary incontinence. Those skilled in the art will be familiar with approaches ranging from pelvic floor exercises to surgical techniques such as Burch colposuspension and Stamey-type endoscopic procedures in which sutures are placed so as to elevate the bladder neck.

This invention is particularly directed to improvement of a known procedure in which a sling is positioned loosely under the urethra, commonly known as TVT (tension free vaginal tape) and described, for example, in International Patent Applications No. WO97/13465 and WO96/06567. It is generally understood that this treatment alleviates urinary incontinence by occluding the mid-urethra (for example at a time of raised abdominal pressure by coughing or the like).

In order to provide a sling loosely under the urethra using the apparatus and method of the prior art, an incision is made in the anterior vaginal wall and a first needle is passed through the incision, past one side of the urethra, behind the pubic bone, through the rectus sheath and out through the lower anterior abdominal wall. Likewise, a second needle is passed through the incision, past the other side of the urethra, behind the pubic bone, through the rectus sheath and out through the lower abdominal wall. The needles are separated from their respective insertion tools and also from the mesh or tape such that only the tape and its plastics sleeve are left in the body, passing from a first exit point in the lower abdominal wall, through the rectus sheath, behind the pubic bone, under the urethra, back behind the pubic bone, back through the rectus sheath and out through a second exit point in the lower abdominal wall.

The plastics sleeve is then removed from the tape and tape adjusted to a suitable tension such that the tape provides a sling that passes loosely under the urethra, as described above) by maneuvering the free ends of the tape outside the exit points in the lower abdominal wall whilst the urethra is held using a rigid catheter inserted therein. The tape is then cut such that it just falls short of protruding from the exit points in the lower abdominal wall. The exit points and the incision in the upper vaginal wall are then closed by sutures.

Whilst highly effective in treating urinary incontinence, this procedure has a number of problems. One such problem is that the needles used for inserting the tape are comparatively large, with the needles having, for example, a diameter of around 5-6 mm and a length of around 200 mm. As well as causing concern for patients viewing such needles before or in some cases during the procedure, the size of the needles can also lead to a high vascular injury rate.

Similarly, the requirement that the needles exit the lower abdominal wall is disadvantageous due to the trauma to the patient in this area and the pain of such abdominal wounds. A further disadvantage is that, as the tape is required to extend from the lower abdomen wall under the urethra and back through the lower abdomen wall, the tape must comprise a relatively large foreign body mass (typically around 25 to 28 cm) to be retained within the patient. This can lead to related inflammation, infection translocation, erosion, fistula and such like.

Similarly, the nature of the large needles and tape, along with the tools required to insert these in the body, lead to the procedure having a relatively high cost.

Further details of the apparatus and methods of the prior art are provided in International Patent Application No PCT/GB01/04554.

It would be advantageous if an implant such as a sling could be inserted into the body such that it is positioned loosely under the urethra without requiring penetration of the abdominal wall or rectus sheath. Most of the pain associated with previous procedures to introduce an implant as described above is due to the force required to penetrate the tough structures of the abdominal wall or rectus sheath, both of which are highly innervated. The suitable location of an implant such that it hangs loosely under the urethra without requiring penetration of the lower abdomen or rectus sheath would reduce the trauma experienced by the patient. Further, a greater number of major blood vessels are located in the retropubic space towards the rectus sheath than toward the endopelvic fascia and thus by suitably locating the implant, without piercing the rectus sheath, damage to these blood vessels would be minimised. This would reduce the amount of bleeding experienced by the patient. In addition, such location of an implant with a reduced level of trauma may allow the procedure to be performed under local anaesthetic in an out patient or office setting.

Ideally an implant such as a sling used to treat female urinary incontinence includes means to adjust the position of the suburethral portion of the sling such that this portion passes under the urethra and is able to occlude the mid urethra at times of raised abdominal pressure. In addition, the implant should have minimal mass, when implanted in the body, to reduce the likelihood of inflammation and the like as discussed above.

According to the present invention there is provided a surgical implant for supporting the urethra, the implant including at least two fixing zones and a supporting zone, the supporting zone being interposed between the fixing zones and the fixing zones each having at least one retaining means for anchoring the fixing zones in the tissues of the retropubic space, without penetrating the rectus sheath such that in use the supporting zone passes under the urethra.

Preferably the fixing zones are anchored in the tissues of the retropubic space above the endopelvic fascia.

The retropubic space above the endopelvic fascia equates to the same pressure compartment as the intra-abdominal pressure compartment.

Preferably the retaining means are moveable from an inserting position to a retaining position.

Preferably the retaining means is at least one projection which can project from the implant into the tissues of the retropubic space in at least one plane the projection being moveable from a collapsed position to an extended position.

Where the retaining means are mechanical in nature in an inserting position the mechanical means are collapsed and in a retaining position the mechanical retaining means are in an extended position.

Where the retaining means are chemical in nature, for example glue in an inserting position the glue is in a state which minimises its adhesion to the surrounding tissue and in a retaining position the glue is in a state which allows the glue to adhere to the surrounding tissue. Thus in moving from a inserting position to a retaining position the presentation or the nature of the glue is changed to cause the glue to adhere the implant to the surrounding tissue.

The glue may be encapsulated (inserting position) within a capsule such that the glue cannot interact with the tissue during placement of the implant.

When the implant is suitably located, the capsule of glue may be burst (retaining position) to release the glue and allow the implant to be fixed to the surrounding tissue.

Alternatively the glue may be activated by some means, for example heat, light, cold or ultrasound. The implant can be moved into the retropubic tissue without the glue adhering the implant to the surrounding tissue (inserting position) then following the activation of the glue or change in state of the glue by some means, not limited to heat, light, cold or ultrasound, the glue will adhere the implant to the surrounding tissues (retaining position).

It is preferable if the implant has minimal mass to reduce the likelihood of inflammation or rejection of the implant when it is located in the body. Further, it is preferable that the implant comprises as little material as allows support of the urethra during periods of increased intra-abdominal pressure to minimise the abrasion or the urethra and the likelihood of adhesions forming at the urethra.

In addition, it is preferable if the fixing zone and the supporting zone are integral with each other as it allows easier manufacture of the implant. As the distance from the supporting region under the urethra to the fixing points in the retropubic space are relatively short in comparison to the distances between the supporting zone and the fixing zones described in the implants of the prior art, the overall size of the implant can be reduced.

The production of an implant from a portion of tape material is preferable as it allows easier manufacture than implants comprising multiple portions comprising of different materials which have to be fixed together, it minimises the risk of failure of the implant due to the simplicity of the implant and provides for easier packaging and sterilisation of the implant.

It is preferable if at least one of the retaining means of the implant is moveable from a collapsed position to an extended position as it enables the retaining means to actively move into tissue in at least one layer of the tissue following suitable location of the implant. The movement of the retaining means from a collapsed position to an extended position allows the means to move into and be retained in tissue which was been undisturbed or which has not been disrupted during placement of the implant. The collapsed position of the implant can be achieved by rolling up, folding, bending, or enclosing the implant in a restrained position.

It is more preferable if the retaining means can be moved from a collapsed position to an extended position at two or more layers in the tissue as this provides for gripping of the tissue by the implant at multiple sites which may require increased force to be used to dislodge fixing zones of the implant from the anchored positions in the retropubic space.

The fixing zone of the implant must be anchored in the tissues of the retropubic space with adequate tensile strength to counter dislodging by coughing until suitable integration of tissue occurs. At least two forces are exerted on the tape which extends under the urethra. A first force is the force exerted by the urethra during increased intra-abdominal pressure. The tape has to be secured in the retropubic space such that it is capable of supporting the urethra and occluding the urethra at periods of increased intra-abdominal pressure, to minimise incontinence.

A second force is the force exerted on the tape during periods of increased intra-abdominal pressure which acts in a direction opposite to the direction in which the fixing means are inserted into the retropubic space. This force can be considered to be a force of dislodgement.

Preferably the implant is anchored in the tissues of the retropubic space such that the implant can resist forces of dislodgement created during periods of increased intra-abdominal pressure.

Coughing and other causes of increased abdominal pressure typically cause increased pressures of around 200-400 cm water. This has been determined by the Applicant to be equivalent to around a force of 3.75 N through each tape arm.

Preferably the implant is anchored in the tissues of the retropubic space such that the implant can resist forces of dislodgement created during periods of increased intra-abdominal pressure of up to 3N.

More preferably the implant is anchored in the tissues of the retropubic space such that the implant can resist forces of dislodgement of up to 5N.

More preferably the implant is anchored in the tissues of the retropubic space such that it can resist forces of dislodgement of up to 10N.

Preferably each fixing zone comprises a plurality of retaining means.

Preferably the fixing zones are tapered

Preferably the retaining means comprise a plurality of projections extending laterally from the longitudinal axis of the implant.

More preferably the projections extend from the longitudinal axis of the implant such that they point away from the bladder when the implant is positioned such that the supporting zone passes under the urethra.

Preferably the projections are curved such that they point away from bladder when the implant is positioned such that the supporting zone passes under the urethra.

Preferably the implant is curved such that the longitudinal edges of the fixing zone of the implant and thus the retaining means in use are directed away from the bladder.

Curvature of the longitudinal edges of the fixing zone such that they are directed away from the bladder minimises medial presentation of the retaining means such as projections to the bladder minimising erosion of the bladder.

Preferably the fixing zone comprises the shape of a serrated arrowhead wherein the base portion of the arrowhead is conjoined to the supporting zone.

The serrated arrowhead can be provided by cutting a flat tape such that the serration's of the arrowhead exist in two dimensions only.

Preferably the fixing zone has a pointed end at a first end, a base portion at a second end, wherein the longitudinal edges extend between the pointed end and the base and the longitudinal edges are notched to provide a row of projections extending outward from the longitudinal edges.

In other words the fixing zone has a pointed tip at a first end and a base portion at a second end, the first end being the end of the fixing zone furthest from the supporting zone the base portion being conjoined to the supporting zone. The longitudinal edges of the fixing zone extending from the pointed tip to the base wherein the longitudinal edges are notched to from a row of tooth like projections extending from the longitudinal edge.

Alternatively the retaining means is glue.

Preferably the glue is cyanoacrylate glue.

More preferably the glue is held in a releasable container. The glue containing releasable container may prevent the glue interacting with surrounding tissues until an appropriate point in the surgical procedure. At this point the surgeon may use means, for example a point on the introducing tool to release the glue from the container, for example by puncturing the container and enabling the glue to adhere the implant to the surrounding tissue.

Preferably the implant is comprised of resilient material such that if the implant is not restrained it adopts the original shape defined during production of the implant.

Preferably the implant is comprised of plastics material.

More preferably the implant is comprised of polypropylene.

Preferably the implant is comprised of non-absorbable material.

Alternatively the implant is comprised of absorbable material.

It would be advantageous if the implant was capable of longitudinal extension such that it still provides suitable support to the urethra during periods of increased abdominal pressure, but is able to move and extend in a similar fashion to tissues which physiologically support the urethra.

Preferably the implant further comprises a resilient zone wherein the resilient zone provides for the resilient extension of the tape such that the tape behaves in a similar manner to dynamic bodily tissue.

Preferably the resilient zone is located in at least one of the fixing zones of the implant.

Alternatively the resilient zone is interposed between the fixing zone and the supporting zone.

Preferably the resilient zone of the implant is capable of allowing the resilient extension of at least part of the implant due to its geometric design.

Alternatively the resilient zone of the implant is capable of allowing resilient extension of at least part of the implant due to its micro material design.

More preferably the resilient zone of the implant is capable of allowing the resilient extension of the implant due to a combination of its geometric and micro material design.

Preferably the geometric design includes multiple strips of material.

More preferably the geometric design includes multiple strips of material arranged into bows, the bows being capable of deforming and providing resilient extension to the implant.

Alternatively the geometric design comprises a concertina portion such that a part of the implant can extend in a direction substantially perpendicular to the folds of the concertina.

In other words the implant comprises a folded portion, the fold perpendicular to the longitudinal axis of the implant, which allows limited extension of the implant in a longitudinal direction. In an extended position a folded portion is moved away from a second folded position. In a closed portion the folded portions are brought together. Different amounts of force in a longitudinal direction may be required to move the concertina portion from a closed to an open position.

Preferably resilient extension of a portion of the implant occurs when an extension force of 1 to 5 N is applied to the implant along its length.

Preferably resilient extension of a portion of the implant occurs when an extension force of 2 to 3 N is applied to the implant along its length.

Preferably the resilient zone provides for the extension of the implant along its longitudinal length of around 2 to 5 mm.

Preferably the unextended implant is of length 6 to 22 cm.

More preferably the unextended implant is of length 8 to 20 cm.

Most preferably the surgical implant is of unextended length 10 to 15 cm.

Preferably each fixing zone is of at least 1 cm in length and not greater than 8 cm in length.

More preferably each fixing zone is 5 cm in length.

Preferably the supporting zone is of at least 2 cm in length.

Preferably the tape of the supporting zone is a mesh.

Preferably the mesh is resilient.

Preferably the mesh is resilient to such an extent that it mimics the physiological elasticity of tissues which would normally support the urethra.

Preferably the mesh comprises strands and includes major spaces and pores, the major spaces existing between the strands and pores formed within the strands.

Preferably the strands are formed from at least two filaments.

Preferably the strands are spaced apart to form major spaces of 1 to 10 mm.

Preferably the strands have a diameter of less than 600 µm.

Preferably the strands are arranged to form a warp knit diamond or hexagonal net mesh.

Preferably the filaments comprise a plastics material for example polyester or polypropylene.

More preferably the filaments are absorbable. The mesh may be encapsulated by an absorbable or non absorbable coating or a coating may be applied to at least one side of the implant.

The surface material may be polylactic acid and the core material may be polypropylene.

The mesh may be formed from biocomponent microfibres comprising a core and surface material. The surface material may be readily absorbable by the body while the core material may remain in the body for a longer period of time.

The supporting zone of the implant may be absorbable at a different rate than the fixing zones of the implant, for example the supporting zone may be absorbed within six weeks of implantation, while the fixing zones may remain for 9 months.

Preferably the fixing zones remain in the body longer than the supporting zone.

The fixing zones are required to remain in the body until increases in intra-abdominal pressures, for example due to coughing, laughter, straining, sneezing or lifting a heavy object, are transmitted to the pressure compartment which includes the urethra such that the increased intra-abdominal pressure promotes occlusion of the urethra.

Preferably pressure transmission occurs when a pubourethral neoligament forms.

Generally formation of the pubourethral neoligament takes place in around 6-9 months.

Intra-abdominal pressure transmission to the pressure compartment which includes the urethra may be provided by suitable placement of anchor strips comprising fixing zones on either side of the urethra, such that when at least one anchor strip is suitably positioned on either side of the urethra, even although the anchor strip does not pass under the urethra and directly support the urethra using a supporting element, the anchor strip provides sufficient support to the urethra, by connecting the intra-abdominal pressure compartment and sub urethral pressure compartment such that increases in intra-abdominal pressures are transmitted to the urethra, promoting occlusion of the urethra during periods of increased intra-abdominal pressure.

According to a further aspect of the present invention there is provided at least one anchor strip comprising at least one fixing zone having at least one retaining means wherein in use a first portion of the anchor strip is retained in the tissues of the retropubic space above the endopelvic fascia and a second portion of the anchor strip extends into the urethral pressure compartment below the endopelvic fascia and thereby supports but does not pass under the urethra.

The sub urethral space is defined as a pressure compartment below the endopelvic fascia Preferably the anchor strips are between 2 cm and 8 cm in length.

More preferably the anchor strips are between 4 cm and 8 cm in length.

Most preferably the anchor strips are 6 cm in length.

The fixing zones of the anchor strip include retaining means as described herein.

Preferably the anchor strips comprise any of the Preferably the implant is of width 0.3 to 1.7 cm.

More preferably the implant is of width 0.5 cm to 1.5 cm.

Most preferably the implant is of width 1.0 cm to 1.1 cm.

Preferably the implant is of thickness 100 µm to 300 µm.

More preferably the implant is of thickness 200 µm.

Where the implant is reinforced, the material of the implant may be of double thickness. In reinforced areas of the implant the implant may be of thickness between 200 µm to 600 µm. More preferably the reinforced areas of the implant are of thickness 400 µm.

The implant is of suitable length such that a first fixing zone can be secured in the tissues of the retropubic space and the implant can extend from the tissues of the retropubic space, pass on one side of the urethra such that the supporting zone of the implant passes under the urethra and a second fixing zone passes on the other side of the urethra and into the tissues of the retropubic space, such that the second fixing zone can be secured in the tissues of the retropubic space. Preferably the fixing zones are positioned only as far into the tissues of the retropubic space as required such that pressure transmission occurs and the mid-urethra is occluded at periods of raised abdominal pressure such as coughing.

Typical cough pressures generated are around 0 to 150 cm water. Maximum cough pressures generated are 200 cm to 400 cm of water.

Thus during periods of raised abdominal pressure, such as coughing, the bladder and urethra are pushed downwards. The tape acts against this downward movement of the urethra supporting the urethra and causing the mid urethra to be occluded. This minimises incontinence. If the tape further comprises resilient zones, the resilient extension of the tape during periods of raised abdominal pressure cushions the urethra against the force subjected to the urethra by the tape, such that the urethra is supported in a more similar manner as provided by physiological tissues. However, the force subjected to the urethra by the tape comprising resilient means, still causes the mid urethra to be occluded at periods of raised abdominal pressure and minimises incontinence.

It is preferable that tissue growth around and through the implant occurs to integrate the implant into the body.

Fibroblastic through growth around the implant secures the implant in the body increasing the support provided by the implant.

Preferably at least one of the fixing zones of the implant is provided with means to improve fibroblastic through growth into the implant.

Preferably the means to improve fibroblastic through growth comprises pores which extend through the fixing zone material said pores ranging in width across the surface of the fixing zone from 50 µm to 200 µm.

More preferably the pores are a width of 100 µm.

Alternatively the means to improve fibroblastic through growth comprises pits, that indent at least one surface of the fixing zone, but do not extend through the fixing zone, the pits ranging from 50 to 200 µm in width.

More preferably the pits are 100 µm in width.

As a further alternative, the means to improve fibroblastic through growth comprise slits that extend through the fixing zone material said slits being 2 mm in length and 500 µm in width.

Preferably the slits are 1 mm in length and 100 µm in width.

More preferably the slits are 200 µm in length and 50 µm in width

Preferably the pits, pores or slits are distributed across the complete surface of at least one of the fixing zones.

Alternatively the pits, pores or slits are distributed only in a particular portion of the surface of at least one of the fixing zones.

Preferably the pits, pores or slits are created by post synthesis treatment of at least one of the fixing zones by a laser.

Alternatively the pits, pores or slits are created during synthesis of at least one of the fixing zones.

Where the fixing zone is comprised of plastics material the pits, pores or slits may be formed by the spaces of mono-filament between the waft and weave of mono-filament or multi-filament yarns when the filaments are woven to form a mesh.

Alternatively pits, pores or slits formed during the synthesis of plastics material are formed by the inter-filament spaces created when mono-filaments are twisted to create multi-filaments, the multi-filaments then being woven to form a mesh.

Preferably integration of the implant into the body via fibrous tissue through-growth begins to occur within one month of insertion of the implant in the body.

More preferably integration of the implant into the body via fibrous tissue through-growth begins to occur within two weeks of insertion of the implant in the body.

It is also advantageous that lay down of collagen fibres occurs in an ordered direction to promote the formation of at least one strong ordered neoligament. The formation of at least one ordered neoligament aids the support of the urethra provided by the implant by adding mechanical strength to tissue which forms around the implant.

Preferably at least one of the fixing zones is provided with at least one microgroove on at least one surface of the fixing zone.

Preferably at least one of the fixing zones is provided with a plurality of microgrooves on at least one surface of the fixing zone.

Preferably a microgroove is of width between 0.5 µm to 7 µm and of depth 0.25 µm to 7 µm.

More preferably a microgroove is 5 µm in width and 5 µm in depth.

Preferably the plurality of microgrooves are aligned such that they are substantially parallel with each other.

Preferably the plurality of microgrooves are aligned such that they are separated by ridges which range in size between 1 µm to 5 µm in width.

More preferably the microgrooves are separated by ridges of 5 µm in width.

Preferably the ridges are formed by square pillars and the base of the microgroove is substantially perpendicular to the square pillars.

Alternatively the ridges are formed by square pillars and the base of the microgroove is bevelled in relation to the pillars.

Preferably the microgrooves are present on at least one surface of the fixing zone.

More preferably the microgrooves are present on a plurality of surfaces of the fixing zone.

Preferably the supporting zone of the implant does not comprise pores or pits.

Preferably only the surfaces of the supporting zone not brought into contact with the urethra comprise microgrooves.

The supporting zone is not provided with pores or pits to discourage the formation of peri-urethral adhesions.

Preferably at least one fixing zone is capable of being moved in and out of the tissues of the retropubic space by a surgeon.

Preferably movement of the fixing zone into and out of the tissues of the retropubic space allows adjustment of the location of the supporting zone such that it passes under the urethra.

Preferably the supporting zone comprises a marker to aid the suitable location of the supporting zone under the urethra.

More preferably the marker is a wider portion of tape of the supporting zone that indicates the midpoint of the supporting zone.

The tape may comprise a reinforced portion. This is advantageous as it allows the bulk of the tape to be formed from a minimal mass of material. Regions of the tape which require tensile strength can be then strengthened appropriately.

Preferably the spine of the tape running along the longitudinal axis can be reinforced.

Reinforcing may be provided by using a double thickness of material.

Preferably each fixing zone comprises at least one aperture adapted to receive and co-operate with a tool for insertion of the implant into the body.

Preferably the tape surrounding the aperture is of double thickness. This is advantageous as it provides additional strength to the tape in this region.

More preferably the aperture is bound by ultrasonic welding.

Preferably the aperture is located towards the end of the fixing zone furthest from the supporting zone.

Preferably the implant is used to support the urethra.

Preferably the implant is used for treating urinary incontinence or uterovaginal prolapse.

The invention also provides a tool for inserting the implant into the body the tool comprising an elongate shaft including a semi-blunt point at a first end and a handle at a second end and holding means to releasably attach the shaft to the implant.

Preferably the tool can be used to insert implants comprising a supporting zone or anchor strips.

Preferably the elongate shaft is curved or bent, through an angle of approximately 30°

Preferably the elongate shaft of the tool is of length 6 to 15 cm.

More preferably the elongate shaft of the tool is 8 cm in length.

Preferably the elongate shaft of the tool is between 2-3 mm in diameter.

Preferably the holding means comprises a recess extending from the semi-blunt point of the elongate shaft the recess capable of receiving a portion of the implant.

The point of elongate shaft comprising the recess may be offset such that a first portion forming a wall of the recess is longer than a second portion forming the opposite wall of the recess. This is advantageous as the longer portion of the shaft on one side of the recess aids mounting of the tape on the tool.

Preferably the recess is angled to twist an implant received by the recess along its longitudinal length such that the longitudinal edges of the fixing zone of the implant are directed away from the bladder.

Twisting of the implant such that the edges of the fixing zone are directed away from the bladder minimises medial presentation of the retaining means to the bladder.

Alternatively the holding means comprises an abutment located toward the first end of the elongate shaft of the tool wherein the semi-blunt point of the elongate shaft is capable of being passed through the implant and the abutment is capable of hindering movement of the implant down the length of the shaft toward the second end of the elongate shaft.

Preferably the tool is comprised of plastics material.

Alternatively the tool is comprised of surgical steel.

Preferably the handle is circular in shape and is mounted perpendicular to the curvature at the second end of the elongate shaft.

According to a further aspect of the present invention there is provided a method of supporting the urethra comprising the steps of;

introducing an implant into a least one incision made on the upper wall of the vagina, inserting a first end of the implant behind the first side of the urethra, locating a first fixing zone into the tissues of the retropubic space without penetrating the rectus sheath, inserting a second end of the implant behind a second side of the urethra, and locating a second fixing zone into the tissues of the retropubic space without penetrating the rectus sheath, such that the supporting zone passes under the urethra.

Preferably the ends of the implant are located in the retropubic space above the endopelvic fascia.

Preferably the method further includes the step of moving the retaining means from an inserting position to a retaining position.

Preferably the method of supporting the urethra is used in treating urinary incontinence or uterovaginal prolapse.

According to a further aspect of present invention there is provided a method of transmitting intra-abdominal pressure to the urethra comprising the steps of introducing an anchor strip into at least one incision made on the upper wall of the vagina;

inserting a first portion of the anchor strip behind the first side of the urethra;

locating a first portion including a fixing zone into the tissues of the retropubic space above the endopelvic fascia without penetrating the rectus sheath;

locating a second portion of the anchor strip alongside the urethra in the suburethral pressure compartment below the endopelvic fascia inserting a second anchor strip behind a second side of the urethra;

locating a first portion including a fixing zone of the second anchor strip into the tissues of the retropubic space without penetrating the rectus sheath; and locating a second portion of the second anchor strip along side the urethra in the suburethral pressure compartment below the endopelvic fascia.

Preferably at least one anchor strip is introduced through two small incisions.

Preferably the method further includes the step of moving retaining means from an inserting position to a retaining position.

Preferably the anchoring strip is used to treat urinary incontinence or uterovaginal prolapse.

Preferably the method of enabling transmission of the intra-abdominal pressure to the urethra is used in treating urinary incontinence or uterovaginal prolapse.

III.

This invention relates to an apparatus and method for treating female urinary incontinence and, in particular, to a surgical implant having a sling that passes under the urethra in use and supports the urethra to alleviate incontinence, along with related apparatus and methods for inserting the surgical implant in the body.

Urinary incontinence affects a large number of women and, consequently, various approaches have been developed to treat female urinary incontinence. Those skilled in the art will be familiar with approaches ranging from pelvic floor exercises to surgical techniques such as Burch colposuspension and Stamey-type endoscopic procedures in which the sutures are placed so as to elevate the bladder neck.

This invention is particularly directed to improvement of a known procedure in which a sling is positioned loosely under the urethra, commonly known as TVT (tension free vaginal tape) and described, for example, in International Patent Applications No. WO97/13465 and WO97/06567. It is generally understood that this treatment alleviates urinary incontinence by occluding the mid-urethra (for example at a time of raised abdominal pressure by coughing or the like).

The sling is provided in the body using two large curved needles which are provided at each end of the sling, which sling comprises a long mesh or tape. Each of the needles is carried on an insertion tool (which is basically a handle facilitating manipulation of the needles). The mesh or tape is usually made of knitted polypropylene (such as Prolene®). The mesh or tape is generally covered with a plastics sleeve or polyethene envelope to aid smooth insertion, the mesh or tape having rough surfaces to aid retention in the body.

An incision is made in the anterior vaginal wall and the first of the needles is passed through the incision, past one side of the urethra, behind the pubic bone, through the rectus sheath and out through the lower anterior abdominal wall. Likewise, the second needle is passed through the incision, past the other side of the urethra, behind the pubic bone, through the rectus sheath and out through the lower abdominal wall. The needles are separated from their respective insertion tools and also from the mesh or tape such that only the tape and its plastics sleeve are left in the body, passing from a first exit point in the lower abdominal wall, through the rectus sheath, behind the pubic bone, under the urethra, back behind the pubic bone, back through the rectus sheath and out through a second exit point in the lower abdominal wall.

The plastics sleeve is then removed from the tape and the tape adjusted to a suitable tension (such that the tape provides a sling that passes loosely under the urethra, as described above) by maneuvering the free ends of the tape outside the exit points in the lower abdominal wall whilst the urethra is held using a rigid catheter inserted therein. The tape is then cut such that it just falls short of protruding from the exit points in the lower abdominal wall. The exit points and the incision in the upper vaginal wall are then closed by sutures. The tape is held in position by virtue of friction between the tape's rough edges and the surrounding body tissue (such as the rectus sheath and the body tissue behind the pubic bone) and subsequent natural adhesion of the tape with the body tissue as it re-grows around the mesh material. Whilst highly effective in treating urinary incontinence, this procedure has a number of problems. One such problem is that the needles used for inserting the tape are comparatively large, with the needles having, for example, a diameter of around 5-6 mm and a length of around 200 mm. As well as causing concern for patients viewing such needles before or during the procedure (which is carried out under local anaesthetic), this can also lead to a high vascular injury rate.

Similarly, the requirement that the needles exit the lower abdominal wall is disadvantageous due to the trauma to the patient in this area and pain of such abdominal wounds. A further disadvantage is that the tape comprises a relatively large foreign body mass to be retained within the patient and this can lead to related inflammation, infection translocation, erosion, fistula and such like.

Similarly, the nature of the large needles and tape, along with the tools required to insert these in the body, lead to the procedure having a relatively high cost.

According to a first aspect of the present invention there is provided a surgical implant for supporting the urethra, the implant comprising: a suburethral support suspended between at least two soft tissue anchors attached at either side of the suburethral support, each soft tissue anchor having retaining means for retaining each anchor in tissue and suspending means for suspending each side of the suburethral support from a soft tissue anchor such that the suburethral support passes under the urethra in use.

Preferably the retaining means of the soft tissue anchor is capable of being inserted into soft tissue or fascia from an incision in the upper vaginal wall without the need to penetrate the lower abdominal wall.

In one embodiment the soft tissue anchor is insertable into the rectus sheath of the human or animal body to anchor suspending means to the soft tissue, the suspending means being attached to the soft tissue anchor and the soft tissue anchor having retaining means adapted to prevent retraction of the anchor from the rectus sheath in a direction opposite to that of insertion of the anchor into the tissue.

Preferably the soft tissue anchor comprises a central portion and the retaining means includes at least one wing section, the wing section being mounted on a first end of the central portion by resilient hinge means such that the wing section is moveable between an open, resting position and a deflected position such that in use, when the soft tissue anchor device is inserted into the tissue the wing section is pushed or held towards the central portion to a deflected position to permit entry of the soft tissue anchor into the tissue and through the rectus sheath, wherein the wing section returns to its open or resting position and prevents the soft tissue being removed.

Preferably the resilient hinge means allows the wing section to return to its resting position from its deflected position following penetration of the soft tissue anchor through the rectus sheath such that the wings of the soft tissue anchor once pushed through the rectus sheath can rest on the surface of the rectus sheath fascia opposite to the surface through which the soft tissue anchor is inserted and thus the soft tissue anchor cannot be retracted.

Preferably the resilient hinge means is capable of preventing the wing section being moved to a position greater than substantially perpendicular to the central portion.

Preferably the central portion of the soft tissue anchor comprises a hollow passage which extends from a first end of the central portion to a second opposite end of the central portion.

Preferably an introducing tool can be placed into the hollow passage such that the introducing tool extends through the central portion the soft tissue anchor such that the introducing tool extends to a point beyond the first end of the central portion.

Preferably the soft tissue anchor comprises a plurality of wing sections.

More preferably the soft tissue anchor comprises four wing sections arranged radially around the first end of the central portion.

Preferably the soft tissue anchor in addition to comprising a central portion and a wing section also comprises at least one stud element arranged radially around the first end of the central portion, the stud having an inclined face in the opposite direction to that in which the soft tissue anchor is inserted to aid separation of the tissue during entry of the soft tissue anchor enabling easier passage of the soft tissue anchor through the soft tissue.

Preferably the soft tissue anchor does not comprise a sharp point.

In an alternative embodiment the soft tissue anchor is capable of anchoring in the retropubic tissue space without penetrating the rectus sheath.

Preferably the soft tissue anchor in this embodiment permits fixation at multiple points via a Christmas tree type configuration of deflectable wings.

A soft tissue anchor according to this embodiment comprises a central portion and the retaining means includes a plurality of projections the projections extending radially from the central portion along a substantial portion of the length of the central portion allowing fixation at a plurality of layers. Preferably the projections extend radially from the central portion at an angle inclined toward the second end of the central portion.

Preferably the projections are of a shape that they are able to provide additive traction to the soft tissue anchor and allow it to grip fibro-fatty soft tissue and blood vessels of the paraurethral tunnel below the level of the rectus sheath.

In yet a further embodiment the soft tissue anchor may comprise a substantially flat head the bottom surface nearest the suspending means of the flat head providing the retaining means which, in use is held in the rectus sheath.

In a further embodiment the soft tissue anchor may comprise a sharp point allowing it to pierce or penetrate the rectus sheath, and retaining means comprising a surface or protrusion directed rearwardly with respect to the sharp point which does not cause the soft tissue to part and thus prevents the soft tissue anchor from being pulled back out through the rectus sheath soft tissue in the direction opposite to that in which it is inserted into the soft tissue.

Preferably the sharp point is provided by the apex of a conical head portion and retaining means are provided by a substantially flat base of the conical head.

In any embodiment the soft tissue anchor is comprised of plastics material.

Typically the soft tissue anchor is comprised of polypropylene.

Alternatively the soft tissue anchor is comprised of absorbable material so as to form temporary fixation in soft tissue.

The soft tissue anchor may comprise a point formed of absorbable material including polyglactin, the sharp point thus capable of facilitating insertion of the anchor, yet being absorbed by the body later.

Preferably the soft tissue anchor may be integral with the suspending means.

More preferably the soft tissue anchor is integrally formed from polypropylene or other polymeric material the attachment between the anchor and the suspending being formed as a single unit.

An integral construction of the soft tissue anchor and suspending means has the advantage of simplifying the construction of the soft tissue anchor and suspending means, which can reduce the possibility of defective manufacture etc. and reduce costs and the chance of the soft tissue anchor and suspending means becoming detached once implanted in the body.

Alternatively the soft tissue anchor is attached to the suspending means by a thin metal tube crimped or otherwise attached around the suspending means and central portion of the soft tissue anchor.

The suburethral support of the first aspect of the invention passes under the urethra, loosely supporting the urethra, the suburethral support being held in position by suspending means attached to each of its free ends on either side of the urethra, the suspending means being attached at the opposite end to at least one soft tissue anchor.

Preferably the suburethral support is comprised of flat polymer tape.

Preferably the suburethral support has dimensions sufficient only to pass around the urethra.

More preferably the suburethral support has dimensions of length 15-35 mm, width 5-15 mm and thickness 50-350 mm.

In one embodiment the suburethral support has dimensions of length 25 mm, width 10 mm and thickness 100 mm.

Preferably the suburethral support has at least two junctions to attach the suburethral support to the suspending means.

One problem with the preferred arrangement of a soft tissue anchor and suspending means for suspending the suburethral support of the surgical implant of the invention is that it is difficult to predetermine what length the suspending means must be to position the suburethral support loosely under the urethra as desired.

This is because the distance between the rectus sheath in which the soft tissue anchor is inserted and the urethra varies from patient to patient.

Preferably the distance between the soft tissue anchor(s) and the suburethral support is adjustable.

More preferably the soft tissue anchor (or anchors) can be positioned first and the suburethral support then positioned by adjusting the length of the suspending means.

Preferably the suburethral support is provided with at least one attachment tab to which suspending means are releasably or permanently attached.

Preferably the suburethral support comprises an attachment tab comprising a tunnelled element and an aperture, the tunnelled element being located at each of the free ends of the suburethral support on either side of the urethra at a position that the suspending means are capable of being introduced through, the tunnelled element co-operating with the aperture such that suspending means can be passed through the tunnelled element and then through the aperture, the aperture being present on the opposite surface of the suburethral support to that which contacts the urethra the aperture having an edge capable of co-operating with a ring element and the ring element being capable of being fitted around the aperture trapping the suspending means between the ring element and the edge of the aperture such that the suspending means remain fixed in an adjusted position wherein the suburethra support hanging loosely under the urethra.

Alternatively the attachment tab comprises at least one slot through which suspending means can be passed, the suspending means being permanently attached to the slot by tying.

Alternatively the attachment tab comprises jamming slots that the suspending means can be permanently attached by being threaded through the jamming slots such that the suspending means are held in an adjusted position.

Alternatively the suburethral support is capable of being suitably positioned under the urethra by altering the position of the soft tissue anchors within the body such that at least one soft tissue anchor is secured in the soft tissue or in the rectus sheath and a subsequent anchor is inserted into the soft tissue or rectus sheath to a suitable depth such that the suburethral support hangs loosely under the urethra.

Alternatively the suspending means may be attached to the suburethral support by healing such that the suburethra support and/or suspending means melt and form a join.

Alternatively the attachment tabs may have closure means for gripping the suspending means.

The suspending means may be any means suitable for connecting each end of the suburethra support to the soft tissue anchor (or respective soft tissue anchors).

Preferably the suspending means comprises a plastics strip.

Preferably the plastics strip has smooth edges. Preferably the plastics strip comprises material such as polypropylene or other suitable non-absorbable or absorbable polymer tape.

Preferably the plastics strip is 3-5 mm in width.

Preferably the plastics material comprises pores which extend through the plastics material from a first surface of the plastics material to a second opposite surface of the plastics material said pores ranging in width across the surface of the plastics material from 50 µm to 200 µm, the pores allowing tissue in-growth to secure the strip in the body.

Alternatively the plastics material may comprise pits, that indent but do not extend through the plastics material, on at least one of the surfaces of the plastics material, the pits ranging in width from 50 µm to 200 µm, the pits allowing tissue in-growth to secure the strip in the body.

Preferably the plastics material comprises pits or pores ranging in width across the surface of the plastics material from 100 µm to 150 µm.

Preferably the pits or pores are distributed across the complete surface of the plastics material.

Alternatively the pits or pores are distributed only in a particular portion of the surface of the plastics material.

Preferably the pits or pores are created by post synthesis modification of the plastics material.

More preferably the pits or pores are created by post synthesis treatment of the plastics material by a laser.

Alternatively the pits or pores of between 50-200 µm are created during synthesis of the plastics material by spaces between the waft and weave of mono-filament or multi-filament yarns when the filaments are woven to form a mesh.

Alternatively pits or pores formed during the synthesis of plastics material are formed by the inter-filament spaces created when mono-filaments are twisted to create multi-filaments, the multi-filaments then being woven to form a mesh.

In an embodiment the suspending means is provided with a plurality of microgrooves of width between 0.5-7 µm and of depth 0.25-7 µm on at least one surface of the plastics strip.

Preferably the microgrooves are 5 µm in width and 5 µm in depth.

Preferably the plurality of microgrooves are aligned such that they are substantially parallel with each other.

Preferably the plurality of microgrooves are aligned such that they are separated by ridges which range in size between 1-5 µm in width.

More preferably the microgrooves are separated by ridges of 5 µm in width.

Preferably the ridges are formed by square pillars and the base of the microgroove is substantially perpendicular to the square pillars.

Alternatively the ridges are formed by square pillars and the base of the microgroove is bevelled in relation to the pillars.

Preferably the microgrooves are present on at least one surface of the suspending means.

More preferably the microgrooves are present on a plurality of surfaces of the suspending means.

These microgrooves act to orientate and align the proliferating fibroblasts on the surface of the plastics material and cause axial alignment of collagen fibres and formation of at least one strong ordered neoligament.

The orientation and alignment of the proliferating cells is capable of adding mechanical strength to the tissue which forms around the plastics material such that it is more able to support the urethra.

Preferably the suburethral support of the present invention has neither pores, pits or grooves to discourage the formation of peri-urethral adhesions.

According to a second aspect of the present invention there is provided a method of supporting the urethra comprising the steps of, introducing a surgical implant as described above into an incision made on the upper wall of the vagina, inserting a soft tissue anchor on a first side of the urethra behind the pubic bone, inserting a second soft tissue anchor on a second side of the urethra behind the pubic bone, such that the suburethral support is suspended from the soft tissue anchor supports the urethra.

The invention also provides the use of the method of supporting the urethra in treating urinary incontinence or uterovaginal prolapse.

In one embodiment of the method the soft tissue anchors are inserted in the rectus sheath.

In an alternative embodiment of the method the soft tissue anchors are inserted in the fibro-fatty soft tissue of the retro-pubic tissue space and do not penetrate the rectus sheath.

The invention also provides an introducing tool comprising an elongate housing adapted to receive the soft tissue anchor at one end and a point which is capable of extending through the central portion of a soft tissue anchor for use in carrying out the method of the invention such that the introducing tool enables access and placement of the soft tissue anchor through the rectus sheath or in the fibrous fatty soft tissue of the para-urethral tunnel from an insertion point in the upper vaginal wall.

More preferably the elongate housing is curved or bent, preferably through an angle of approximately 30°

It is desirable such that a sharp point of an anchor not is not retained in the body that the soft tissue anchor may be inserted using an introducing tool the introducing tool having a sharp point for penetrating the soft tissue.

Preferably an introducing tool comprises a sharp point for piercing or penetrating soft tissue and carrying means for carrying the soft tissue anchor to insert the anchor into the tissue such that the soft tissue anchor device does not require a sharp head and no sharp point is left in the body.

The overall size of the soft tissue anchor and introducing tool may be significantly smaller than that of the needles of the prior art.

Preferably the introducing tool may have a diameter of around 2 mm to 4 mm.

Preferably if the introducing tool is to be used in co-operation with a soft tissue anchor comprising a plurality of projections extending radially from the central portion along a substantial portion of the length of the central portion of the soft tissue anchor, the introducing tool comprises containment means for radially confining the plurality of projections extending from the central portion of the soft tissue anchor during the insertion of the soft tissue anchor.

Thus, when the soft tissue anchor has been inserted, the tool may release the retaining means around the soft tissue anchor such that the projections which have memory are biased to expand radially and grip the soft tissue.

The reduced size of the introducing tool in comparison to the needles used to introduce devices of the prior art can significantly reduce the vascular injury rate and perceptual problems of the prior art for a patient.

Preferably the introducing tool is able or has means for releasably retaining the soft tissue anchor on the end of the housing.

During the insertion of a surgical implant to support the urethra there is a risk of penetration of the bladder wall by the needles during insertion of the tape.

This is known to be a problem with the TVT procedure described by the prior art where the needles are inserted through an incision in the vagina to thread the tape through the respective punctures in the lower anterior abdominal wall.

Following the TVT procedure of the prior art it is therefore conventional to carry out cystoscopy after the tape has been inserted in the body to determine whether or not the bladder has been perforated. This is painful for the patient and also increases the duration of the operation.

The reduced size of the tools used for inserting the surgical implant of the present invention reduce to some degree the risk of the bladder being perforated during the surgical procedure, however it is nevertheless desirable to reduce the need for cystoscopy.

Accordingly at least a part of the surgical implant of the present invention may be coated or impregnated with a water soluble dye.

Preferably the soft tissue anchor of the present invention is impregnated with a water soluble dye.

Preferably, the water soluble dye is methylene blue.

It is possible to determine whether or not the bladder of a patient has been perforated by a surgical implant or instrument when inserting the surgical implant of the invention into the body, by expelling a small amount of fluid from the bladder, and determining whether or not this small amount of fluid contains any dissolved dye.

Should the bladder be perforated on insertion and placement of the surgical implant into the body, the dye impregnated into the surgical implant will dissolve in the fluid contained in the bladder and diffuse naturally throughout the fluid.

Thus should dye be present in the fluid, it is very likely that the bladder has been perforated and cystoscopy should be carried out. If there is no dye in the fluid, the bladder has not been perforated and the need for cystoscopy is obviated.

The soft tissue anchors as described in relation to the implant of the present invention are capable of use in a variety of situations.

Accordingly the invention provides soft tissue anchors as described herein.

The invention also provides the use of the soft tissue anchors in hernia repair, face lifts, plastic surgery and cosmetic surgery.

BRIEF DESCRIPTION OF THE DRAWINGS

The above and further advantages of the invention may be better understood by referring to the following description in conjunction with the accompanying drawings in which.

II.

Figure 30:
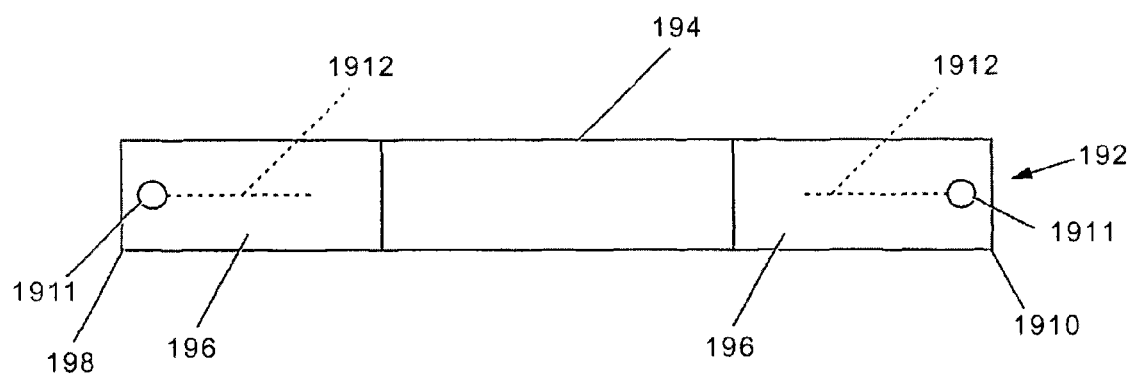
Figure 31:
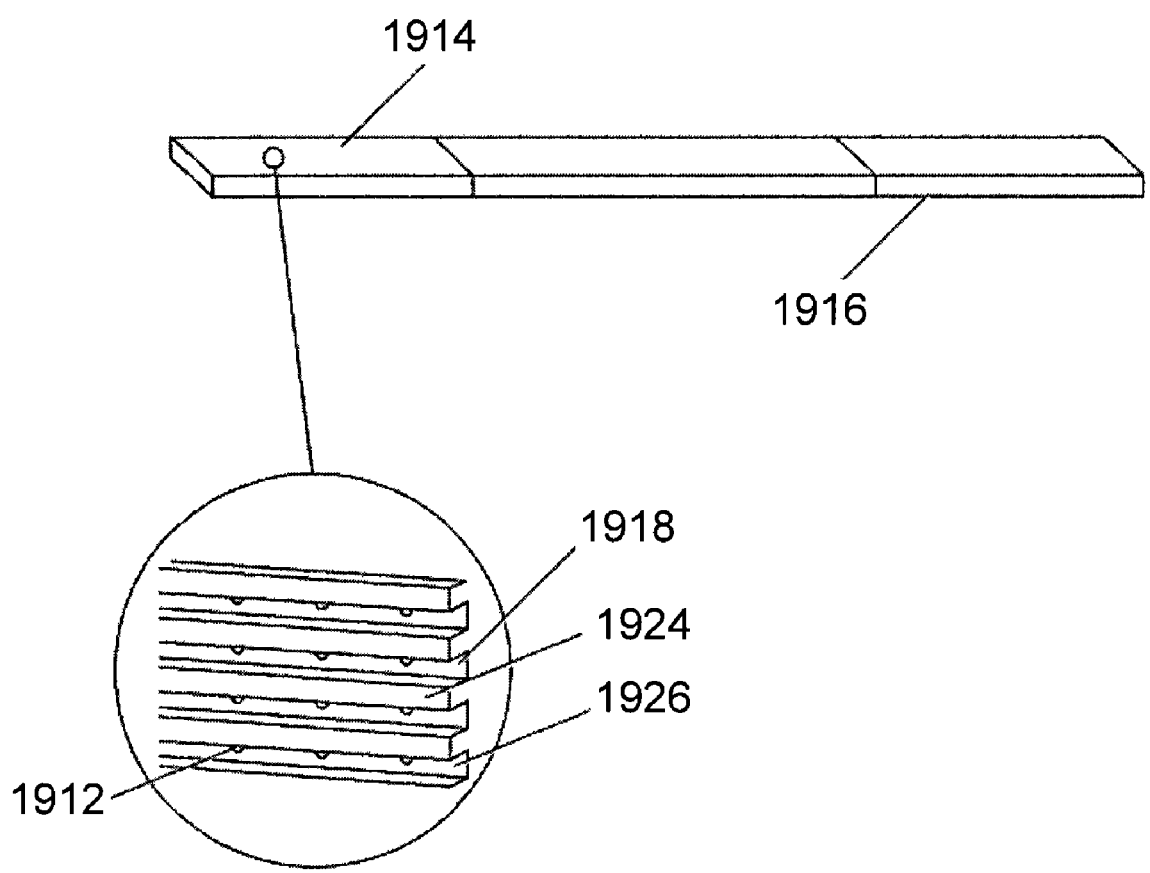
Figure 32A:
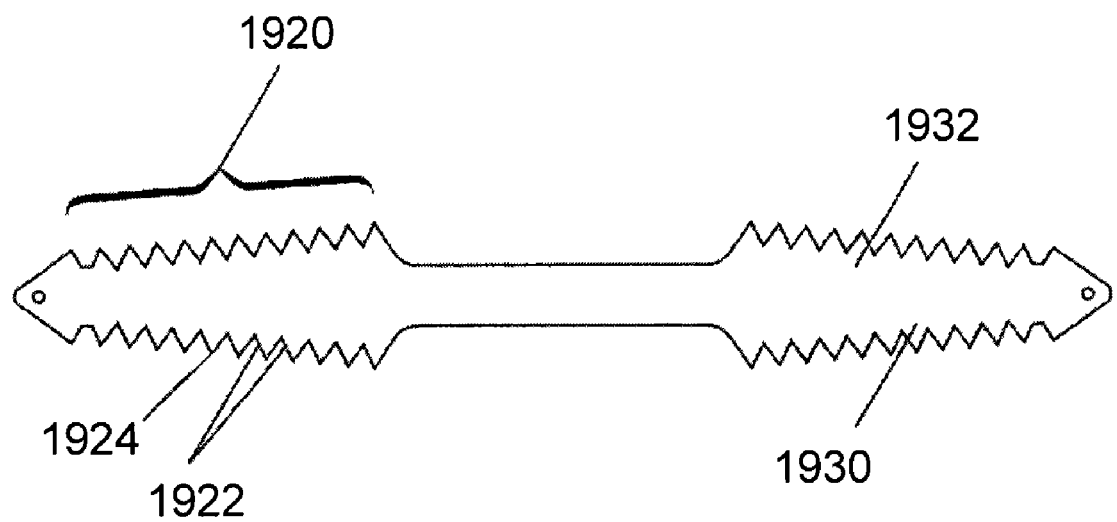
Figure 32B:
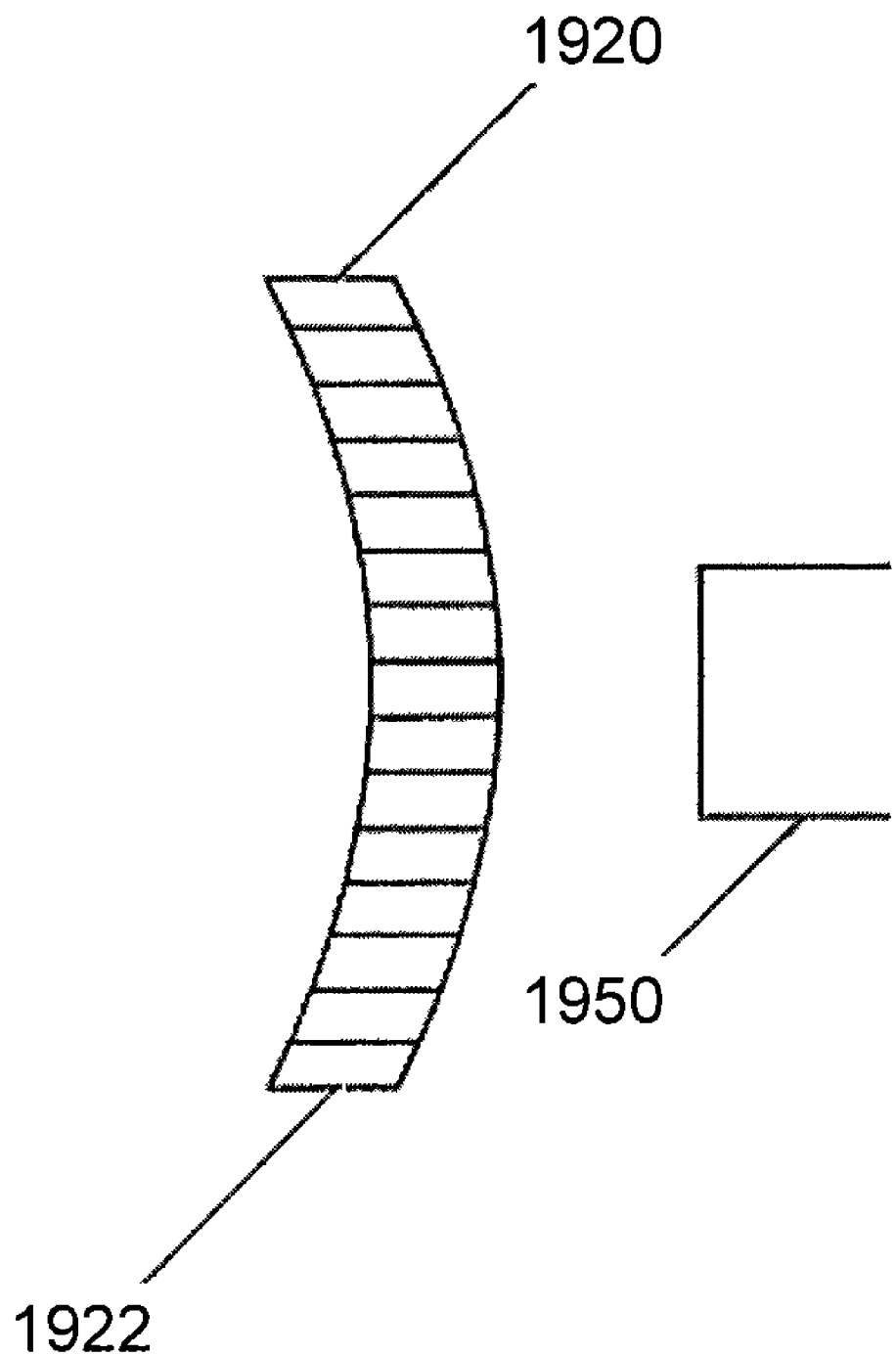
Figure 32C:
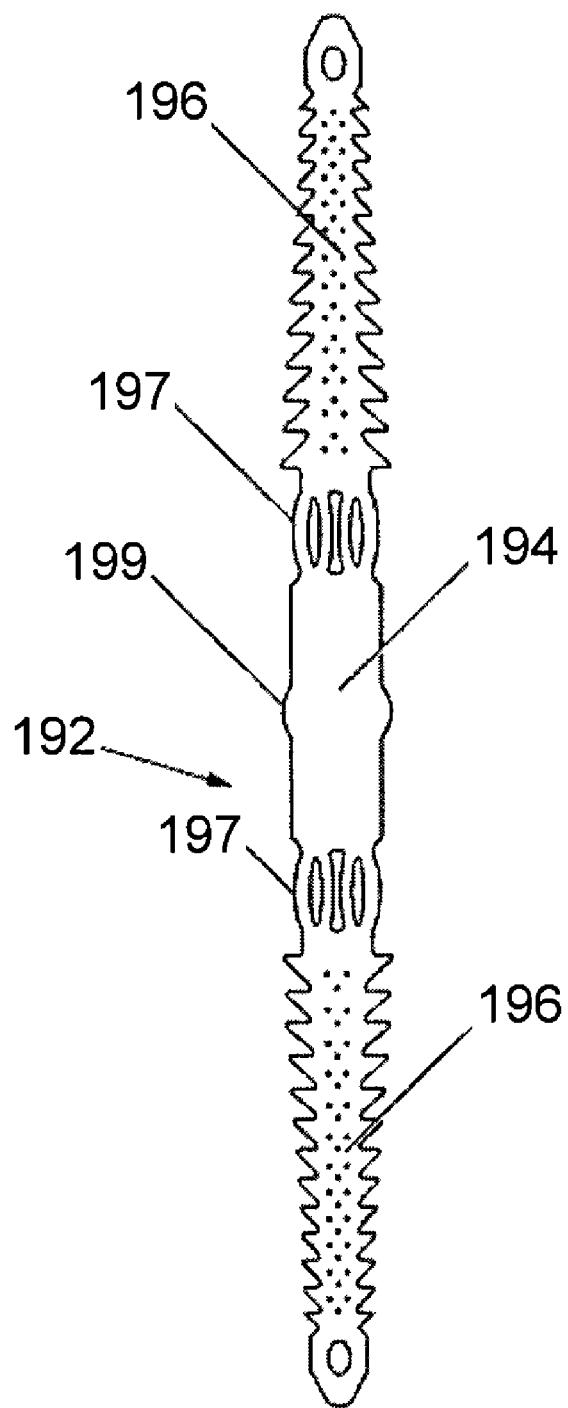
Figures 33A, 33B:
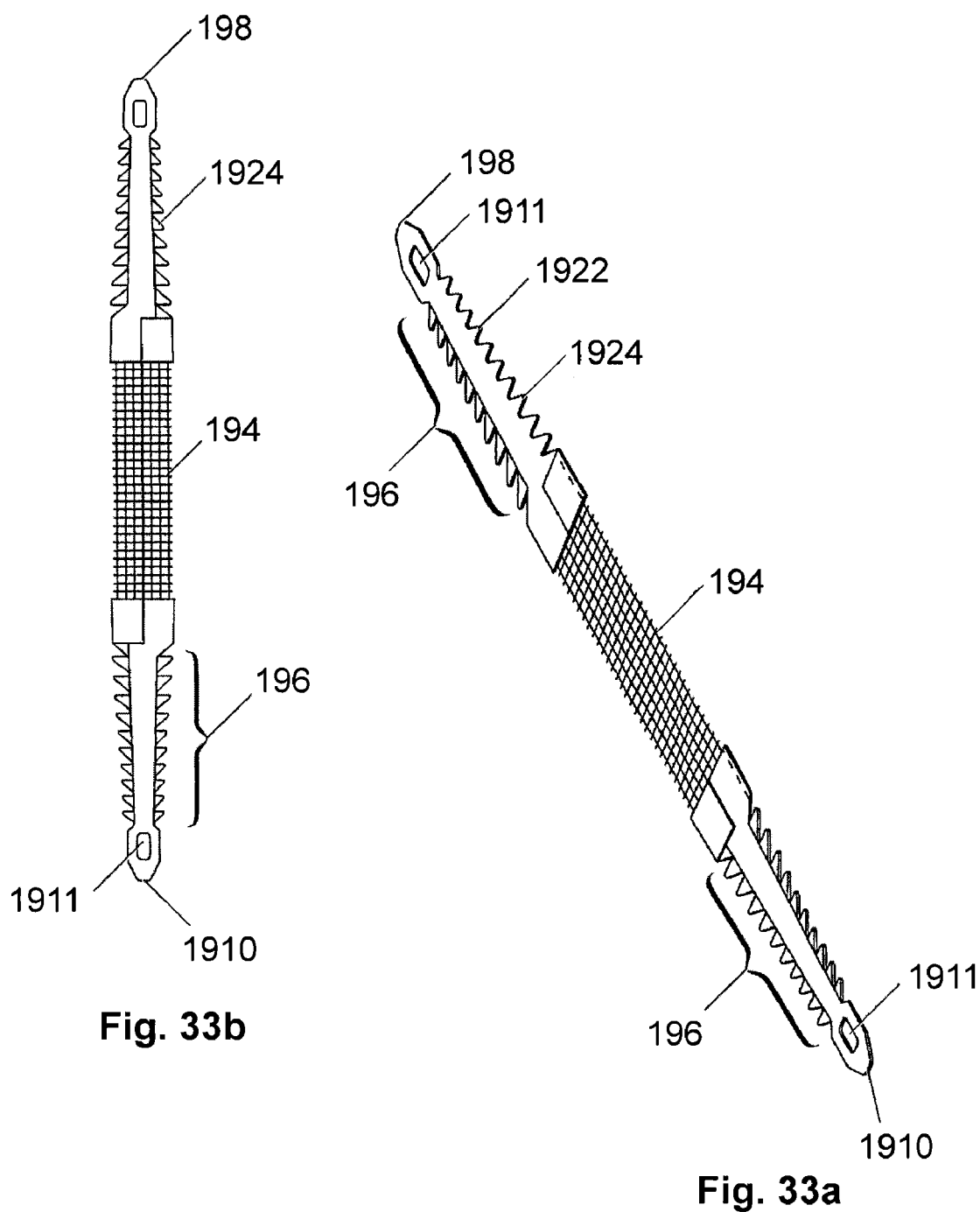
Figure 34:
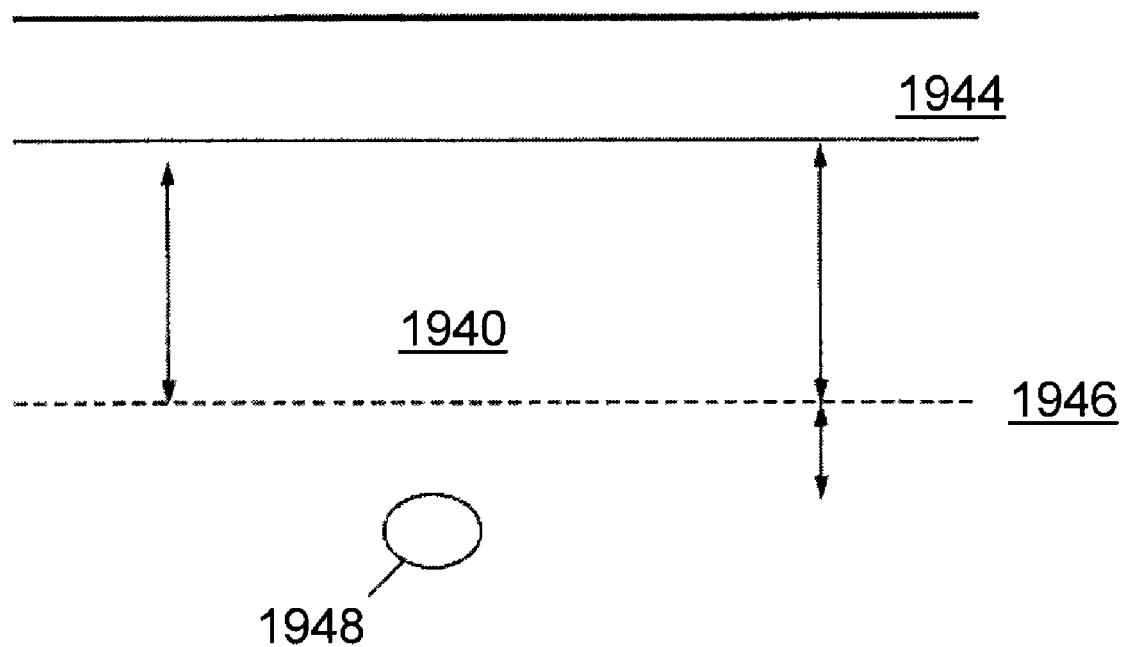
Figure 35:
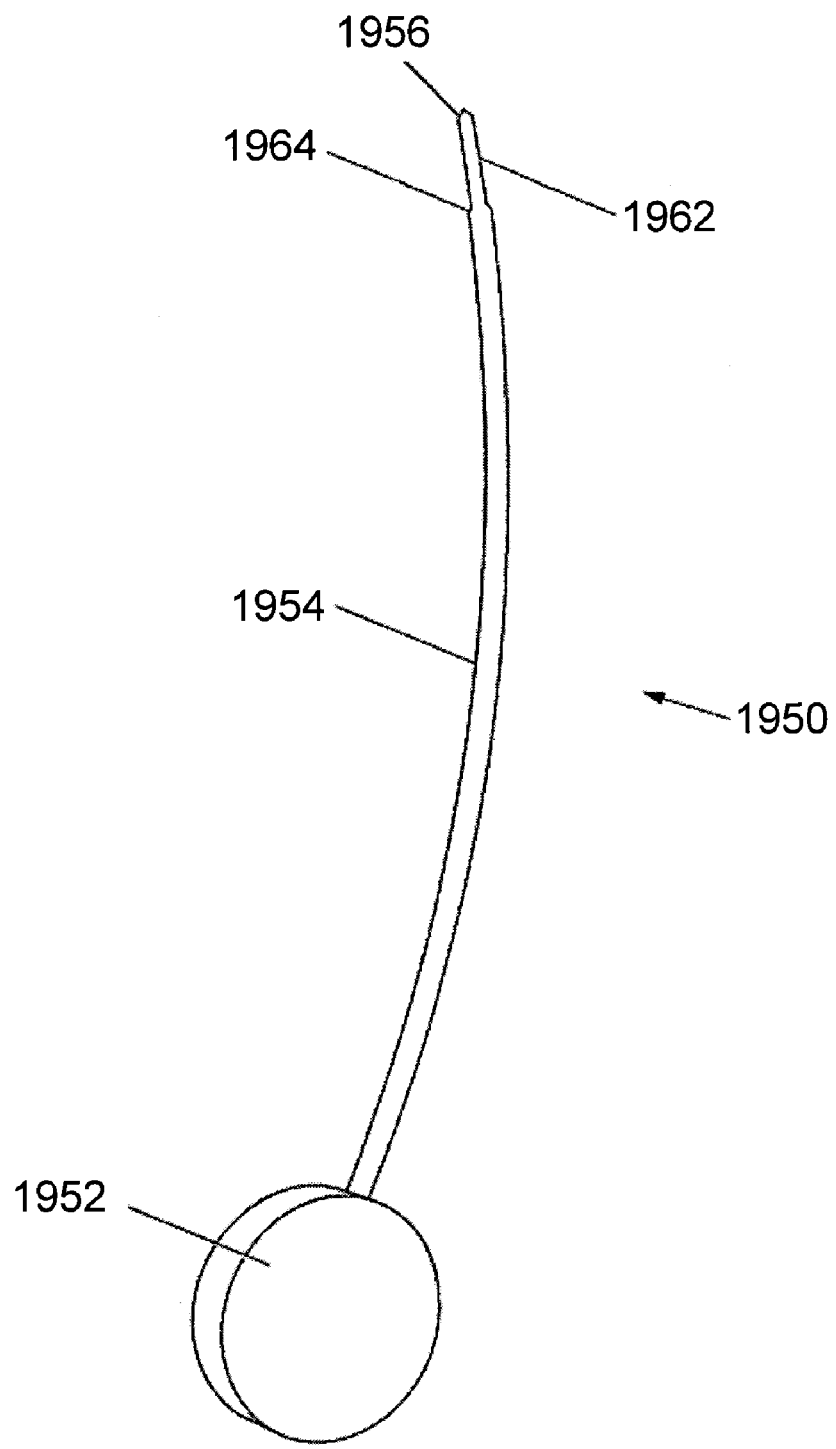
Figure 36A:
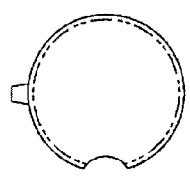
Figure 36B:
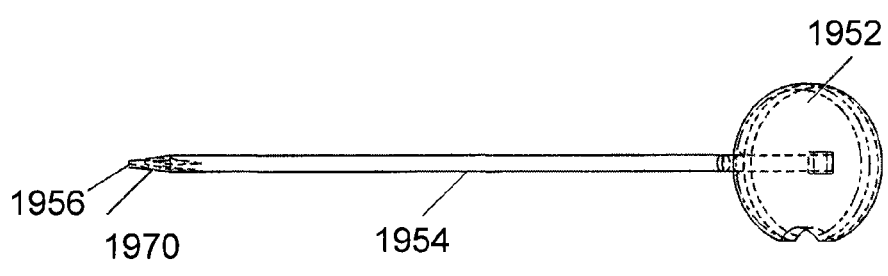
Figure 36C:
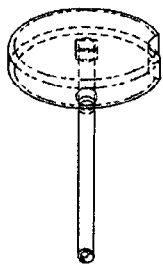
Figure 36D:
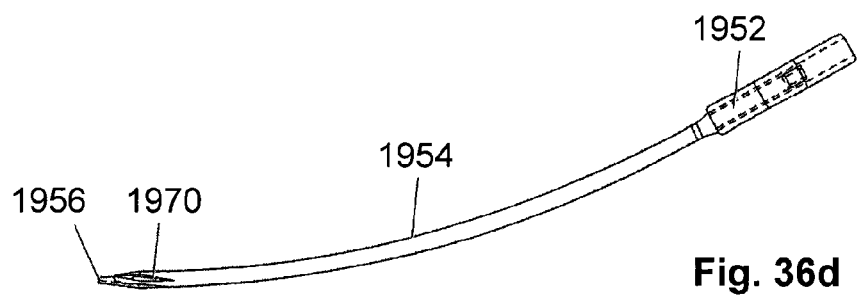
Figure 37:
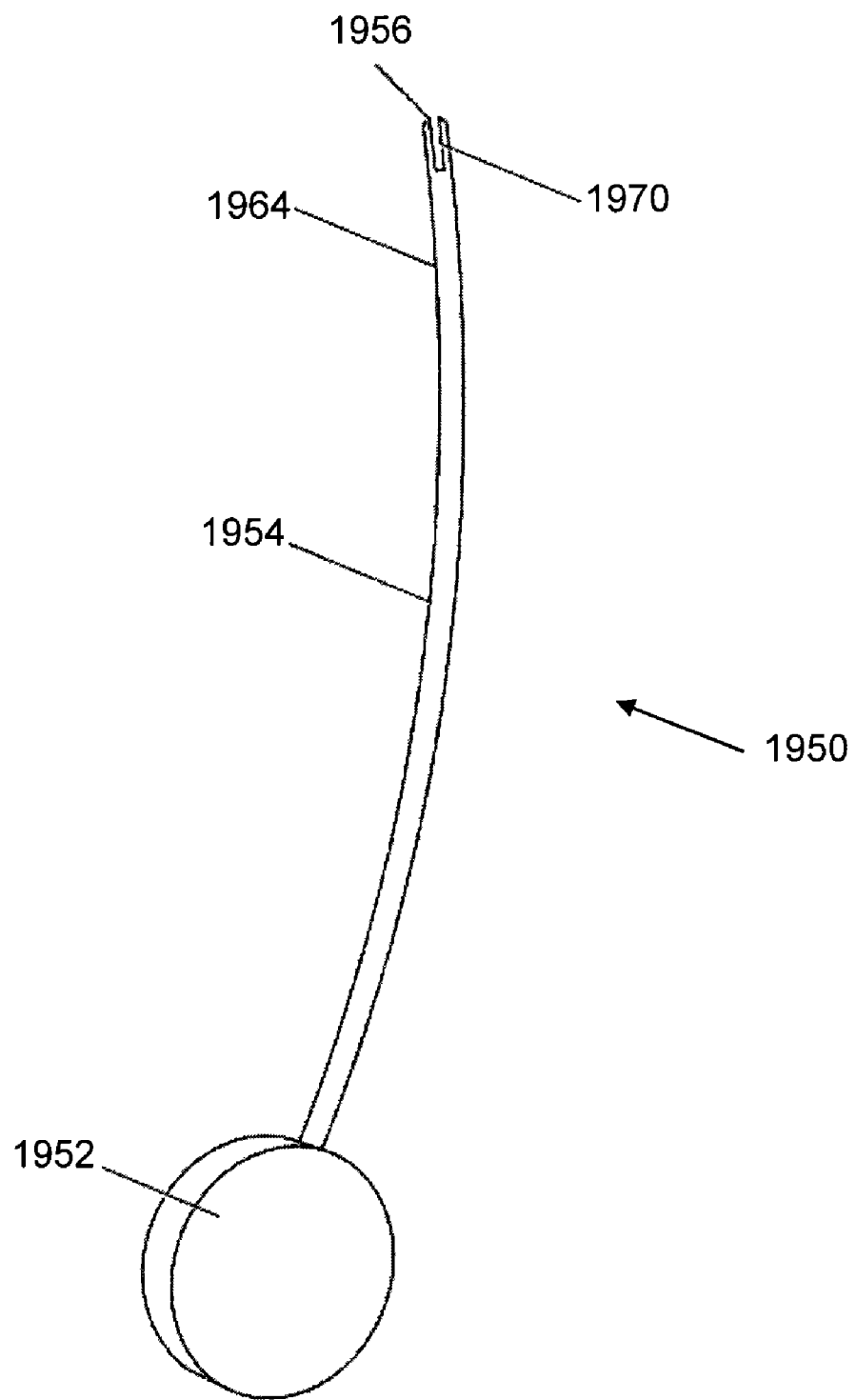
Figure 38:
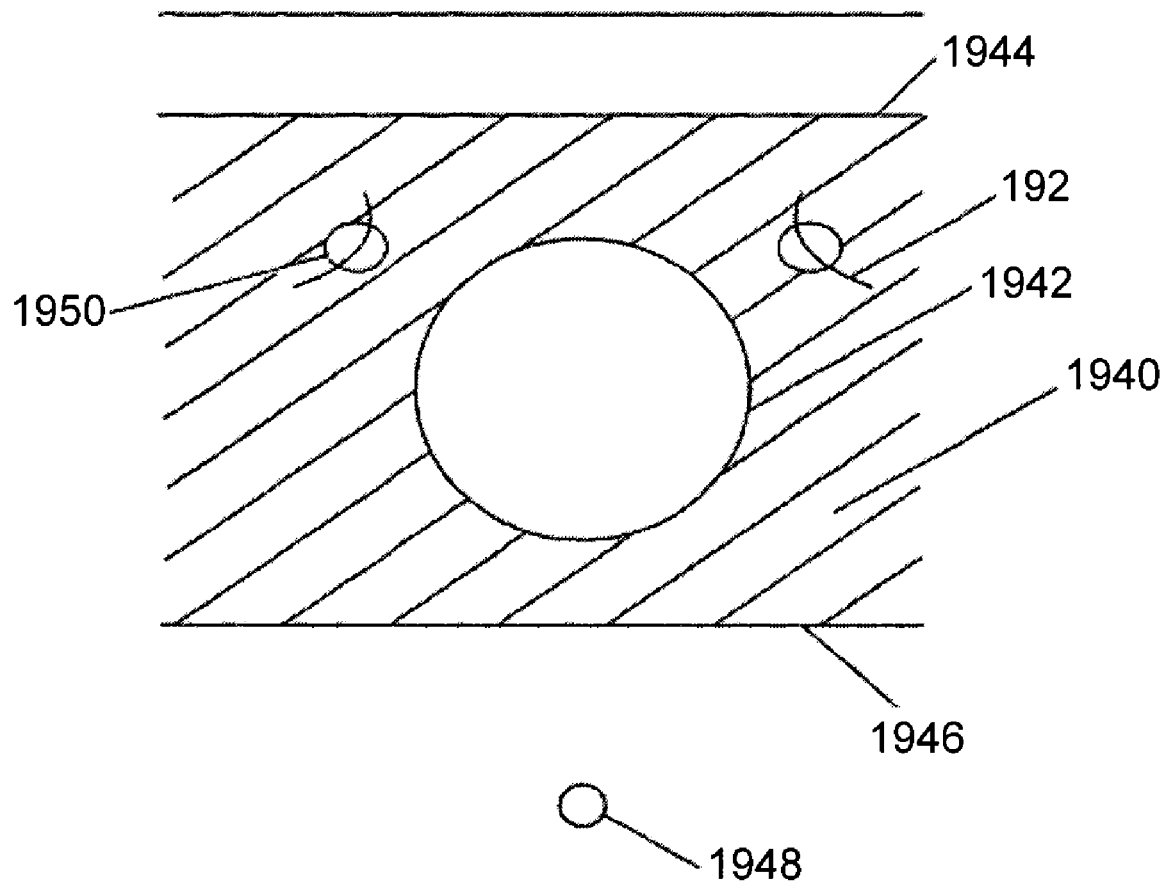
Figure 39A:
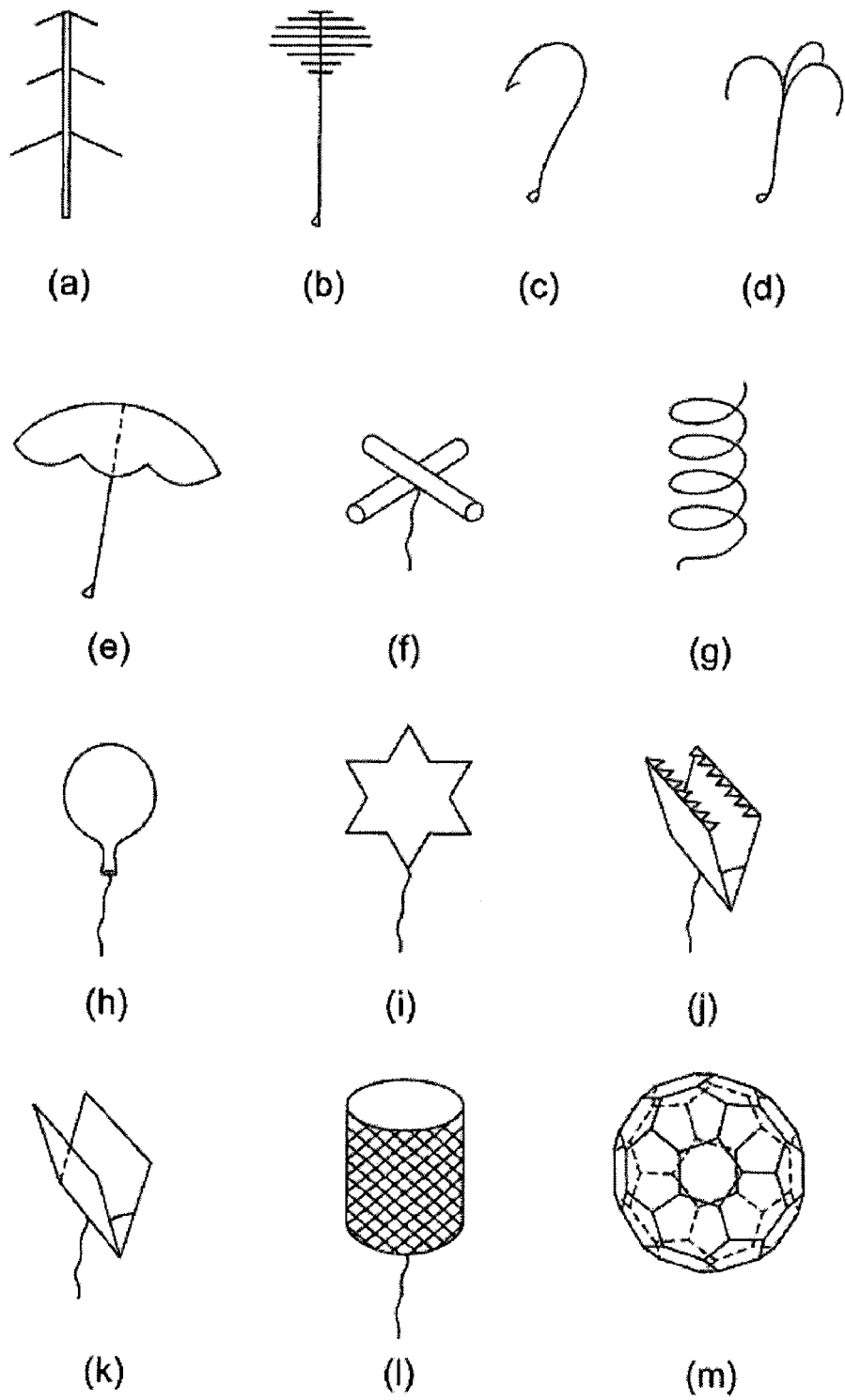
Figure 39B:
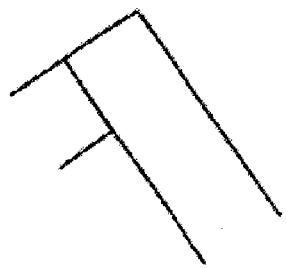
Figure 39B:
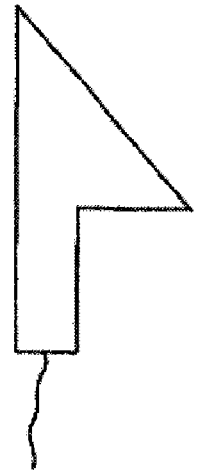
Figure 39B:
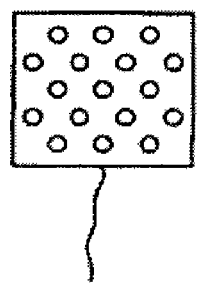
Figure 39B:
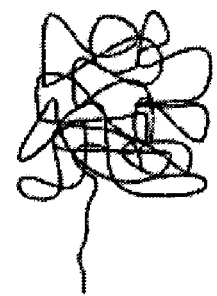

FIG. 30 shows a diagrammatic view of the implant;

FIG. 31 shows a diagrammatic side view of the implant;

FIG. 32a shows retaining means which may be present at the fixing zone;

FIG. 32b shows an illustration of one embodiment of the tape in cross section;

FIG. 32c shows an illustration of a further embodiment of the tape;

FIG. 33 shows an illustration of a further embodiment of the tape wherein the supporting zone is formed from mesh;

FIG. 34 shows a diagrammatic view of the retropubic space, related to needle passage for any pubo-vaginal sling;

FIG. 35 shows an illustration of an introducing tool;

FIG. 36 shows an illustration of a further embodiment of an introducing tool wherein the point of the tool is offset to aid insertion of the implant into the recess of the tool;

FIG. 37 shows an illustration of a further embodiment of an introducing tool;

FIG. 38 shows an illustration of the position of the tape in relation to the bladder taken from a superior view; and FIGS. 39a and 39b show alternative embodiments of retaining means.

Figure 40:
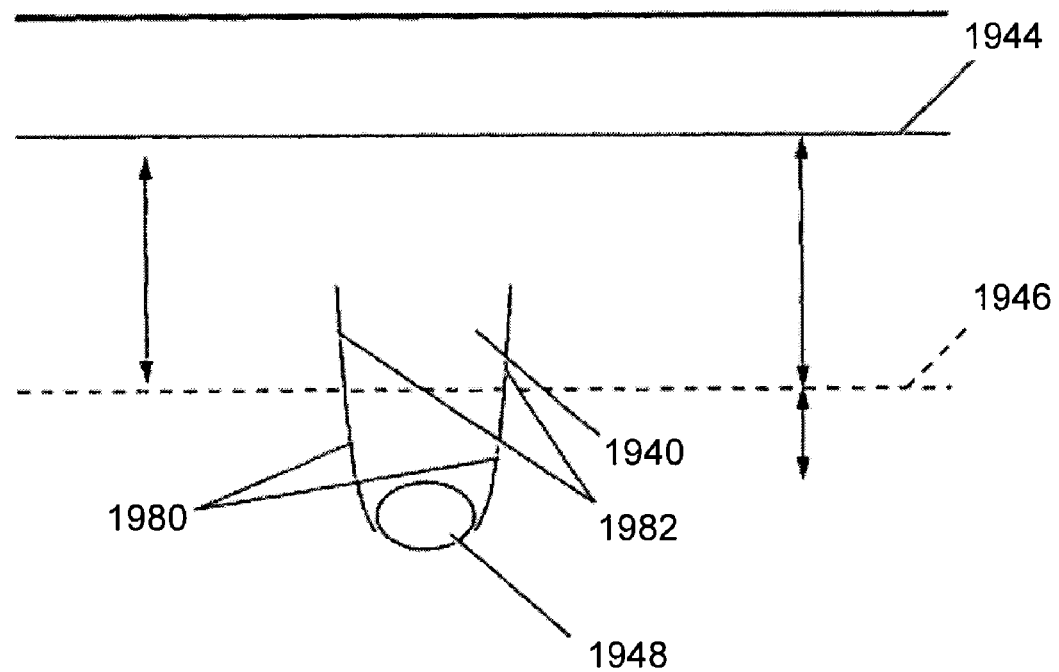

FIG. 40 shows anchor strips positioned on either side of the urethra in the suburethral space below the endopelvic fascia and extending into the retropubic space above the endopelvic fascia.

III.

Figure 10:
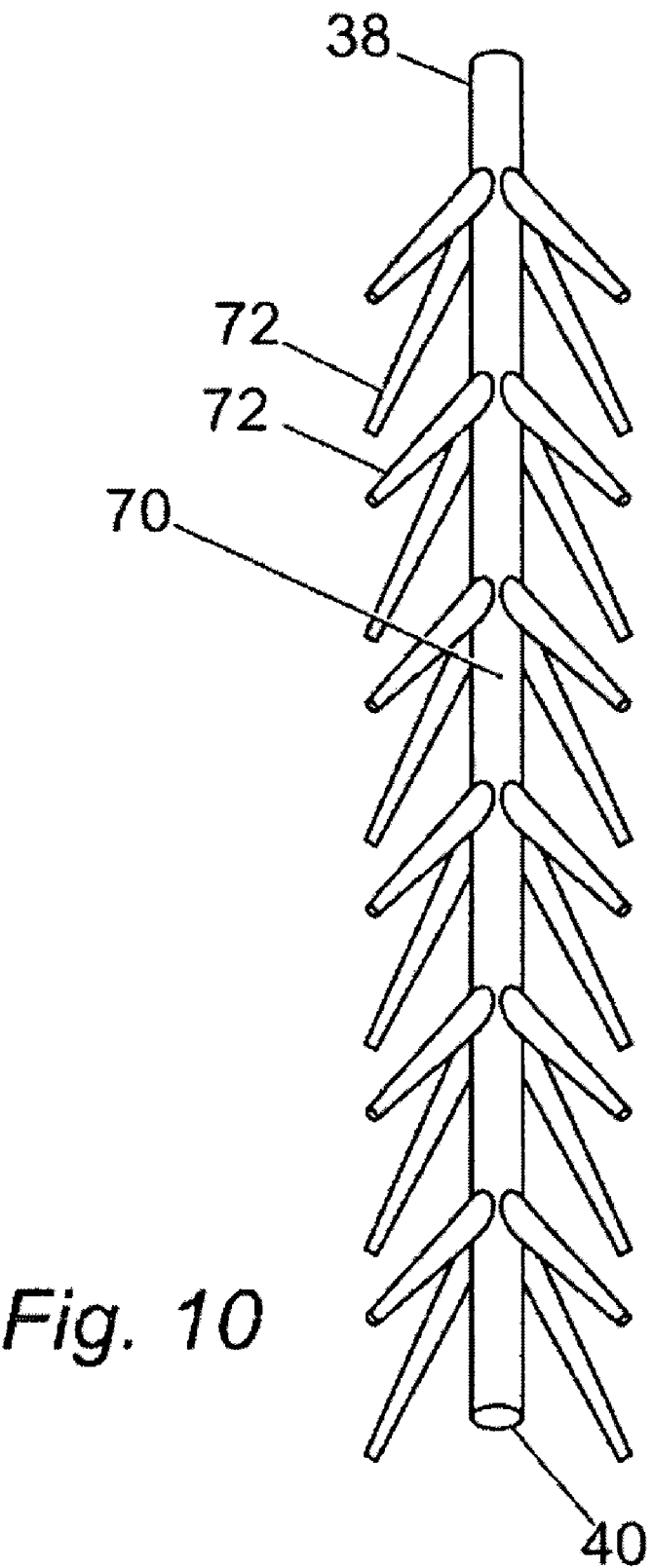
FIG. 10 is an illustration of a retropubic soft tissue anchor for use in the fibro-fatty tissues of the para-urethral tunnel.
Figure 41:
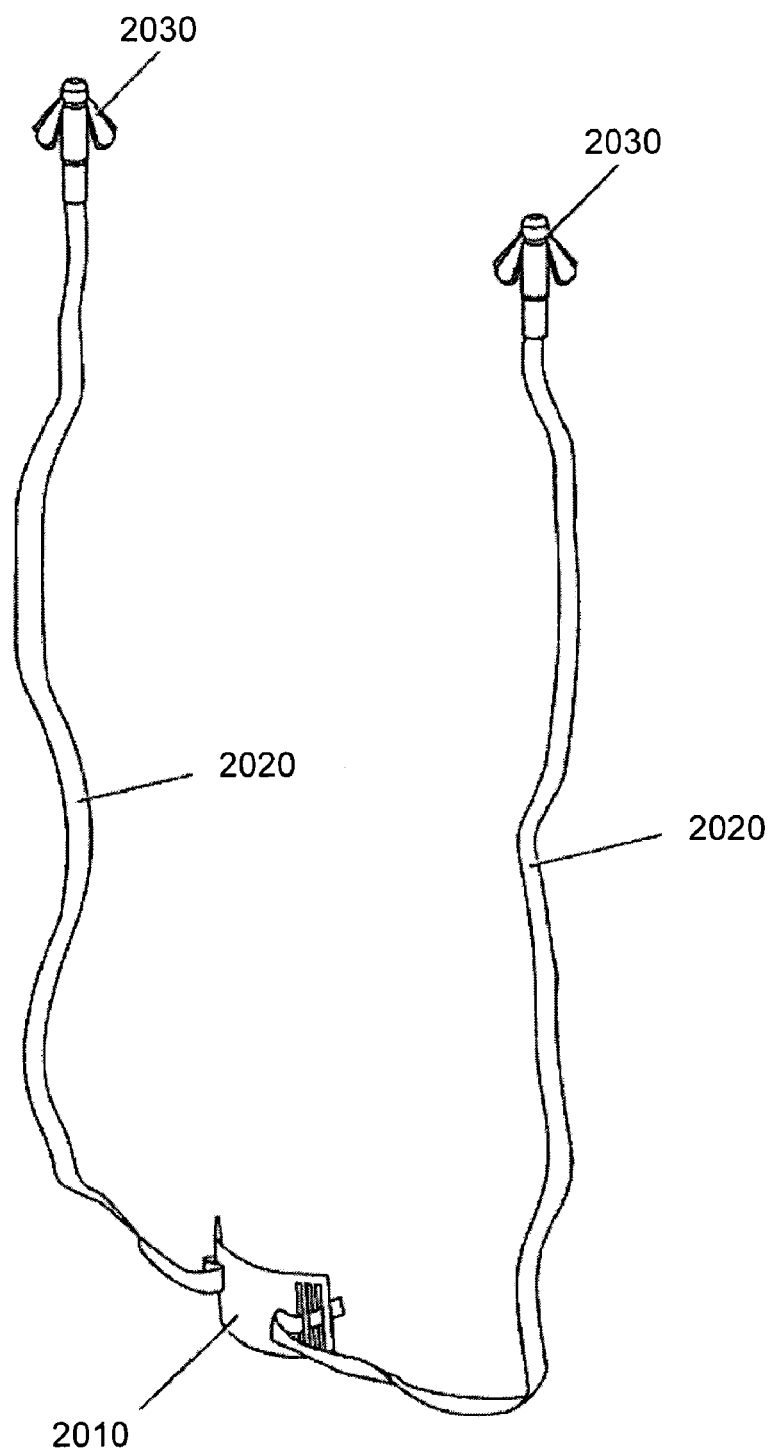
Figure 42A:
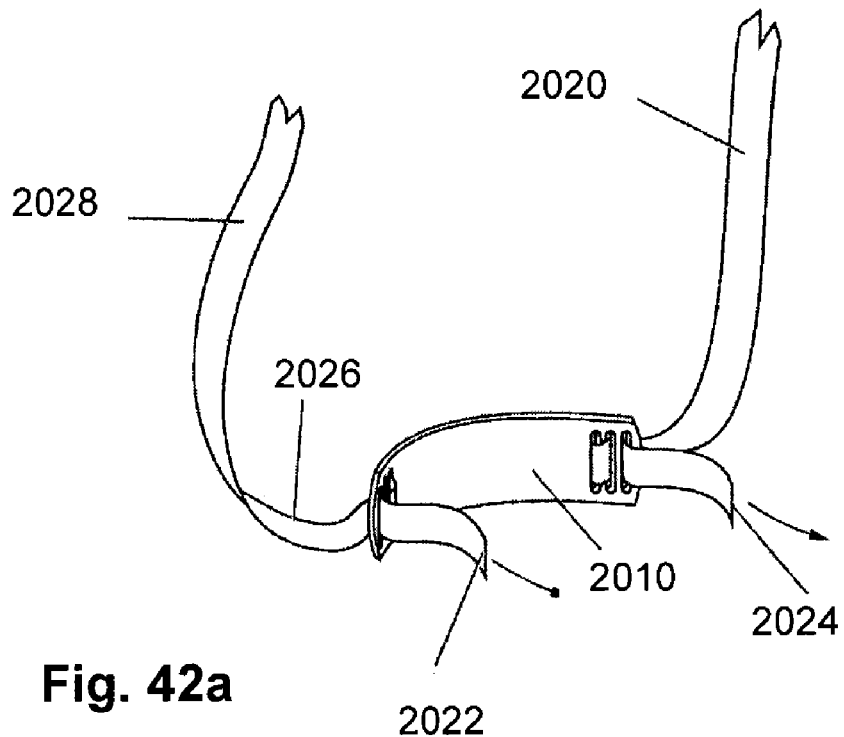
Figure 42B:
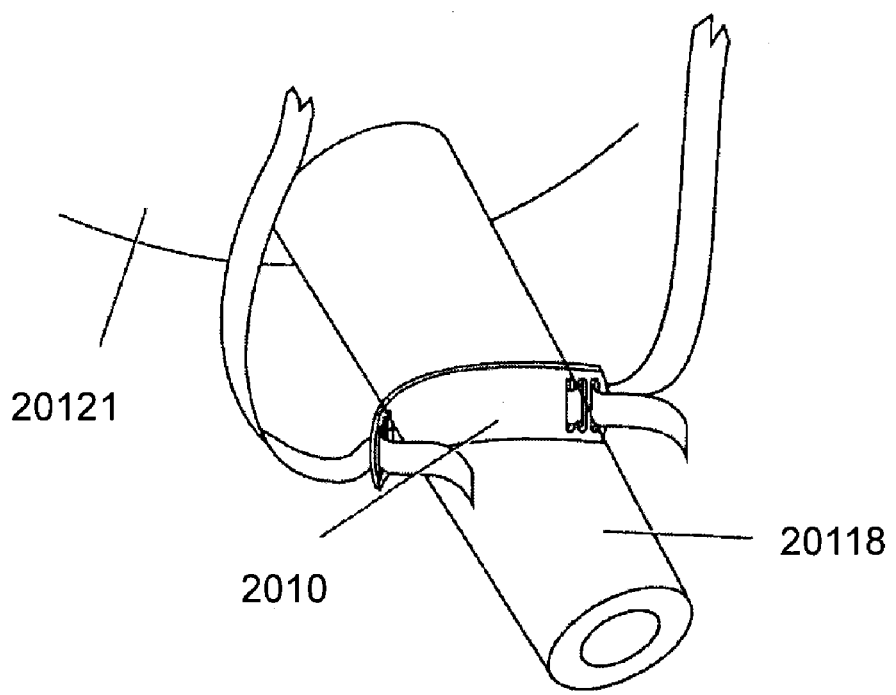
Figure 43:
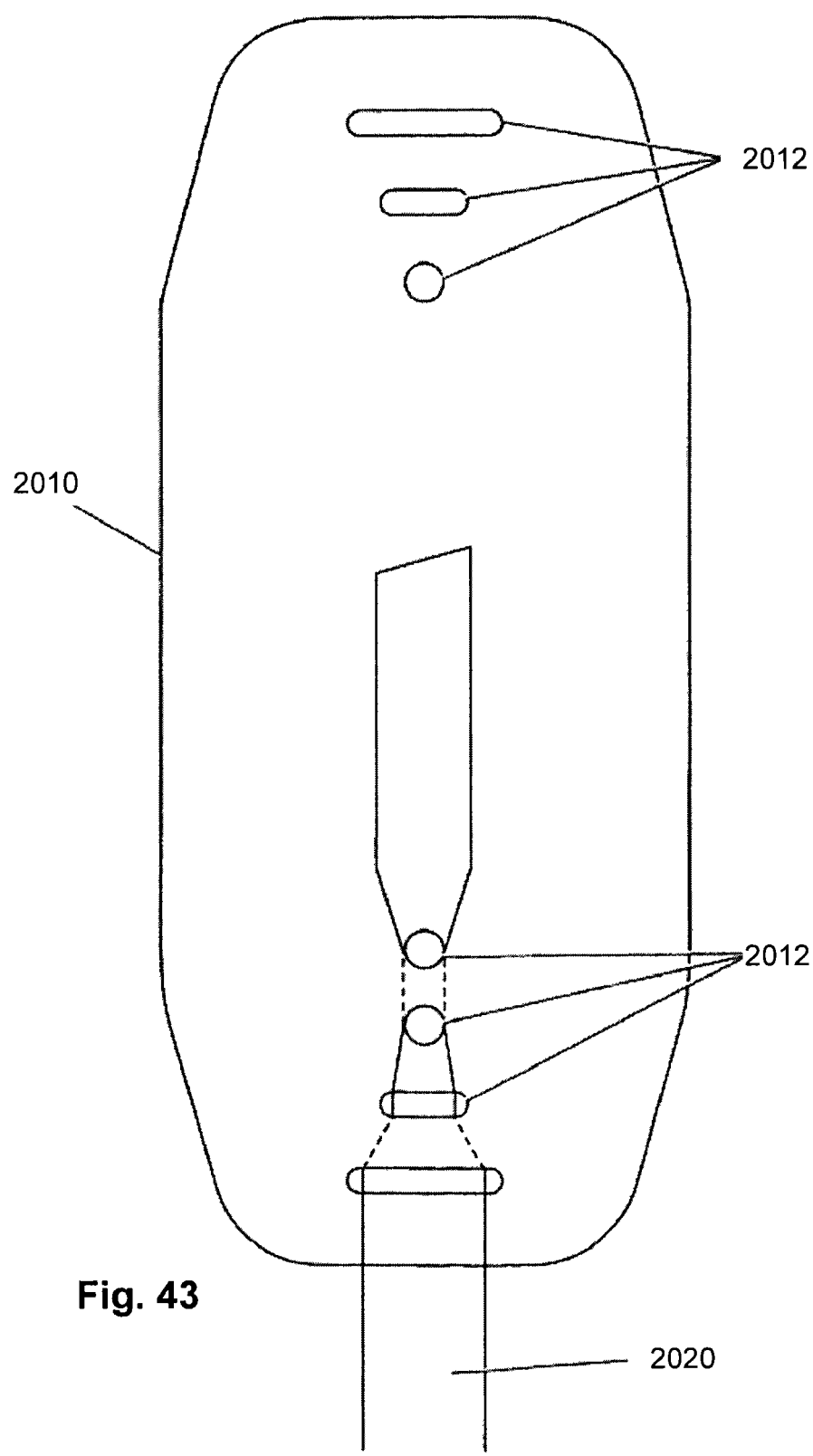
Figure 44:
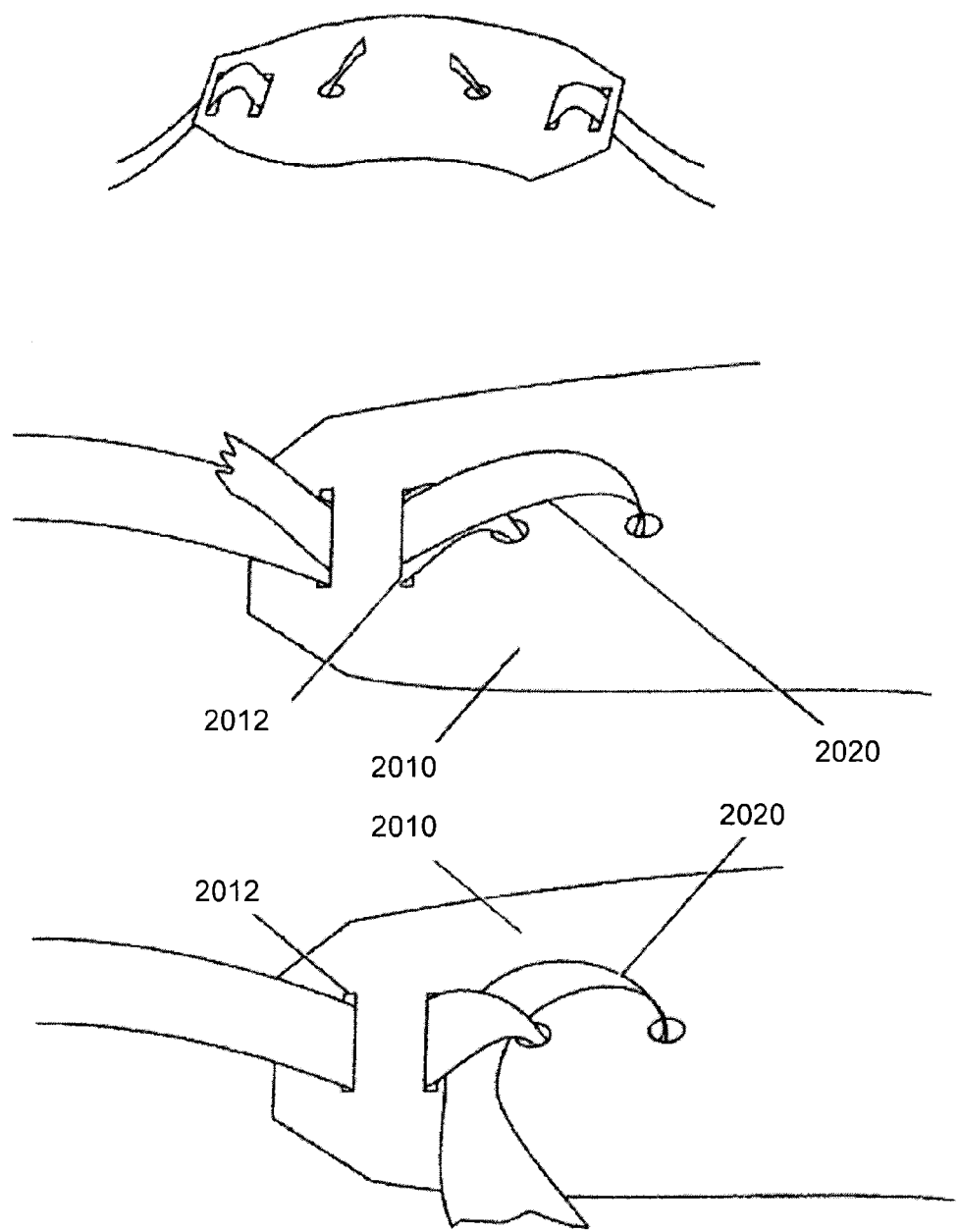
Figure 45:
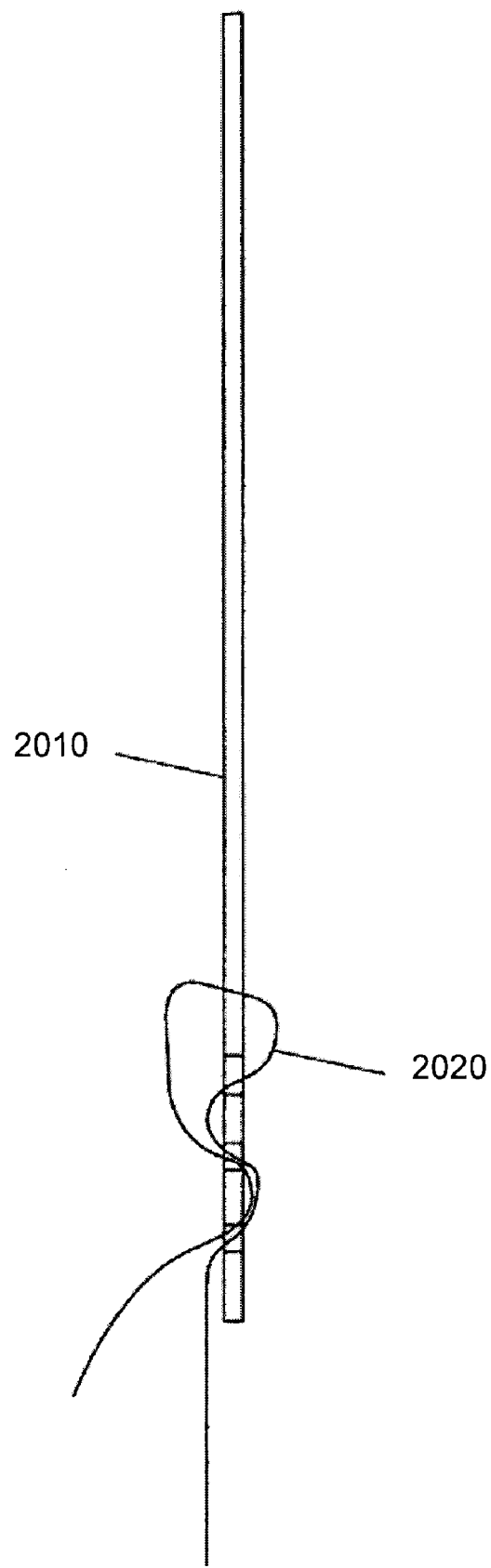
Figure 46A:
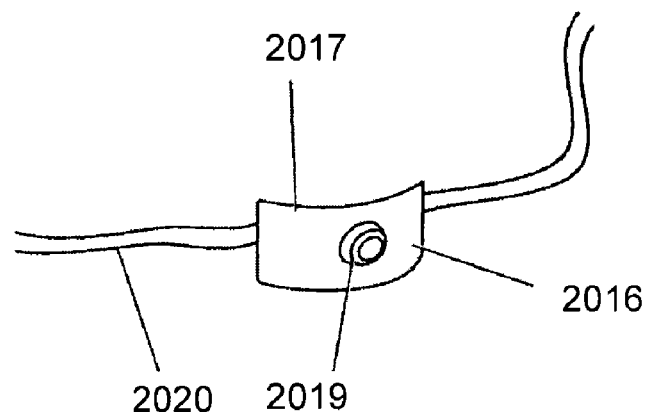
Figure 47A:
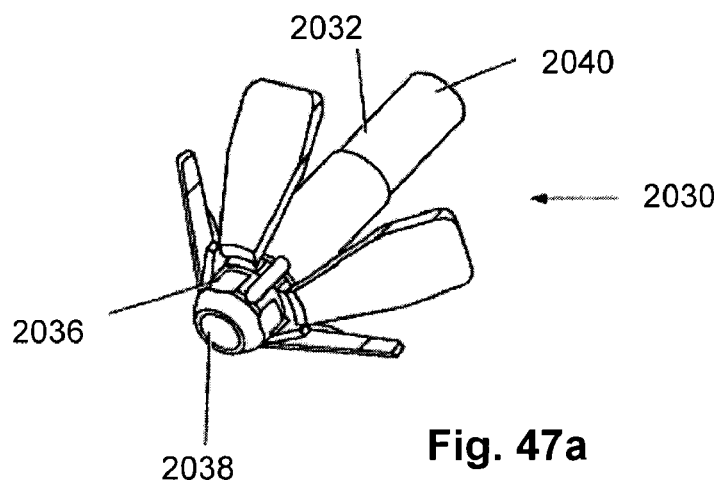
Figure 47B:
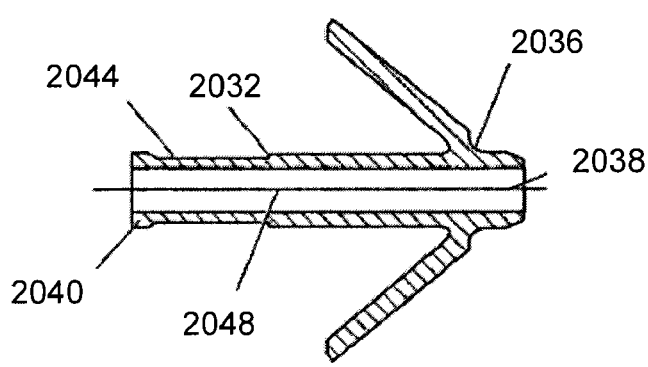
Figure 47C:
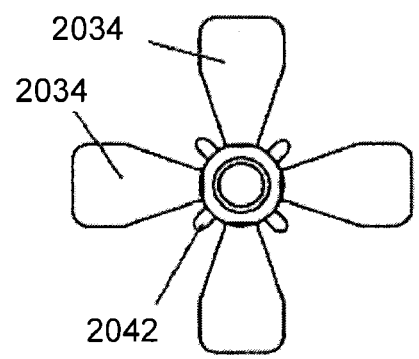
Figure 48A:
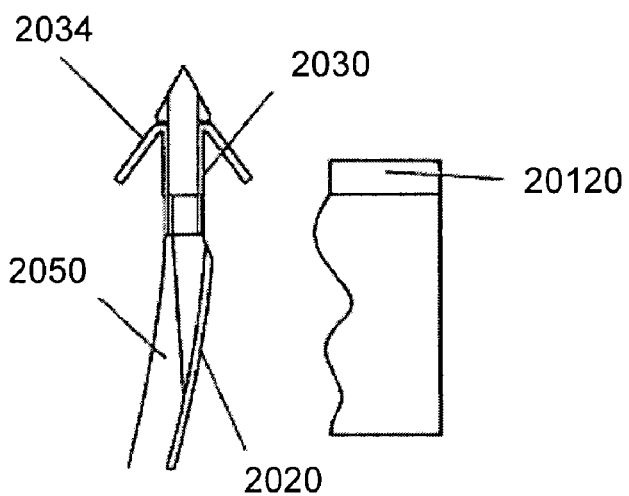
Figure 48B:
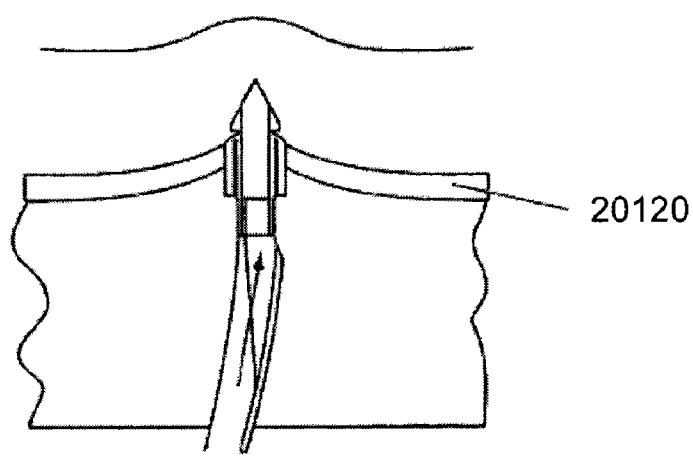
Figure 48C:
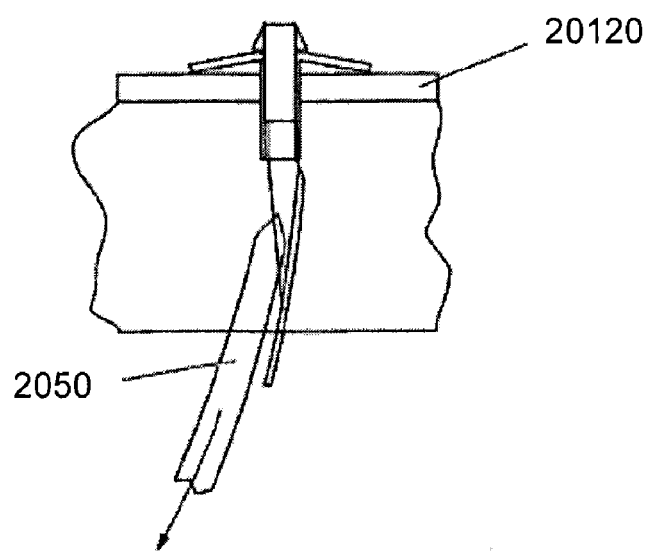
Figure 49:
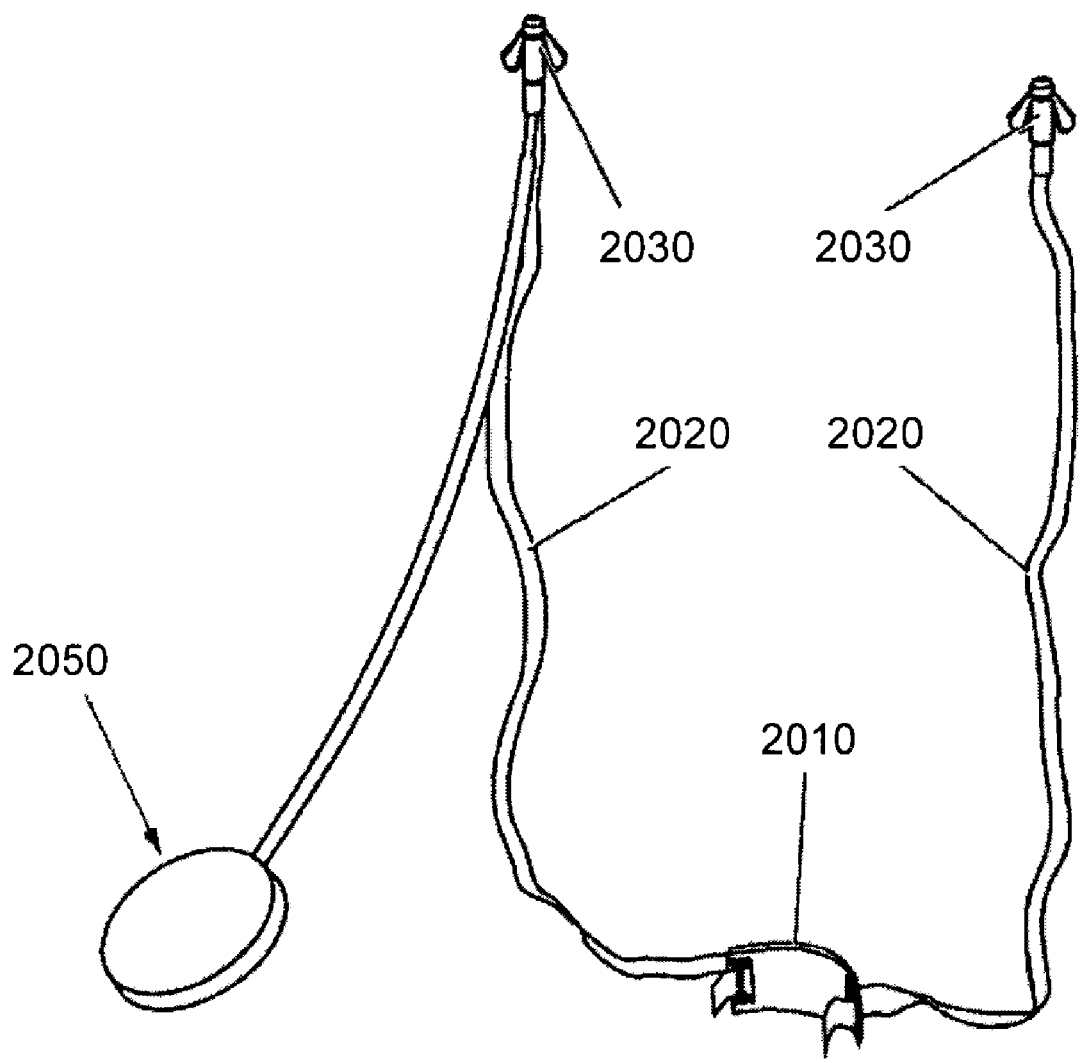
Figure 50:
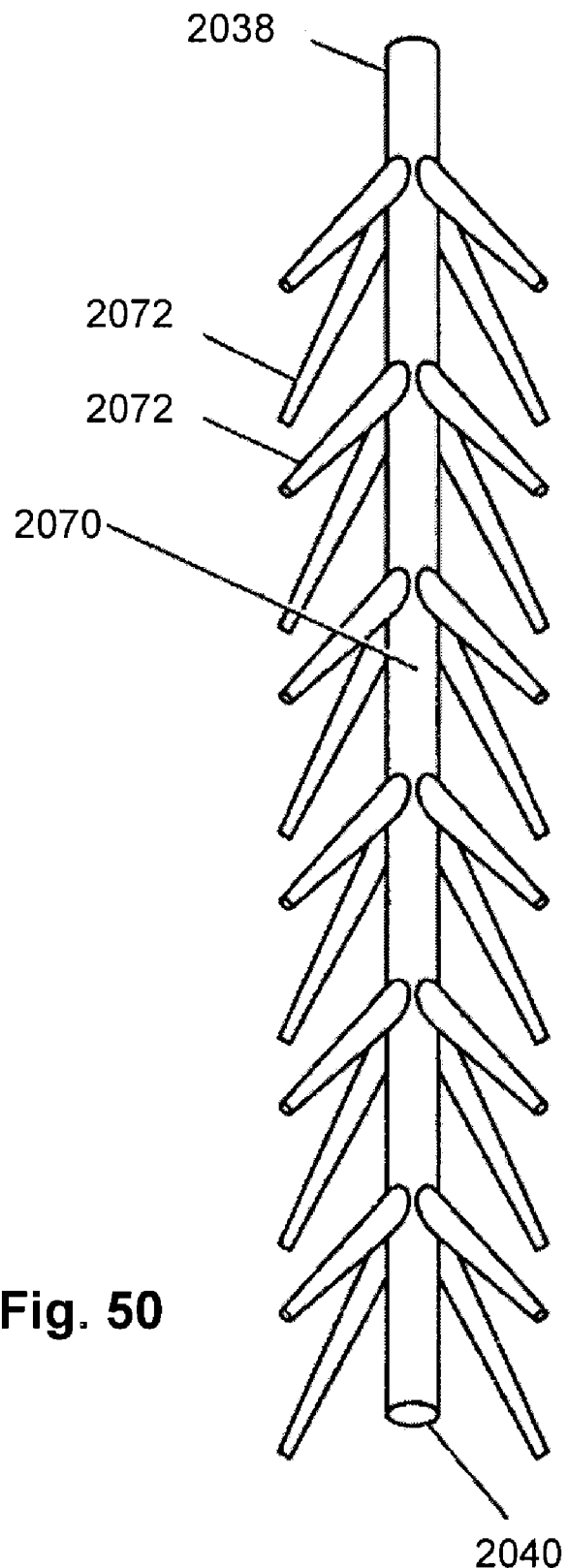
Figure 51:
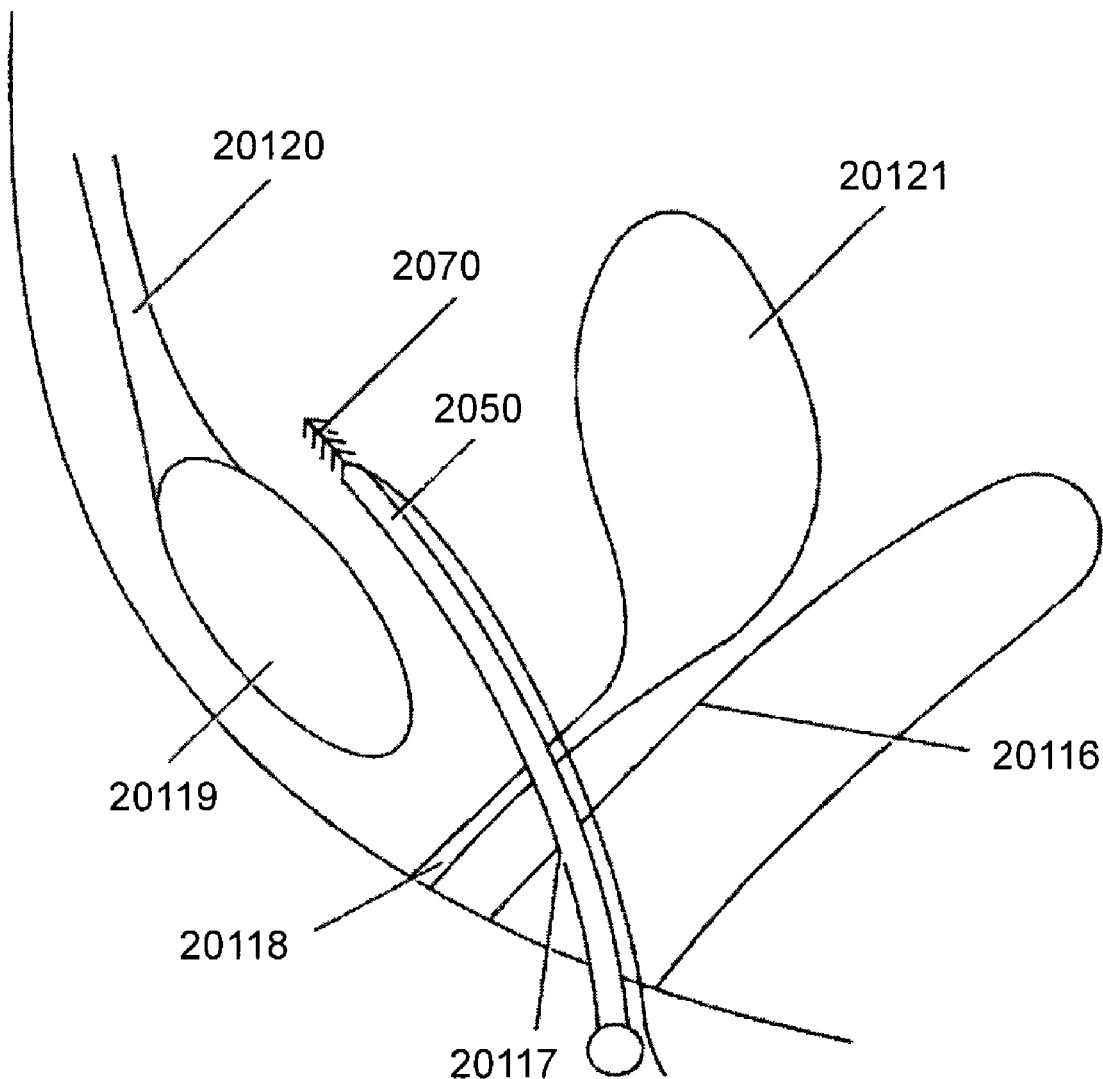
Figure 52:
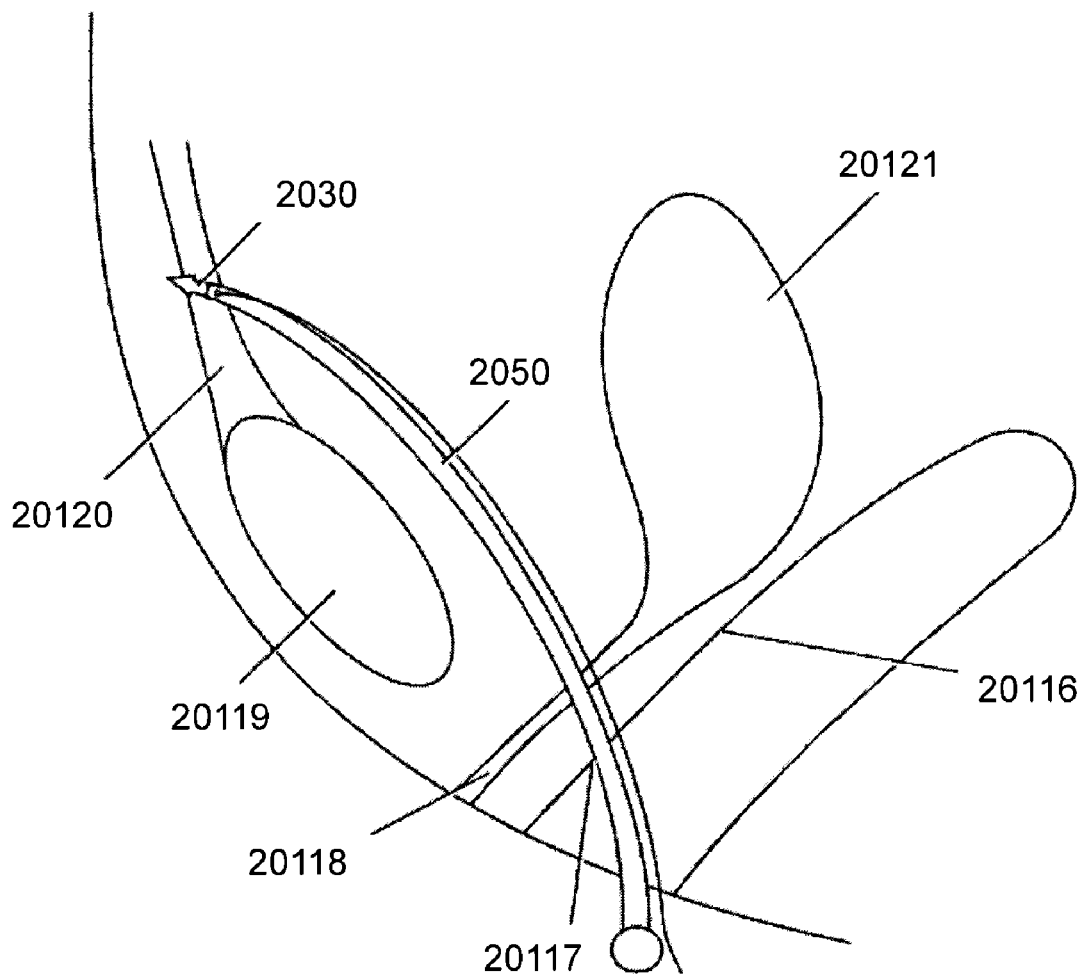
Figure 53:
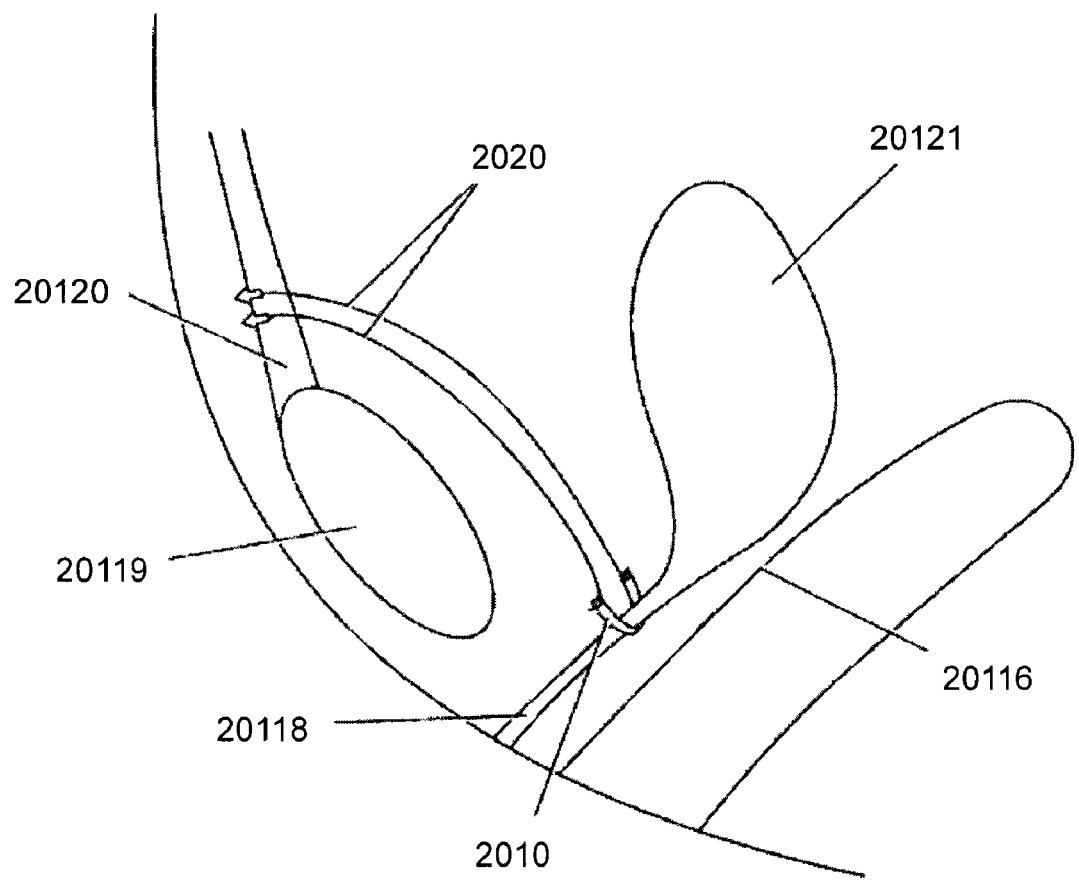
Figure 54:
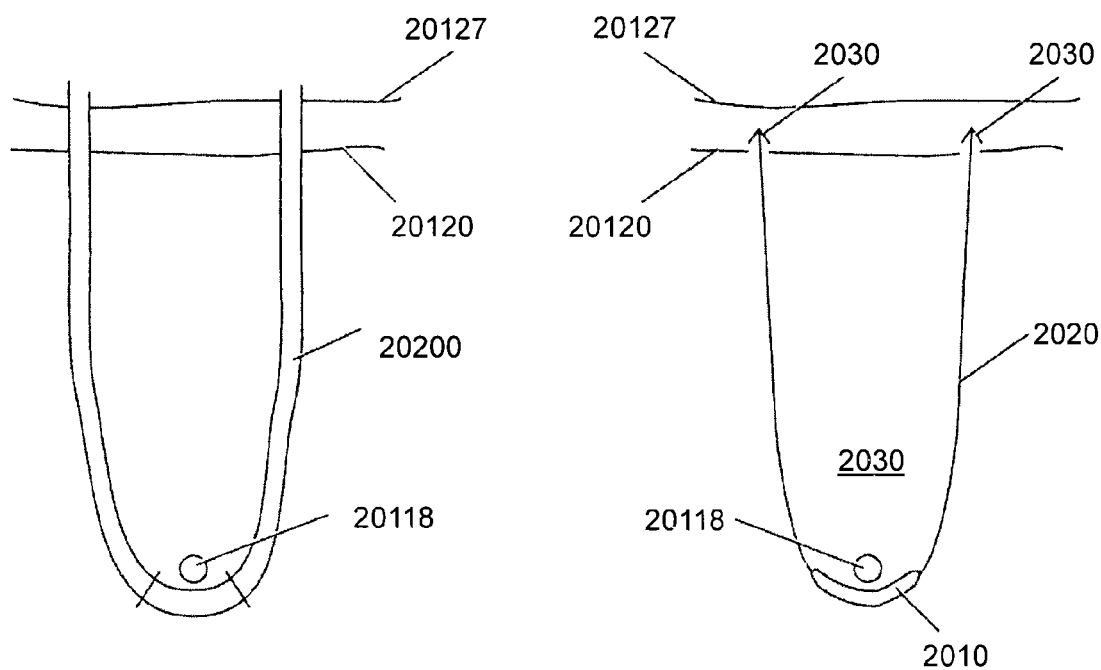
Figure 55:
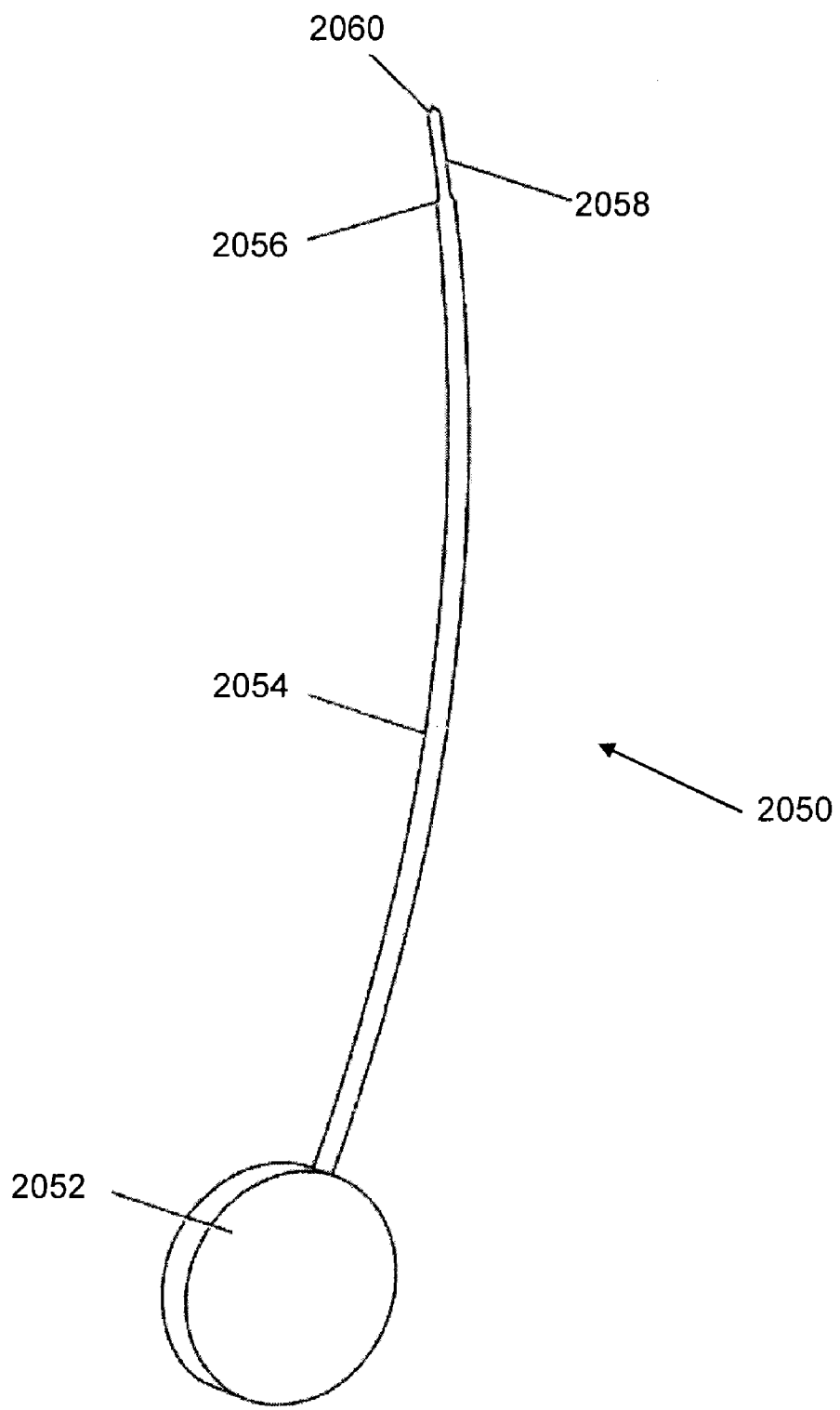
Figure 56:
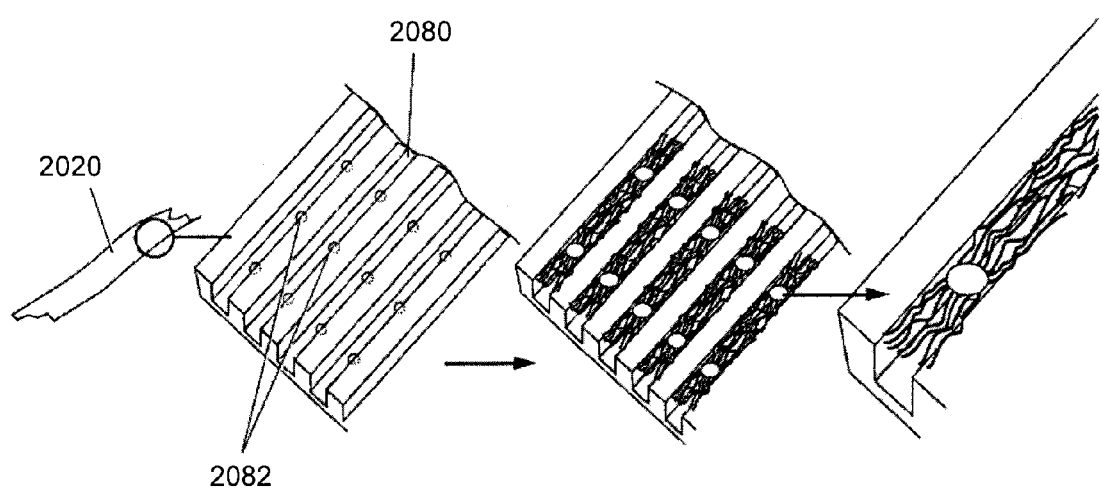

FIG. 41 is an illustration of a surgical implant according to the invention,

FIG. 42 is a line drawing of the suspending means attached to the suburethral support, positioned underneath the urethra, FIG. 43 is an illustration of one embodiment of a suburethral support, FIG. 44 is an illustration of a second embodiment of a suburethral support, FIG. 45 shows suspending means being threaded through an attachment tab of a suburethral support, FIGS. 46A, B and C show alternative methods of attaching suspending means to a suburethral support, FIG. 47 is an illustration of a soft tissue anchor for insertion through the rectus sheath, FIGS. 48A-C are sequential illustrations of insertion of a soft tissue anchor of FIG. 47, FIG. 49 is an illustration of a soft tissue anchor mounted on an introducing tool, FIG. 50 is an illustration of a retropubic soft tissue anchor for use in the fibro-fatty tissues of the para-urethral tunnel, FIG. 51 is an illustration of the placement of a soft tissue anchor of FIG. 10, FIG. 52 is an illustration of an implanting tool and a soft tissue anchor inserted into the rectus sheath, FIG. 53 is an illustration of the surgical implant implanted into the rectus sheath, FIG. 54 is an illustration of the prior art contrasted with the technique of the present invention, FIG. 55 is an illustration of the tool used to insert the surgical implant, and FIG. 56 is an illustration of the surface architecture of the suspending means.

DETAILED DESCRIPTION

I.

Figure 1:
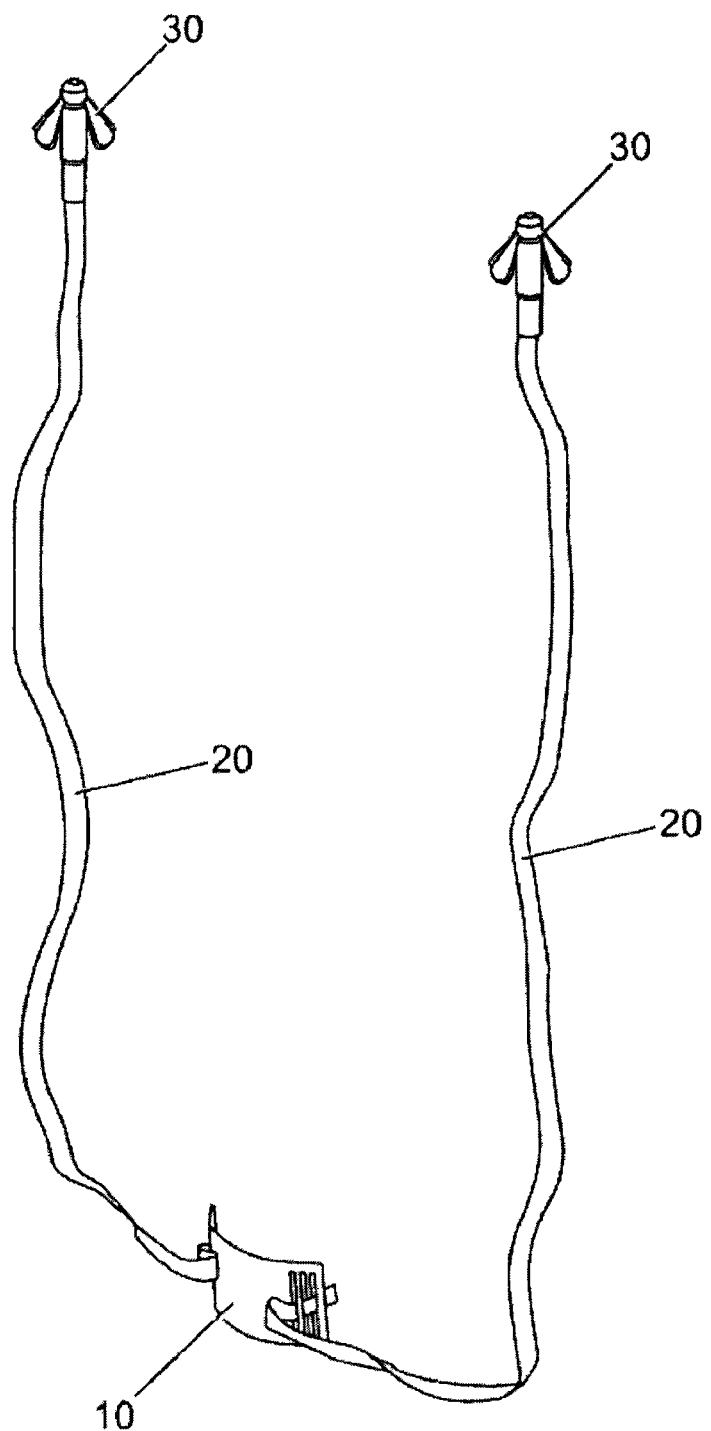
FIG. 1 is an illustration of a surgical implant for anchoring in the rectus sheath.

Referring to FIG. 1, a surgical implant for treating female urinary incontinence has a suburethral support 10, suspending means 20 and at least two soft tissue anchors 30, the suburethral support 10 being positioned in use, loosely under the urethra. The suburethral support has a length L of around 25 mm and a width W of around 10 mm such that it passes around the urethra with a minimum of excess material, although other similar dimensions would also be suitable. In this example, the suburethral support 10 is made from flat polymer tape. At each side 11,13 of the suburethral support 10 suspending means 20 are provided which attach to the suburethral support 10 at a first end 22,24.

The suspending means 20 are attached at a second end 26 to a respective soft tissue anchor 30.

Figure 7A:
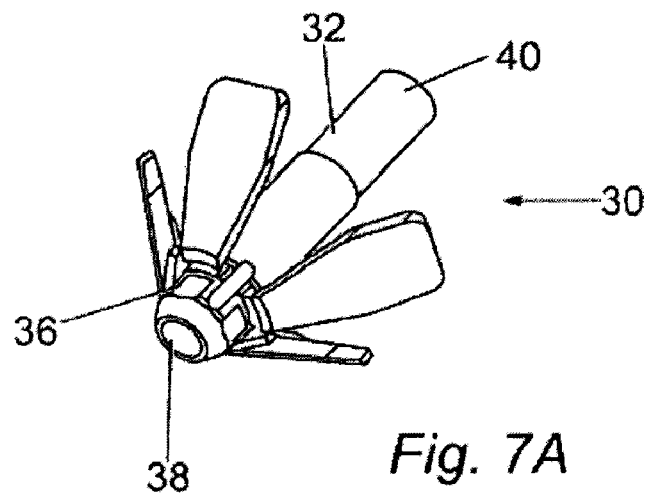
FIGS. 7A, 7B and 7C are illustrations of a soft tissue anchor for insertion through the rectus sheath.
Figure 7B:
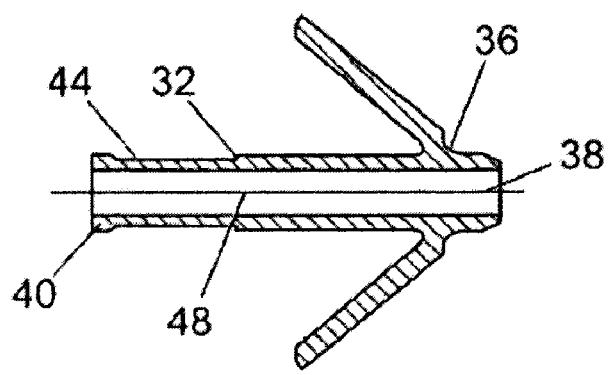
Figure 7C:
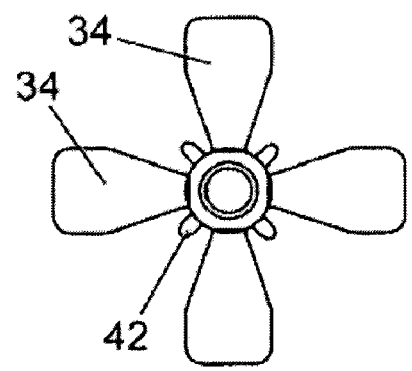

As shown in FIGS. 7a-7C, the soft tissue anchor 30 of the embodiment described comprises a central portion 32 and four winged sections 34 which are attached to the central portion at a first end 38 by resilient hinge means 36 and radially extend from the central portion 32 such that when viewed from the front the anchor device resembles a cross.

Figure 8A:
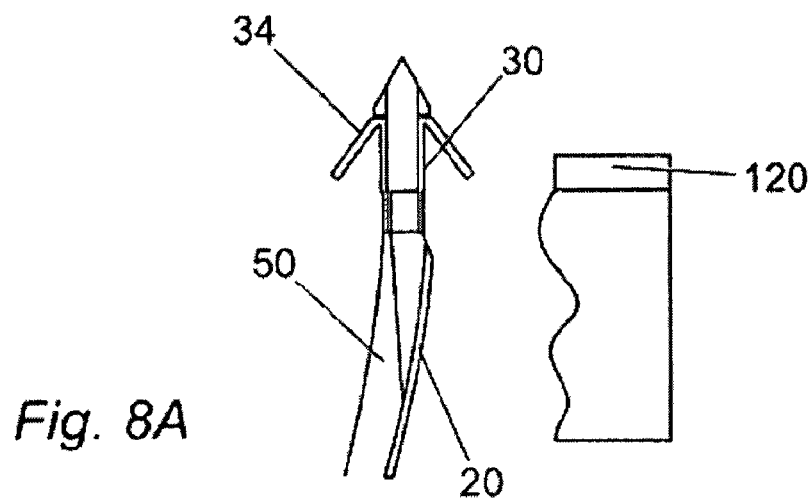
FIGS. 8A-C are sequential illustrations of insertion of a soft tissue anchor of FIG. 7.
Figure 8B:
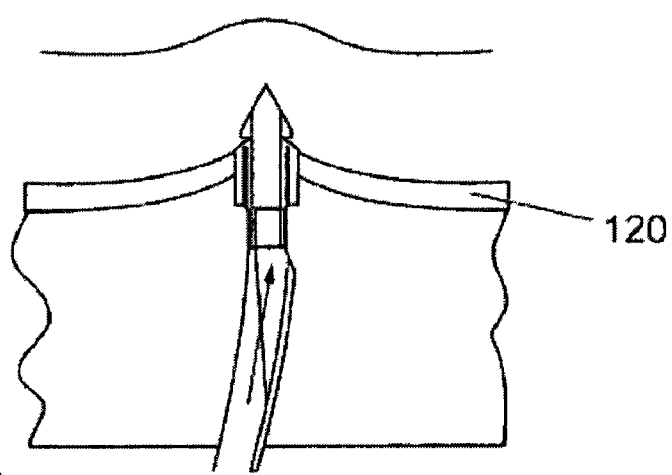

As shown in FIG. 8A the wing sections 34 of the soft tissue anchor 30 having a resting position in which they are inclined towards the rear 40 of the central portion 32 at an angle of around 45°. In FIG. 8B during penetration of the anchor through tissue (the point 60 of the introducing tool enabling the soft tissue anchor to be pushed through the tissue and rectus sheath 120) the wing sections 34 of the soft tissue element 30 may adopt a deflected position which means the penetration of the soft tissue anchor through the tissue and rectus sheath 120 is more effective.

Figure 8C:
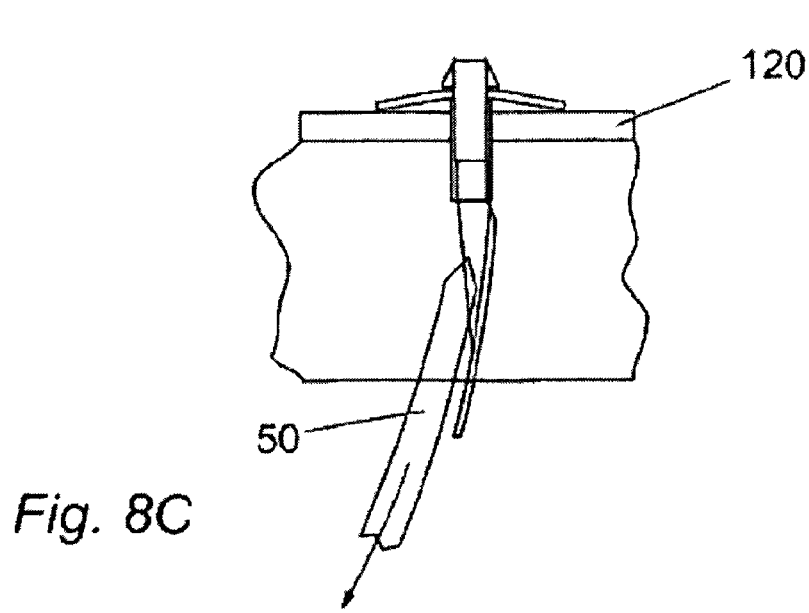

As shown in FIG. 8C once the rectus sheath 120 has been pierced the resilient hinge means 36 cause the wing sections 34 to return to their resting position.

Movement of the soft tissue anchor in a direction opposite to which it was introduced into the soft tissue causes the wing section to be deflected until an endstop 46 is reached which prevents the wing sections 34 moving beyond a point substantially perpendicular to the central portion 32 and prevents retraction of the soft tissue anchor 30 from the soft tissue.

The soft tissue anchor 30 further comprises a hollow portion 48 which extends from the first end 38 to the second rear end 40 of the central portion 32 through which an introducing tool 50 may be placed, as shown in FIGS. 8A-8C.

The introducing tool 50 extends through the hollow portion 48 such that it extends as a sharp point 60 from the first end 38 of the soft tissue anchor 30 such that the sharp point 60 allows penetration of the tissue by the soft tissue anchor 30.

Stud like projections 42 which extend radially from the central portion 32 are angled such that they extend further radially from the central portion 32 as they extend towards the rear 40 of the central portion 32, this inclination allowing the soft tissue anchor 30 to pass more easily into the soft tissue.

A recessed portion 44 is positioned toward the rear end 40 of the central portion 32 to facilitate attachment of the suspending means 20 to the soft tissue anchor 30.

The suspending means 30 may be respectively attached to the soft tissue anchor 30 at this recessed point 44 by crimping a tube around the suspending means 20 to fix the suspending means 20 to the soft tissue anchor 30.

Figure 15:
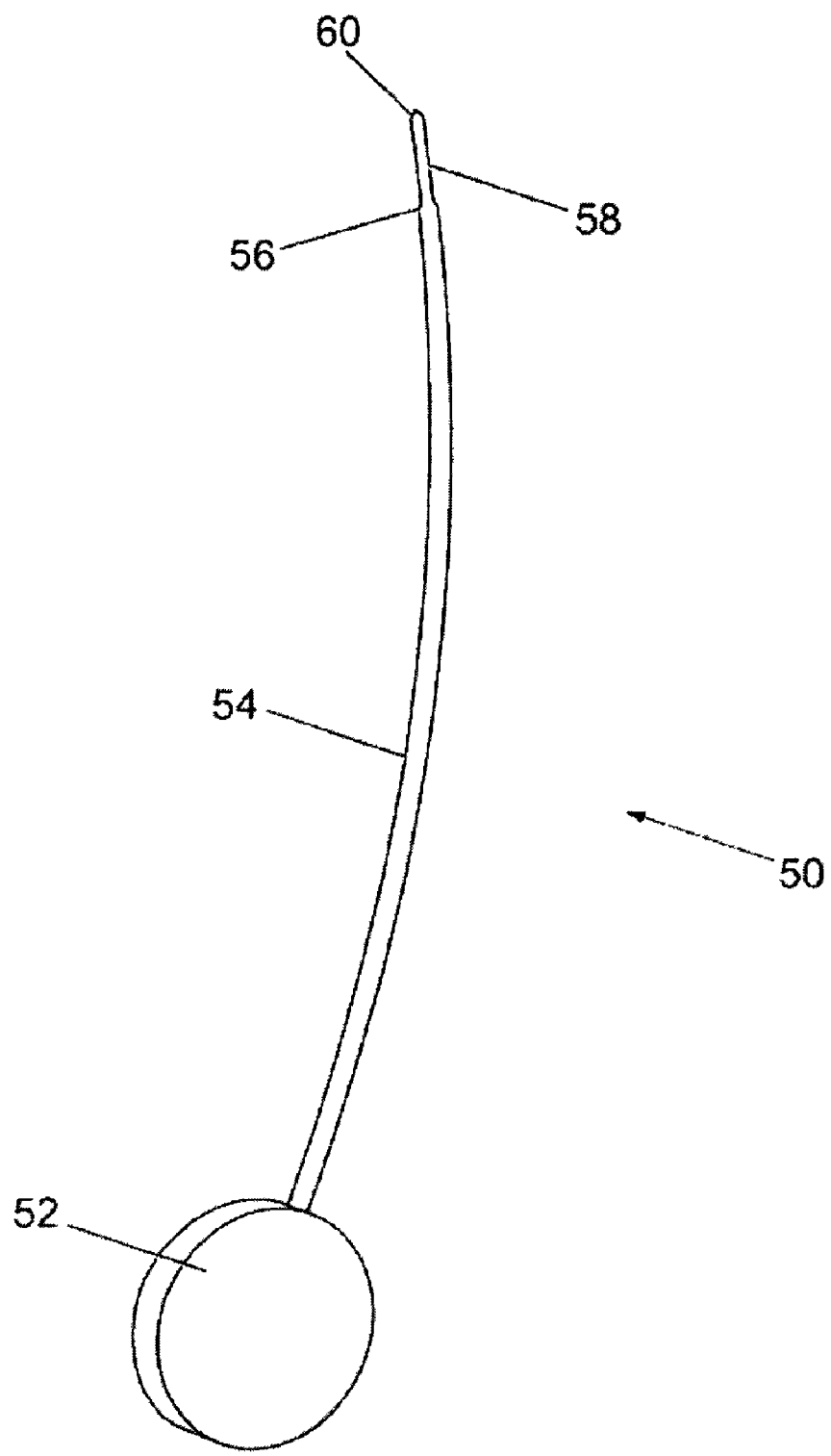
FIG. 15 is an illustration of the tool used to insert the surgical implant.

In the embodiment shown the soft tissue anchor may be suitably positioned in the rectus sheath 120 using an introducing tool 50. As shown in FIG. 15 the tool 50 comprises a handle 52 and elongate body 54. The elongate body 54 is curved through an angle of approximately 30° to facilitate positioning of the soft tissue anchor 30 in the rectus sheath or surrounding soft tissue of the human body from an incision in the upper wall of the vagina (as described below). The soft tissue anchor 30 is located on the elongate body at a narrowed portion 58 of the introducing tool such that the soft tissue anchor is held in place by an abutment 56 such that the narrowed portion 58 may extend through the hollow portion 48 of the soft tissue anchor 30 such that the point 60 of the insertion tool 50 protrudes from the first end 38 of the soft tissue anchor and allows the soft tissue anchor to be inserted into the human body through the soft tissues and more specifically through the rectus sheath 120 during the placement of the soft tissue anchor.

The placement of the soft tissue anchor 30 on the insertion tool 50 is shown in FIGS. 8B and 8C, which shows the soft tissue anchor 30 being pushed through soft tissue fascia, such as the rectus sheath 120. Once the soft tissue anchor has penetrated the rectus sheath fascia 120, as shown in FIG. 8B, the introducing tool 50 can be withdrawn, as shown in FIG. 8C, leaving the soft tissue anchor 30 in place.

As shown in FIG. 10 the soft tissue anchor may alternatively be comprised of a central portion 70 and a plurality of projections 72 the projections extending radially from the central portion 70 and arranged along a substantial portion of the length of the central portion 70. The projections 72 may be of any shape such that they provide resistance within the fibro-fatty soft tissue and blood tissues of the para-urethral tunnel in the direction opposite to that in which the soft tissue anchor is introduced.

This resistance is also provided by the multiple layers, typically between 5-10 layers of projections 72 which extend from the central portion 70.

Using these multiple layers of projections 72 it is not necessary to insert the soft tissue anchor through the rectus sheath 120. Instead the soft tissue anchor should be positioned as high in the retropubic space as possible in the fibro-fatty soft tissue.

In embodiments of the anchors suitable for anchoring in the soft tissue of the perineum, the soft tissue anchors may be provided with projections which allow penetration of the soft tissue of the perineum and which provide resistance to removal of the anchors from the soft tissue of the perineum.

In the embodiment of the method wherein the anchors are anchored in the soft tissues of the perineum, an embodiment of an anchor comprises multiple layers of projections 72. The multiple layers of projections enable the anchors to be fixed in the soft tissue of the perineum with suitable fixation without requiring the extending through the obturator foramen.

In the embodiment of the soft tissue anchor comprising multiple layers of projections 72 which resembles a Christmas tree, as shown in FIG. 10, the introducing tool comprises a collar which releasably retains the projections during insertion into the retropubic space. The collar may comprise a semi-sharp beveled needle. Following insertion of the Christmas tree like anchor into the fibro-fatty soft tissue of the retropubic space the introducing tool is withdrawn removing the collar from around the plurality of projections 72 of the soft tissue anchor, which due to their memory expand outwards from the central portion 70 and grip the fibro-fatty soft tissue of the retropubic space at multiple layers. The collar of the introducing tool which extends around the soft tissue may contain a cross-sectional opening such that once the tool is withdrawn the collar may be removed from the surgical implant by passing the implant through the cross-sectional opening.

Accordingly the invention also provides an introducing tool for use in inserting the soft tissue anchor.

Suspending means 20 attached to the soft tissue anchors are formed from a strip of plastics material such as polypropylene which is sufficiently soft to avoid damaging the urethra or surrounding body tissue and suitably inert such that it can be left in the human body for a long period of time without causing adverse reactions. Again, other suitable materials will be apparent to those skilled in the art.

The polypropylene mesh strip of 3-5 mm in width which forms the suspending means 20 has smooth edges to avoid adhesion of the soft tissue to the strip, reducing problems associated with leaving foreign material in the human body for long periods of time.

Figure 16:
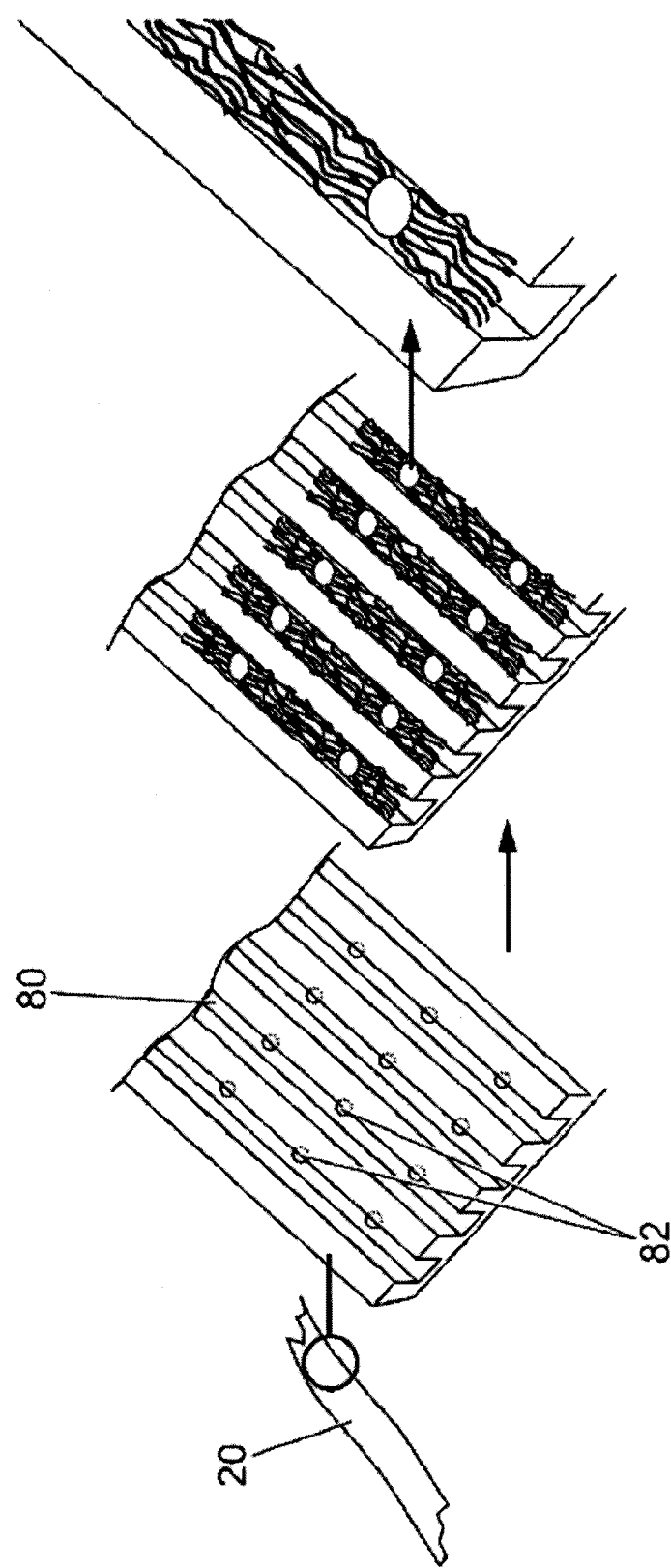
FIG. 16 is an illustration of the surface architecture of the suspending means.

As shown in FIG. 16 the polypropylene mesh strip further comprises pores or pits 80 ranging in width across the surface of the strip from 50 mm to 200 mm, which extend through the strip from a first surface of the strip 26 to a second opposite surface 28 of the strip the pores 80 allowing tissue in-growth to secure the suspending means 20 in the body.

The pores 80 are created by post synthesis treatment of the polypropylene mesh material by a laser.

The polypropylene mesh which forms the suspending means 20 also comprises microgrooves 82 of width 5 μm and of depth 5 μm on the surfaces of the polypropylene mesh.

The microgrooves 82 are aligned such that they are substantially parallel with each other and separated by ridges of around 5 μm in width.

The ridges are formed by square pillars the base of the microgroove being substantially perpendicular to the square pillars or beveled in relation to the pillars. The microgrooving 82 being present on both surfaces of the suspending means to orientate and align the proliferating fibroblasts on the surface of the plastics material and cause axial alignment of collagen fibres and formation of at least one strong ordered neoligament.

This orientation and alignment of the proliferating cells adding mechanical strength to the tissue which forms around the plastics material such that it is more able to support the urethra.

The suburethral support is not provided with pores, pits or grooves to discourage the formation of peri-urethral adhesions.

Once the soft tissue anchors have been suitably positioned in either the soft tissue of the para-urethral tunnel or through the rectus sheath 120 the length of the suspending means 20 can be altered such that the suburethral support 10 hangs loosely under the urethra.

Figure 2A:
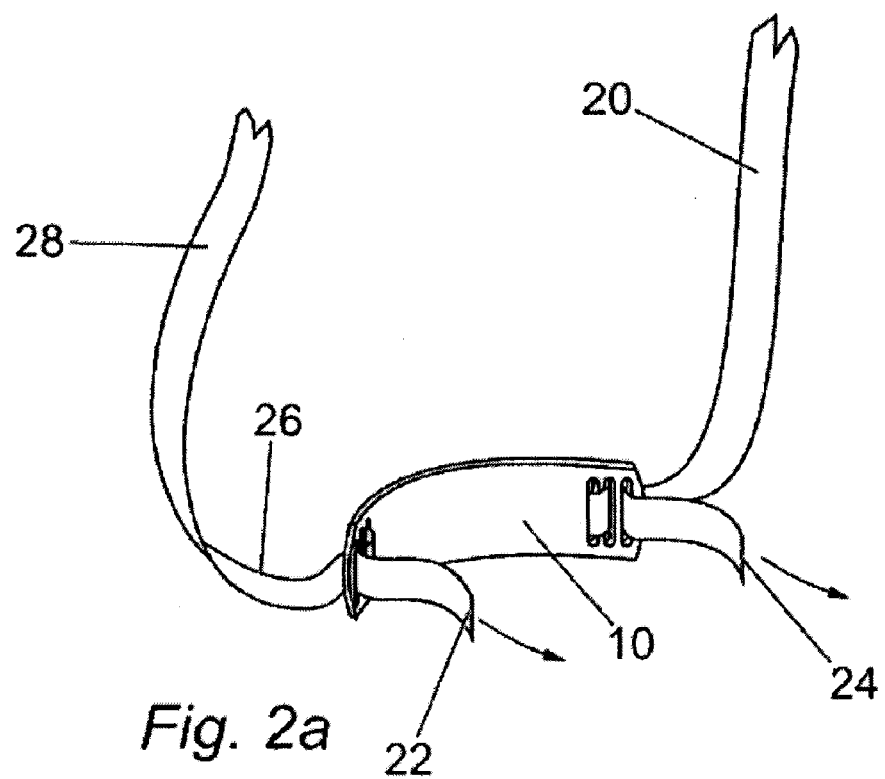
FIGS. 2a and 2b are line drawings of the suspending means attached to the suburethral support, positioned underneath the urethra.
Figure 2B:
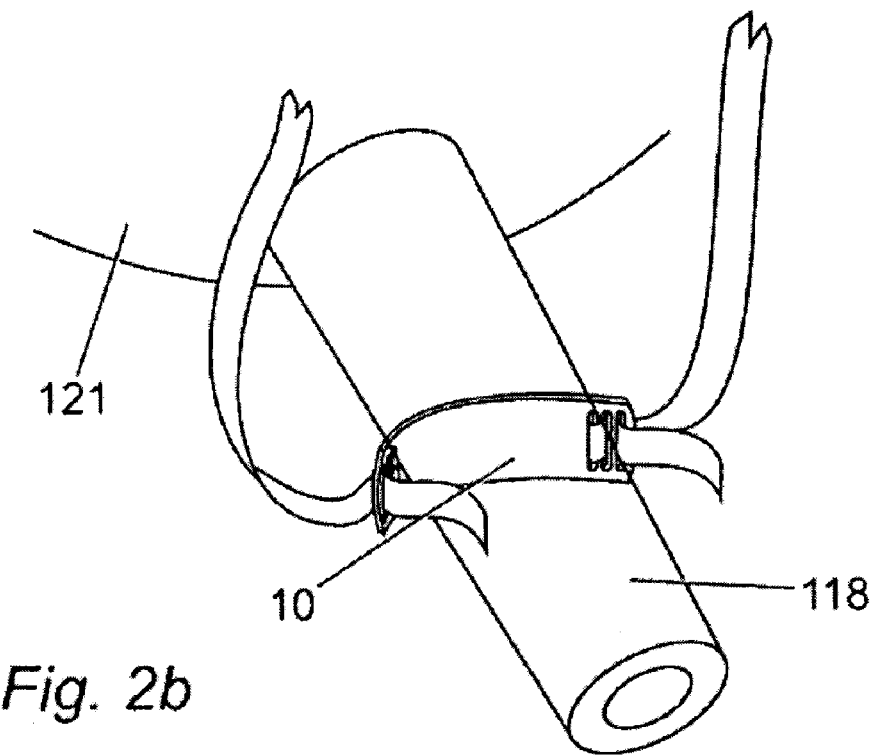
Figure 3:
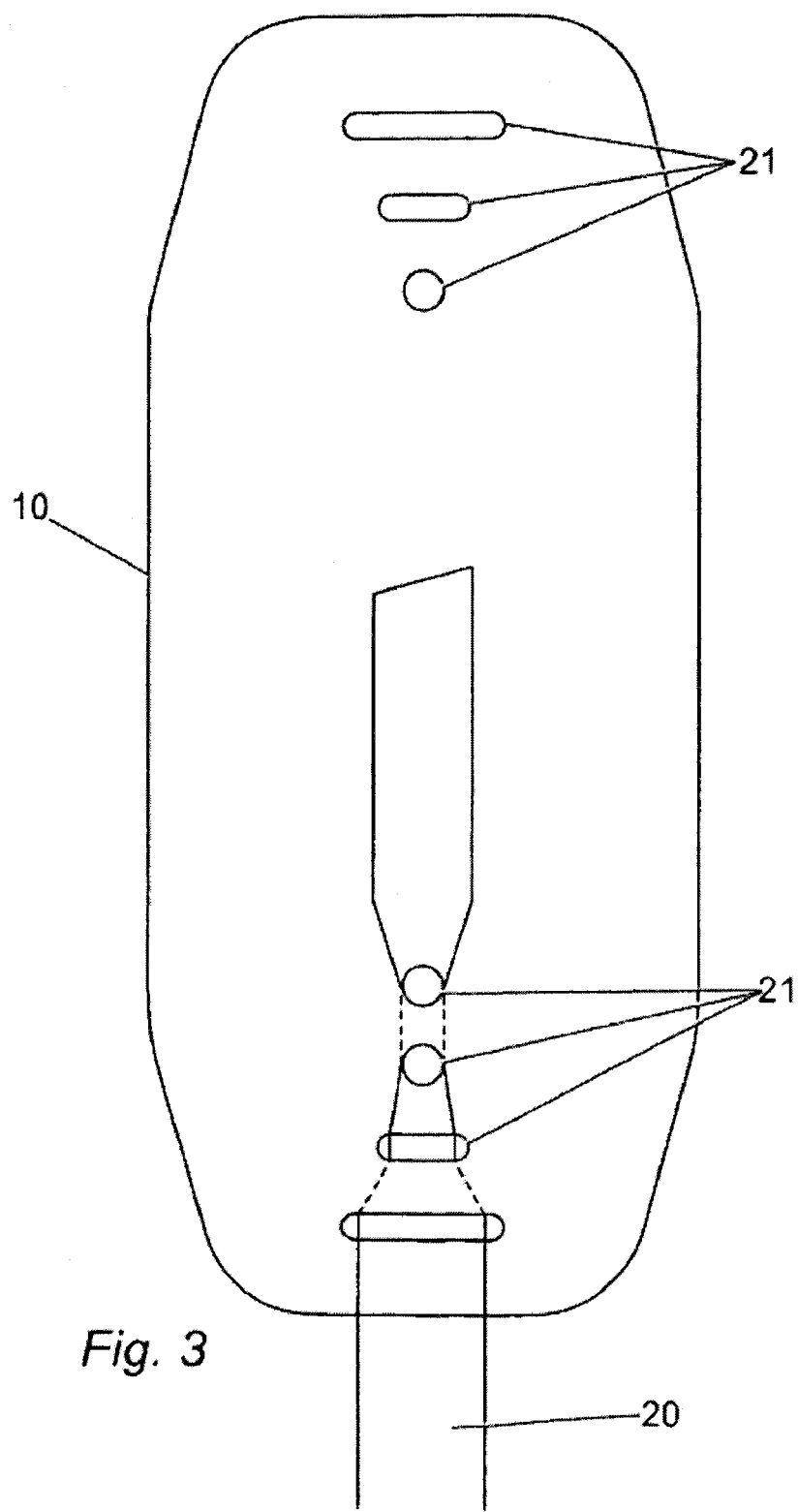
FIG. 3 is an illustration of one embodiment of a suburethral support.
Figure 4:
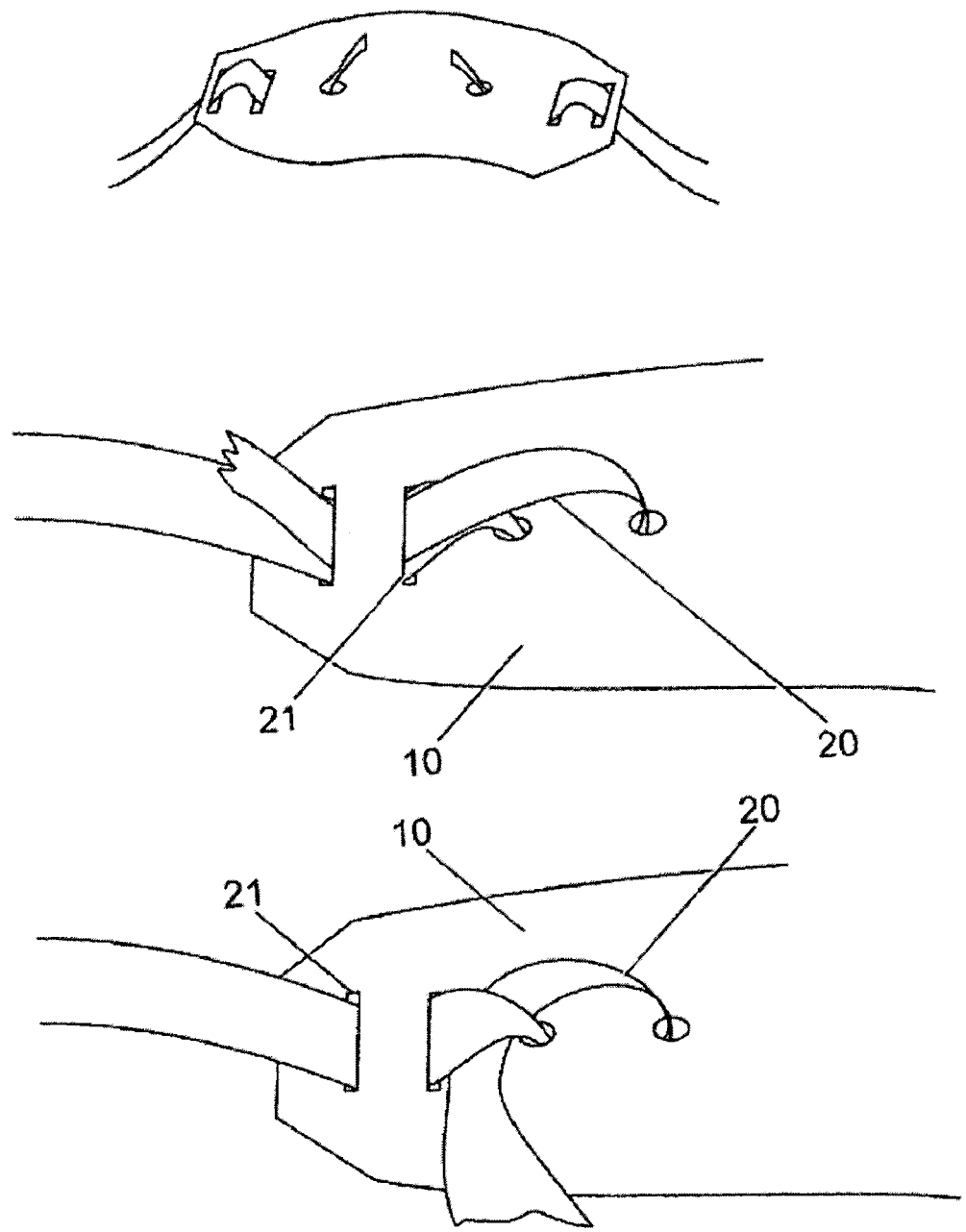
FIG. 4 is an illustration of a second embodiment of a suburethral support.

As shown In FIGS. 2a and 2b the suspending means 20 are attached at a first end 22, 24 to the sides 12, 14 of the suburethral support 10, which extend on either side of the urethra.

Figure 6A:
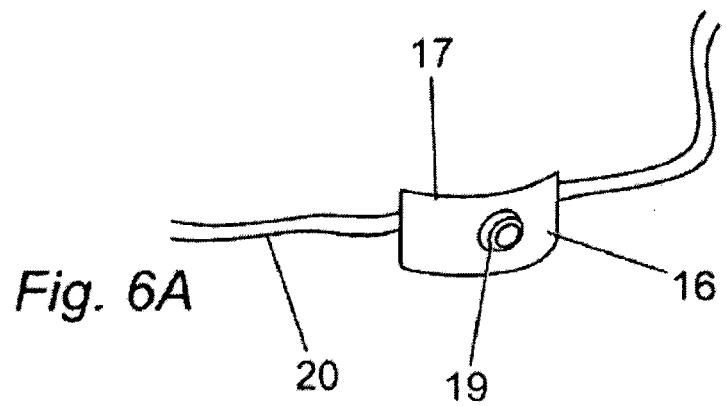
Figure 6B:
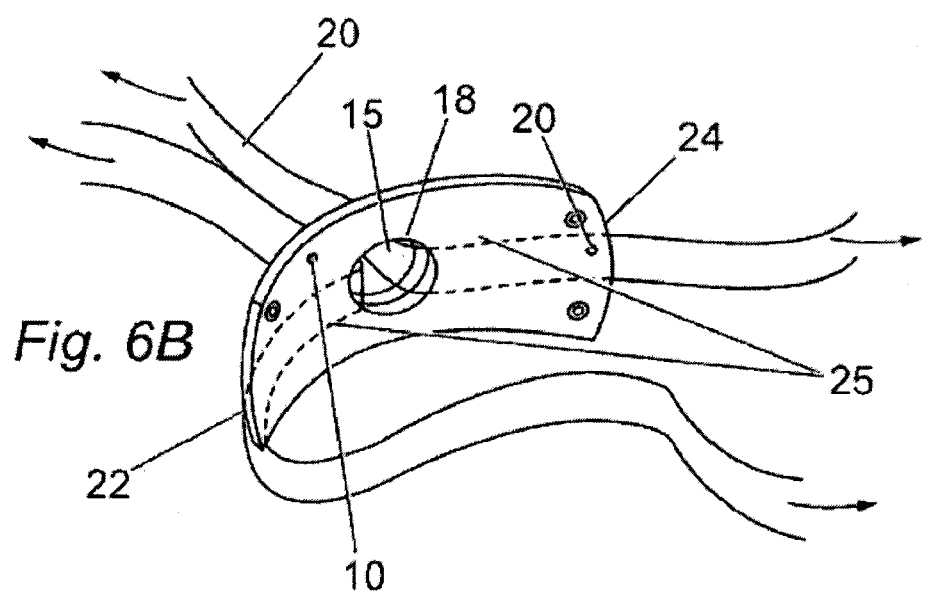
Figure 6C:
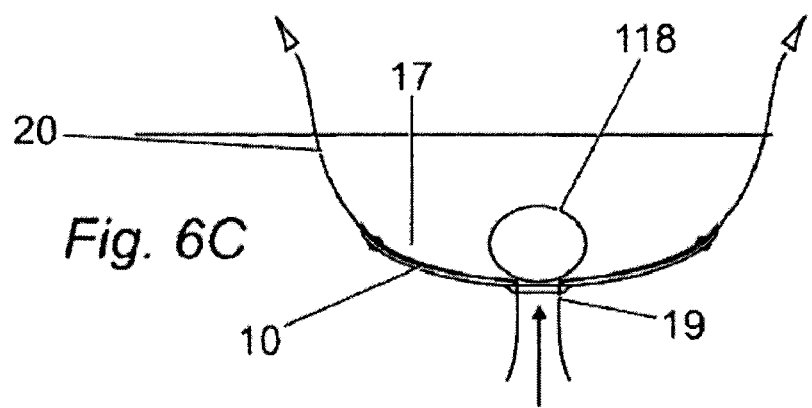

As shown in FIGS. 6a-6c a preferred method of altering the length of the suspending means 20 attached to the suburethral support 10 comprises a tunneled element 25 at each of the free ends 22,24 of the suburethral support 10 on either side of the urethra. The tunneled element 25 extends from the edges of the suburethral support 10 to an aperture 15, the aperture being present on the opposite surface 16 of the suburethral support 10 to the surface which contacts the urethra 17, the aperture 15 having an edge 18 able to co-operate with a ring element 19 such that the ring element which has memory can be pushed onto the edge 18 of the aperture 15 trapping the suspending means 20 between the edge of the aperture 18 and the ring element 19 thus securing the suburethral support 10 along a particular desired length of the suspending means 20 such that the suburethral support 10 hangs loosely under the urethra.

Figure 5:
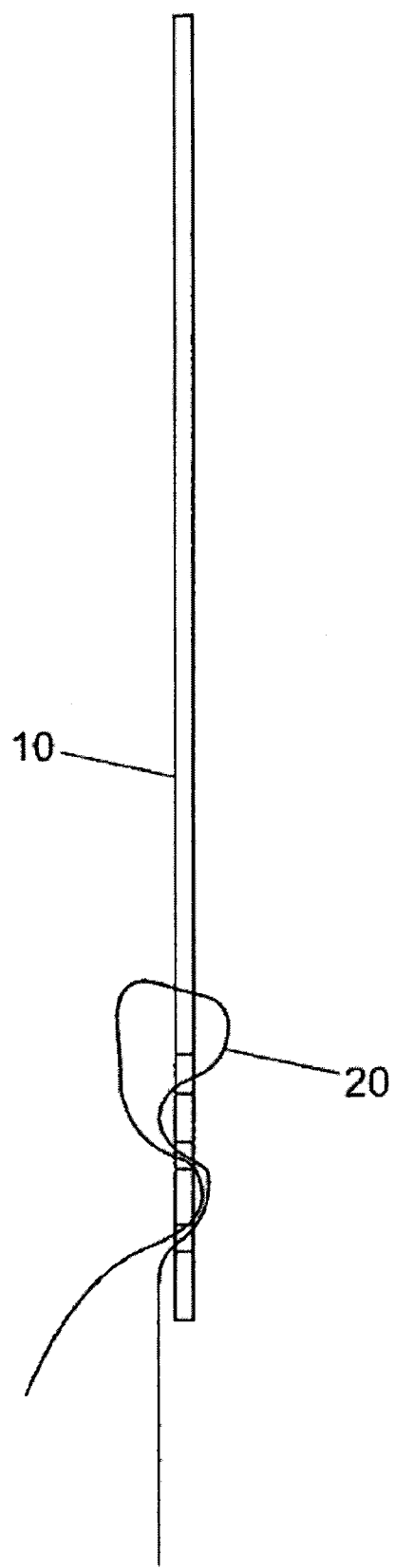
FIG. 5 shows suspending means being threaded through an attachment tab of a suburethral support, FIGS. 6A, B and C show alternative methods of attaching suspending means to a suburethral support.

FIG. 5 shows an alternative method of attaching the suspending means 20 to the suburethral support 10, the suspending means 20 being threaded through jamming slots 21 such that the suspending means 20 are permanently attached to the jamming slots 21 by being pulled into the jamming slots 21 as shown in FIG. 5 such that the suspending means is held tightly in position.

Alternatively as shown in FIG. 6 the suspending means 20 may be passed through slots and the suspending means permanently attached to the slots by tying.

Figure 11:
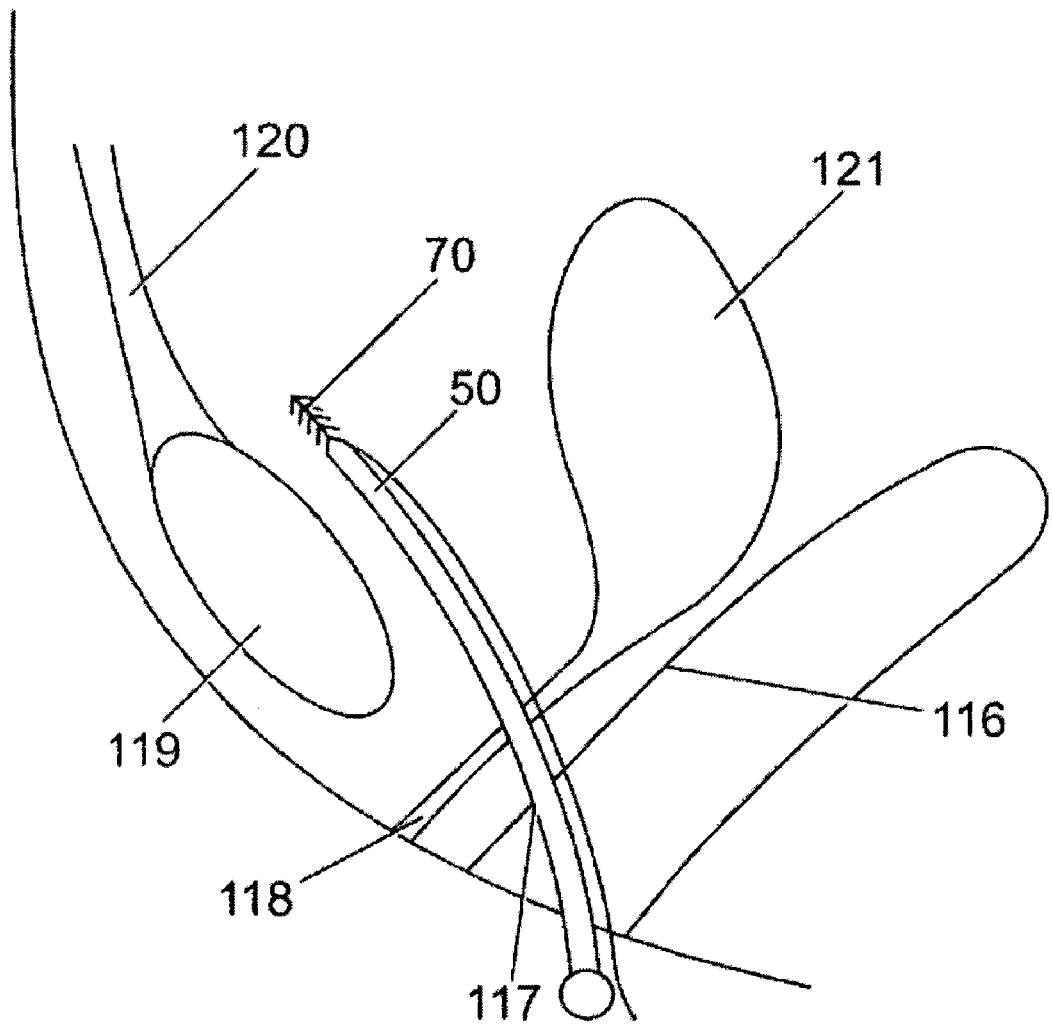
FIG. 11 is an illustration of the placement of a soft tissue anchor of FIG. 10.
Figure 12:
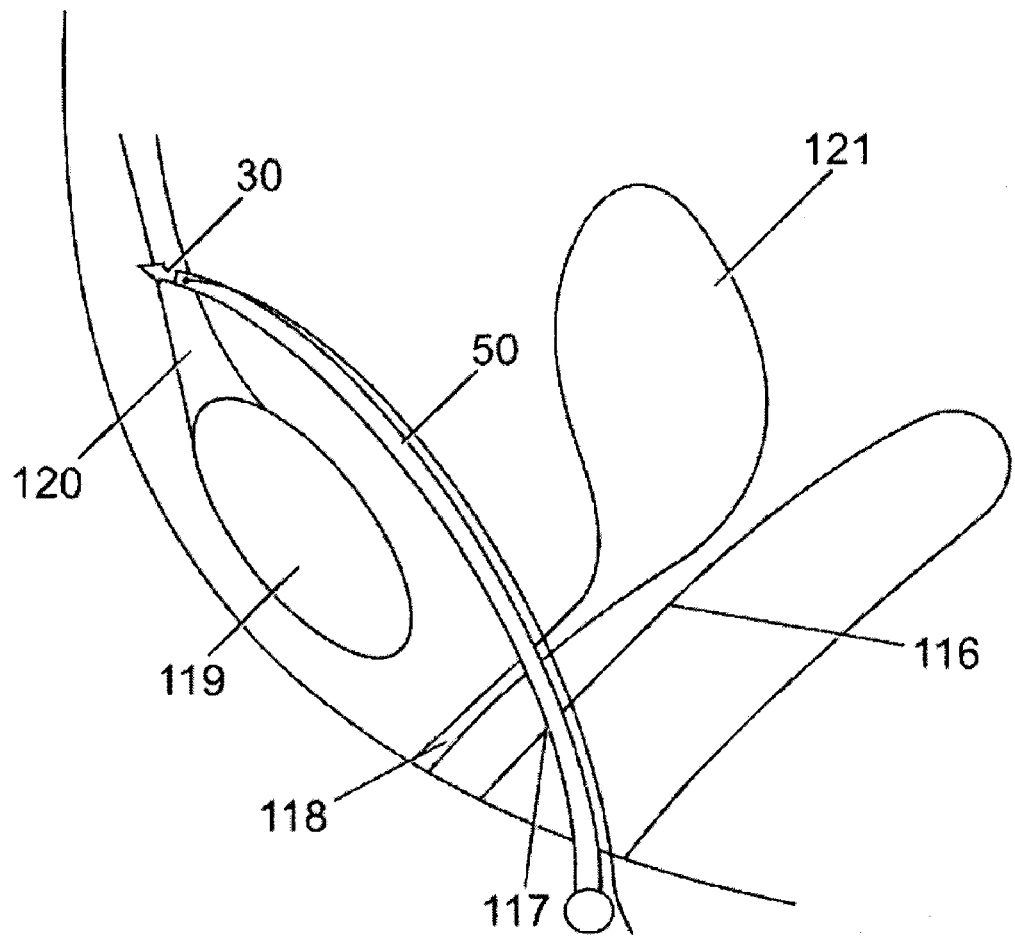
FIG. 12 is an illustration of an implanting tool and a soft tissue anchor inserted into the rectus sheath.

In use, as shown in FIG. 12 the soft tissue anchor 30 is placed on the introducing tool 50 as described above. An incision 117 is made in the upper wall 116 of the vagina, as shown in FIG. 11, and the introducing tool 112 is passed through the incision 117, past one side of the urethra 118, behind the pubic bone 119 and into the rectus sheath 120. It is apparent to the surgeon when the rectus sheath 120 has been penetrated as this stage of insertion presents significant resistance. Once the head 58 of the introducing tool 50 and the soft tissue anchor 30 have passed through the rectus sheath 120, the resistance diminishes and the surgeon ceases to insert the introducing tool 50.

Figure 13:
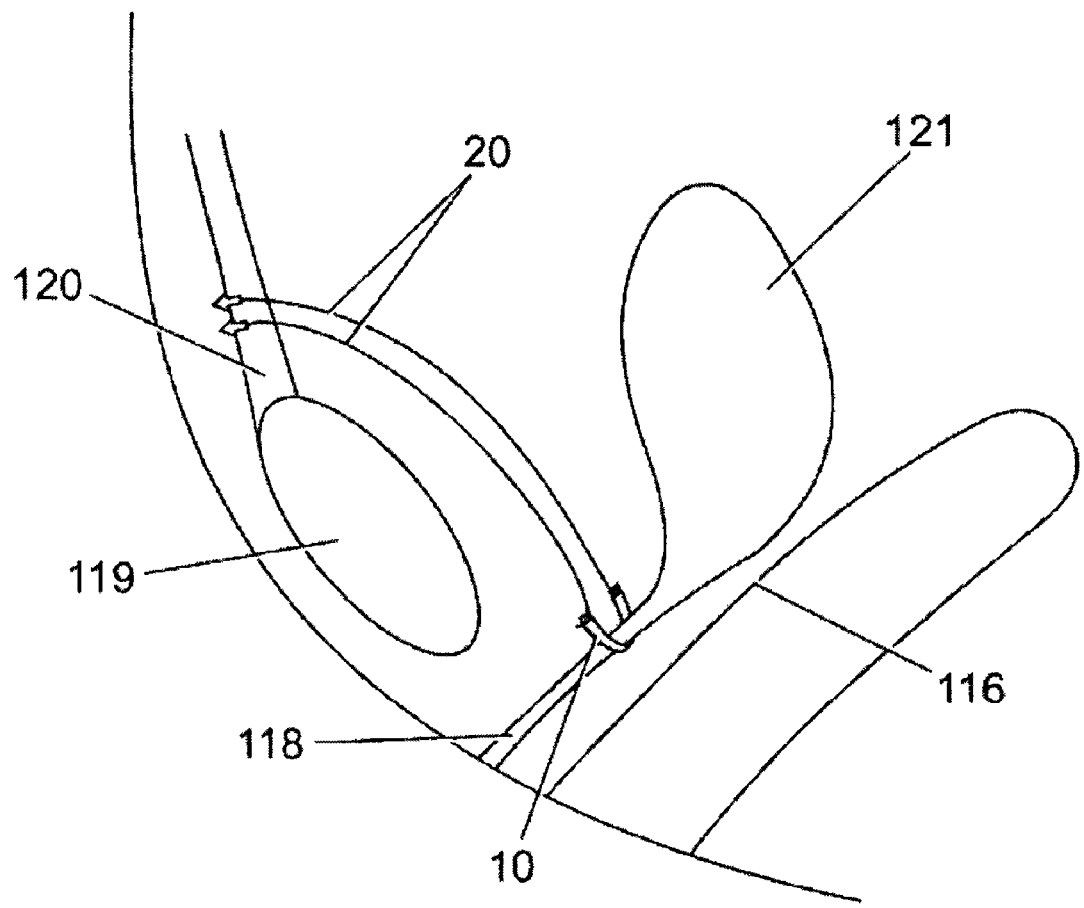
FIG. 13 is an illustration of the surgical implant implanted into the rectus sheath.

The introducing tool 50 is retracted from the body releasing the soft tissue anchor 30. Due to the wing sections 34 on the central portion 32 of the soft tissue anchor 30, the soft tissue anchor 30 is retained by the rectus sheath 120 as the introducing tool 50 is retracted. Thus, the suspending means remains in the body, secured by the soft tissue anchor which is opposed by the rectus sheath 120, as shown in FIG. 13.

This procedure is repeated, with a second soft tissue anchor 30 and suspending means 20, with the introducing tool 50 being passed through the incision 117 and past the other side of the urethra 118. Thus, two suspending means 20 are provided, attached to the rectus sheath 120, one passing either side of the urethra 118.

The suspending means 20 are passed through the tunneled elements 25 of the suburethral support 10, and the suspending means 20 are pulled through the aperture 15 until the suburethral support 10 is positioned such that it passes under the urethra 118. The suspending means 20 are then fixed in place by placing a ring element 19 over the edge 18 of the aperture 15 such that the suspending means are trapped between the edge 18 and the ring element 19 securing them in place.

Figure 14:
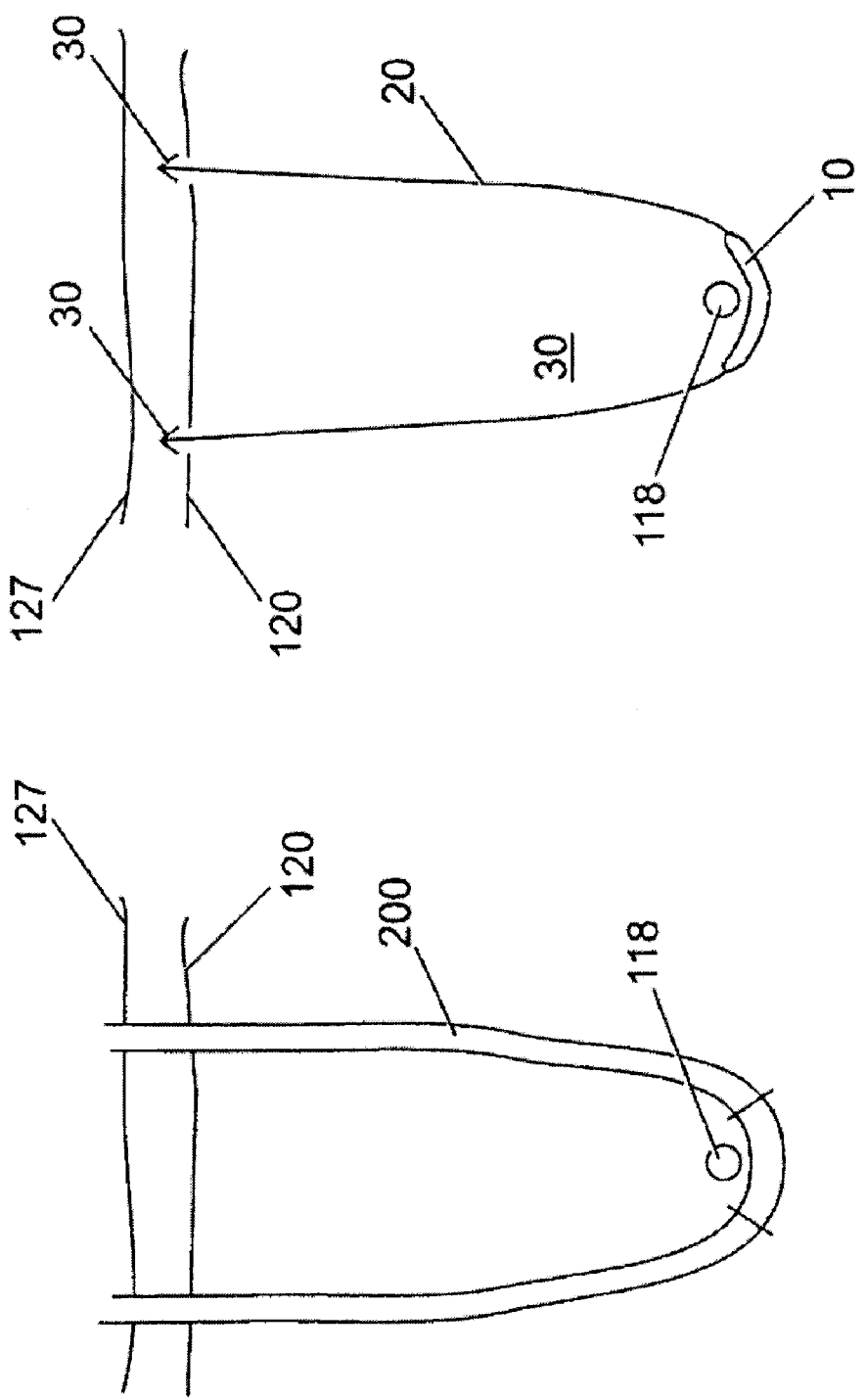
FIG. 14 is an illustration of the prior art contrasted with the technique wherein the anchor is inserted in the rectus sheath.

Alternatively as shown in FIG. 5 the suspending means may be fixed in the attachment tabs by threading them through jamming slots 21 or tying, as described above. The optimal lengths of the suspending means 20 are such that the suburethral support 10 passes under the urethra 118, but exerts no pressure on the urethra 118 unless the bladder 121 is displaced. The optimal positioning of the suburethral support 20 is roughly as illustrated in FIG. 14. When the bladder is displaced, the suburethral support 10 aids closure of the urethra 118, thus alleviating urinary incontinence.

In this example, a portion of the surgical implant is impregnated with methylene blue, which is a harmless water soluble dye. At the end of the procedure a small amount of fluid is expelled from the bladder 121. Should this fluid contain any dissolved methylene blue, it is very likely that the bladder has been perforated on placing the soft tissue anchor 30. In this case, cystoscopy should be carried out. If no methylene blue is present, the need for cystoscopy is advantageously obviated. Other suitable water-soluble dyes may, of course, be used.

Referring to FIG. 14, it can be appreciated that the surgical implant of the present invention, when inserted in the human body, may extend from the rectus sheath 120, through the paraurethral space 130 on one side of the urethra 118, around the urethra and back to the rectus sheath 120 on the other side. In contrast, the prior art device comprises a tape 200 that also extends through the abdominal wall 127 and represents a far greater implanted mass.

Figure 9:
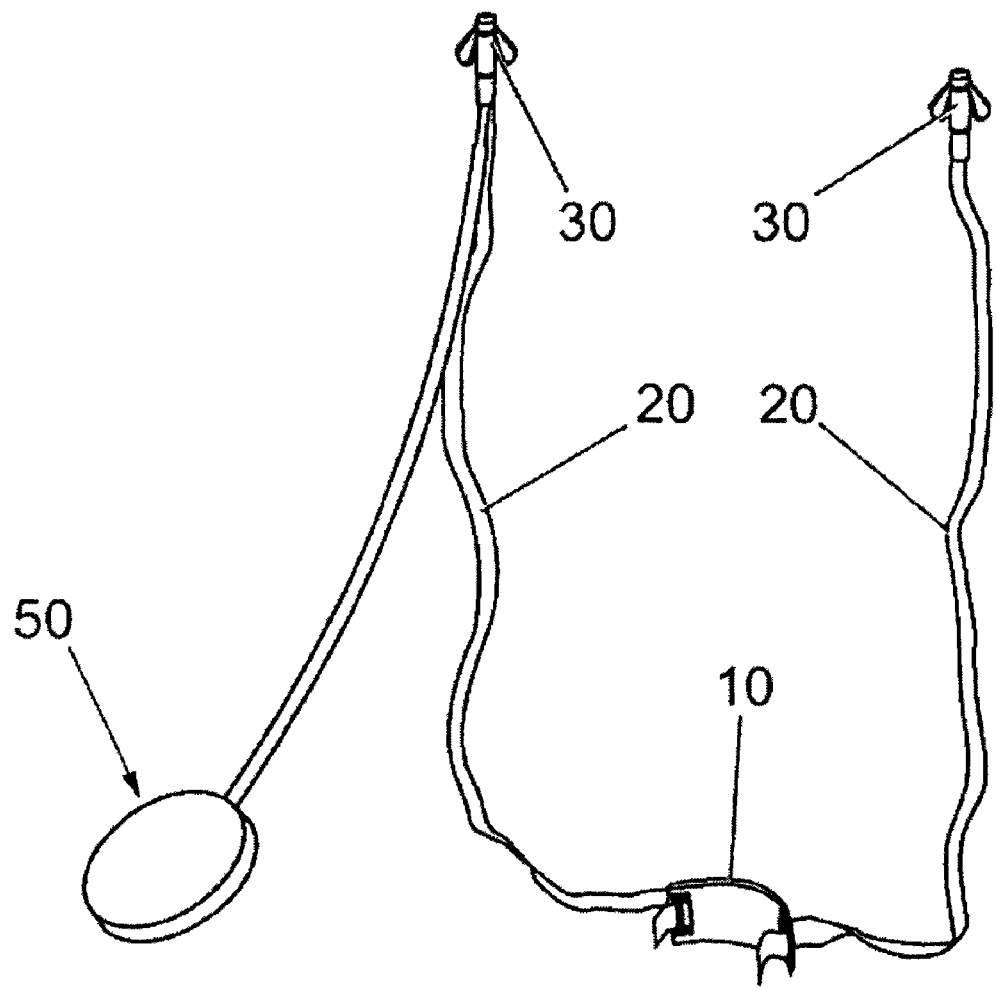
FIG. 9 is an illustration of a soft tissue anchor mounted on an introducing tool for insertion through the rectus sheath.

Referring to FIG. 11, in use, the further embodiment of soft tissue anchor illustrated in FIG. 9 for placement in fibro-fatty soft tissue of the retropubic space is placed on an introducing tool. An incision 117 is made in the upper wall 116 of the vagina, as shown in FIG. 11, and the introducing tool 112 is passed through the incision 117, past one side of the urethra 118, and located in the fibro-fatty soft tissue and blood vessels of the para-urethral tunnel. In this case the surgeon does not introduce the soft tissue anchor as far into the body as described previously and the rectus sheath 120 is not penetrated. Once the soft tissue anchor has been suitably positioned in the soft tissue the surgeon ceases to insert the introducing tool and retracts the introducing tool from the body releasing the projections of the soft tissue anchor 72. The release of the projections 72 of soft tissue anchor by the introducing tool allows the projections to grip the soft tissue surrounding the soft tissue anchor and provide resistance to movement of the soft tissue anchor in a direction opposite to that which it was inserted.

This procedure is repeated, with a second soft tissue anchor such that the projections 72 of the soft tissue anchor also provide resistance to movement of the soft tissue anchor in a direction opposite to that which it was inserted the introducing tool being passed through the incision 117 and past the other side of the urethra 118.

Thus, two suspending means 20 are provided, which are held in the soft tissue comprising fibro-fatty tissue and blood vessels.

As described above the suspending means 20 are passed through the attachment tabs of the suburethral support 10, and the suburethral support 10 positioned such that it passes under the urethra 118.

As described above, in one embodiment of the present invention, a soft tissue anchor(s) is inserted in and fixed in the soft tissue of the perineum.

Figure 21:
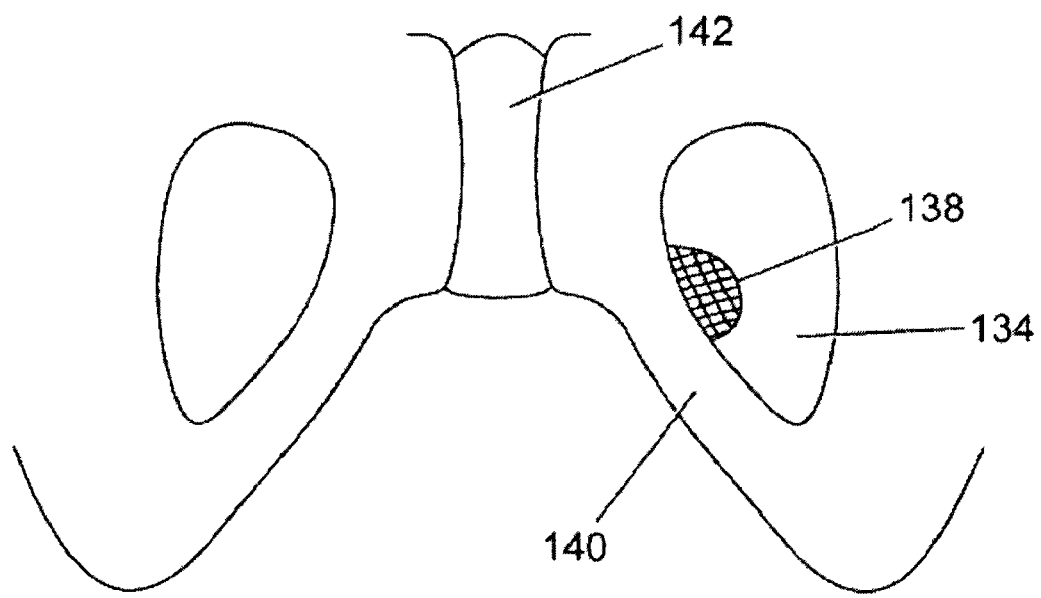
FIG. 21 is a diagrammatic representation of the anatomy of the pelvic region illustrating the obturator foramen, inferior pubic ramus, pubic symphysis and the safe transorbturator exit zone as used in prior art methods.

The perineum corresponds to the outlet of the pelvis inferior to the pelvic diaphragm (levator ani and coccygeus). The boundaries of the perineum are provided by the pubic arch and the arcuate ligament of the pubis; the tip of the coccyx; and on either side the inferior rami of the pubis (140) and ischium, and the sacrotuberous ligament. A line joining the anterior parts of the ischial tuberosities divides the perineum into two portions, the posterior anal triangle portion and the smaller anterior urogenital triangle. FIG. 21 is an illustration of the anatomy of the pelvis indicating the pubic symphysis (142), the inferior pubic ramus (140), the obturator foramen (134) and the region (138) of the obturator foramen though which devices of the prior art extend.

In this embodiment of the method of the present, the surgical implant does not penetrate or extend through the obturator foramen (134).

A surgical implant for use in the embodiment of the method wherein the soft tissue anchors are inserted in and anchor in the soft tissue of the perineum may be the same as the implant described in relation to the method of supporting the urethra by anchoring in the tissues of the retropubic space.

Figure 17:
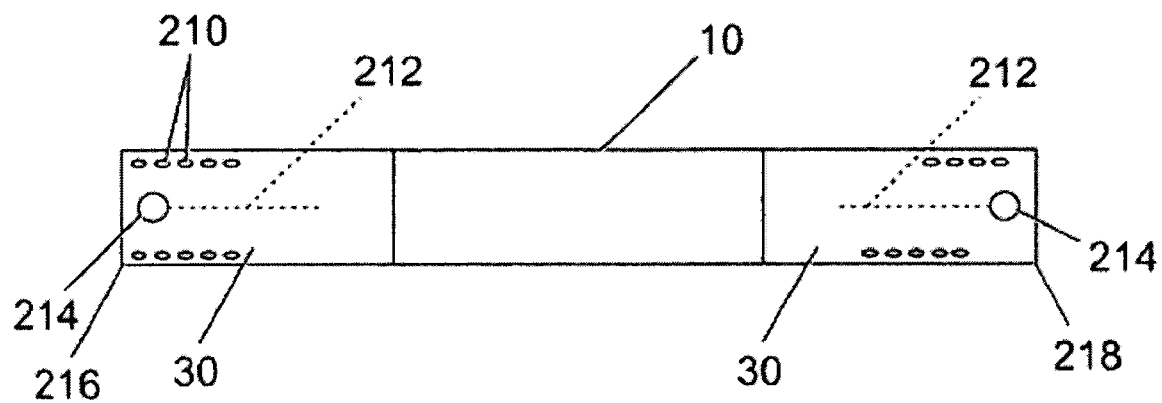
FIG. 17 illustrates a diagrammatic side view of an embodiment of an implant with portions of glue provided on the soft tissue anchors.
Figure 18A:
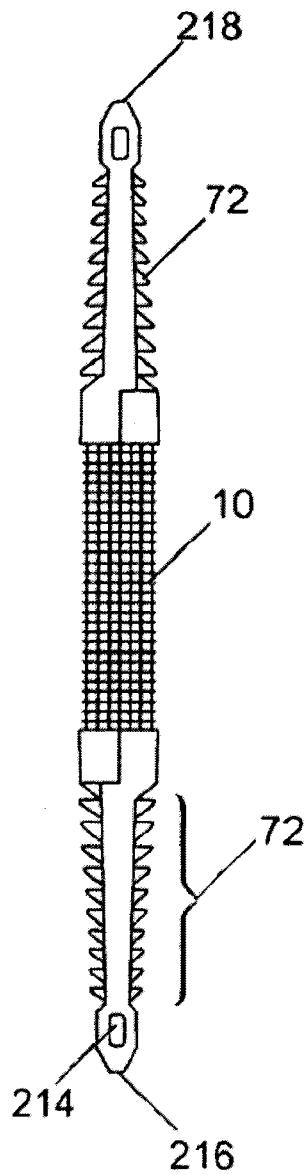
FIG. 18(a) illustrates an embodiment of an implant comprising a suburethral support formed from mesh.
Figure 18B:
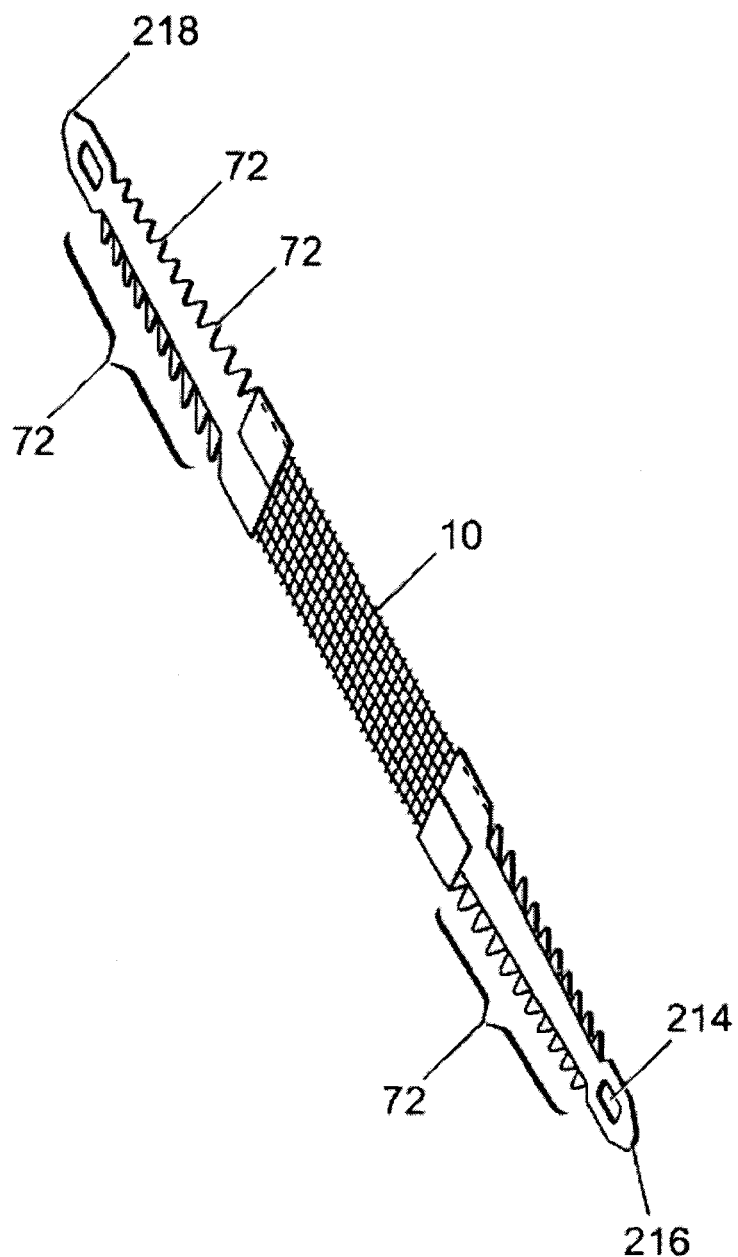
FIG. 18(b) is a further illustration of the embodiment of the implant of FIG. 18(a)

As illustrated in FIG. 17, in one embodiment of a surgical implant suitable for anchoring in the tissue of the perineum, the soft tissue anchors (30) are provided with glue (210) for fixation of the implant to the surrounding tissues. Prior to insertion, the implant may be curled or folded around a midline (212) of a soft tissue anchor (30) of the implant, and then a tool may be inserted through an aperture (214) at a first end of the implant (216) such that the implant can be inserted into the body via a vaginal incision (117) on an upper wall of a vagina (116). Once the first end (216) of the implant is suitably located in the soft tissue of the perineum on a first side of the urethra (118), the soft tissue anchor (30) may be uncurled such that the glue comes into contact with the surrounding tissue to adhere the tissue to the implant. The second anchor portion is then inserted through the vaginal incision and suitably located in soft tissue of the perineum on a second side of the urethra (118). The second soft tissue anchor may then be uncurled such that the glue comes into contact with the surrounding tissue to adhere the tissue to the implant.

Alternative embodiments of implants suitable for insertion into the soft tissue of the perineum are illustrated in FIGS. 18a, 18b, 19, 20, 28 and 29. As illustrated, the soft tissue anchor portions (30) can comprise projections, glue or a combination of glue and projections to allow anchorage of the soft tissue anchors in the soft tissue of the perineum.

Figure 19:
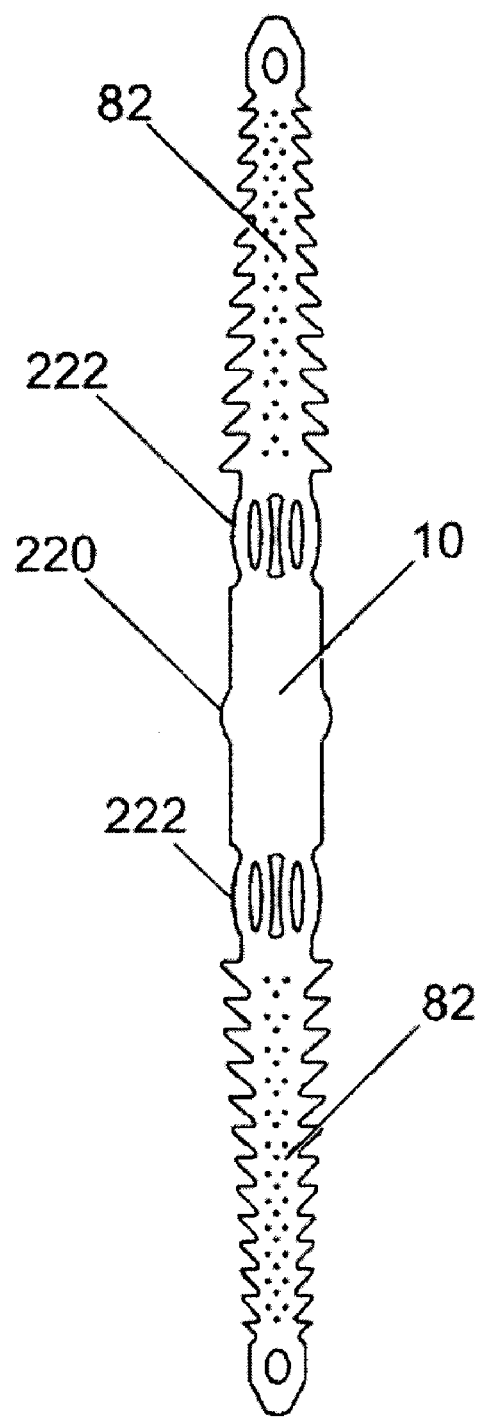
FIG. 19 is an embodiment of an implant comprising resilient zones.
Figure 20:
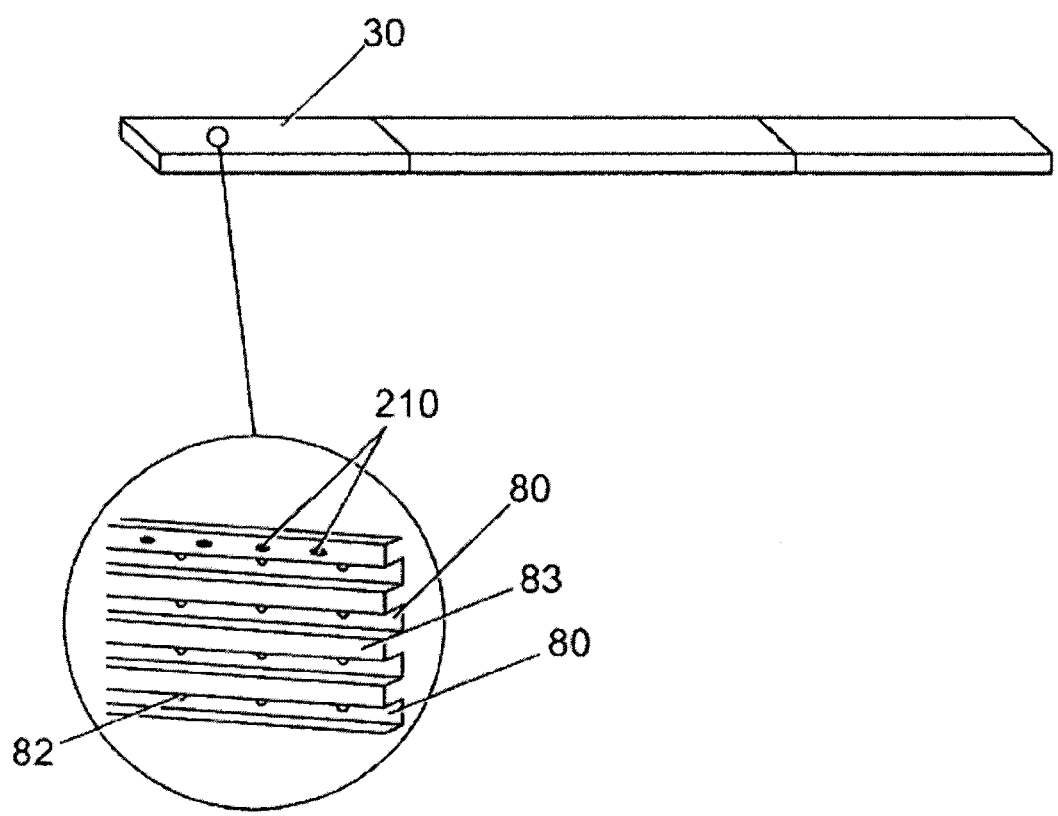
FIG. 20 illustrates a diagrammatic view of an implant wherein the soft tissue anchors are provided with grooves and pores and portions of glue.
Figure 28:
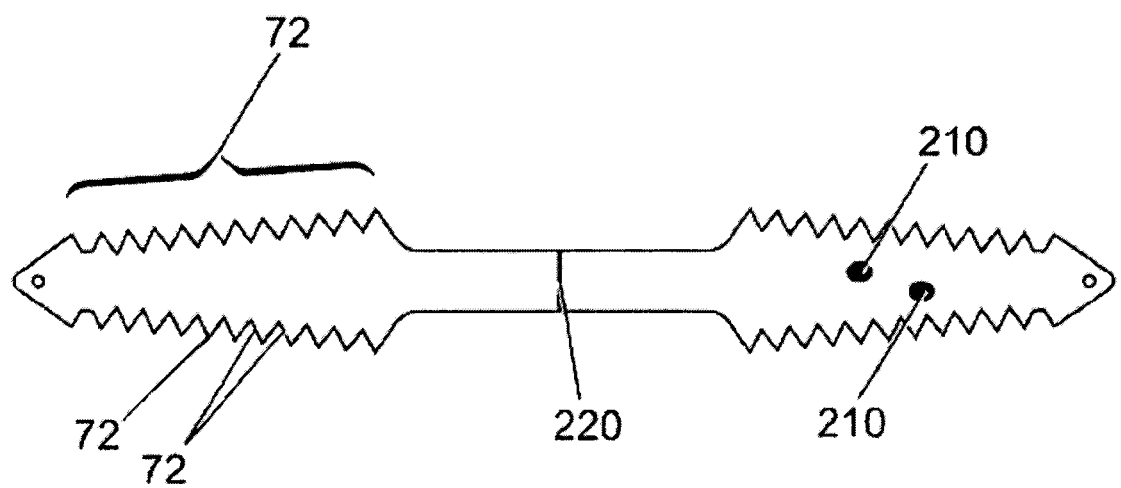
FIG. 28 illustrates an embodiment of a surgical implant comprising a marker on the suburethral support and soft tissue anchors comprising projections and glue.
Figure 29:
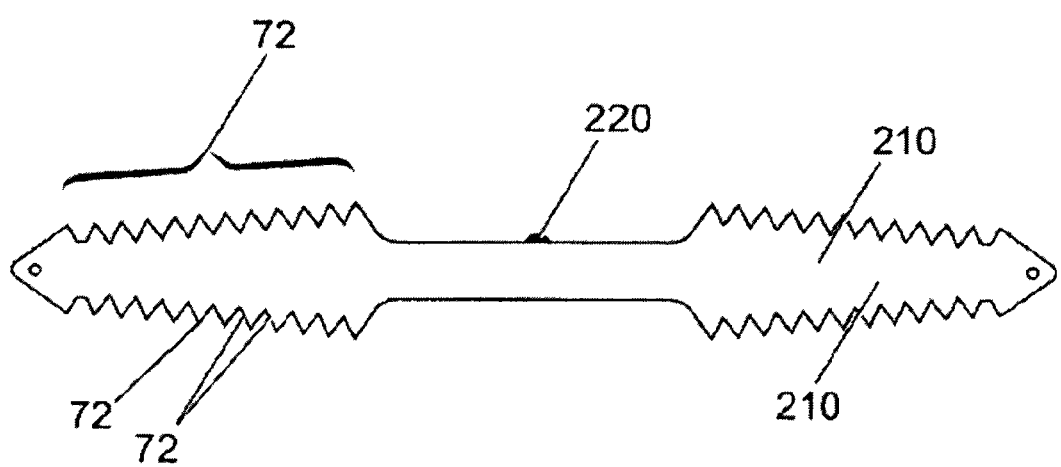
FIG. 29 illustrates a further embodiment of a surgical implant comprising a marker on the suburethral support.

As illustrated in FIGS. 19, 28 and 29, a marker (220) may be provided on the implant to aid location of the implant within the body following insertion. The marker may be, for example, a protrusion of the suburethral support, or a marked line on the implant. Other suitable means provided on the suburethral support to indicate the midpoint of the implant may be provided as would be appreciated to those skilled in the art.

As illustrated in FIG. 19, resilient zones (222) can be formed from several strip portions conjoined at a first end to the suburethral support and at a second opposite end to soft tissue anchor of the implant.

When not under tension these strip portions are bow shaped and are arranged such that they form a series of alternate and side by side convex and concave strips arranged in substantially the same plane as the implant.

On application of an extending force of up to 3 N to the implant along its length, the implant can show 2-3 mm of extension, as the bowshaped portions of the tape are pulled into straight strips, the ends of the bowshaped strips being brought together, enabling extension of the tape. The movement of the strips from the resting bowshape into the tensioned straight strips of implant allows the implant to resiliently extend along its length.

The maximum length to which the implant can be extended, is when the convex and concave strips are pulled such that these strips are brought into alignment with the longitudinal axis of the implant. Depending on the nature and length of the bow shaped portion, the extended length and the force required to promote extension of the implant can be controlled.

On release of the extending force these now straightened strips of implant of the resilient zone return to their previous non-extended bowshape causing the implant to resiliently return to its non-extended length.

The ability of the implant to show limited extension following the application of an extending force means that the implant more accurately mimics the movement of dynamic bodily tissue.

In order that the bowshape like portions of the implant can be pulled such that they are straightened, the material of the implant must be resilient to an extent, The amount of resilience of the material will influence the resilience of the implant to an extending force.

Figure 22:
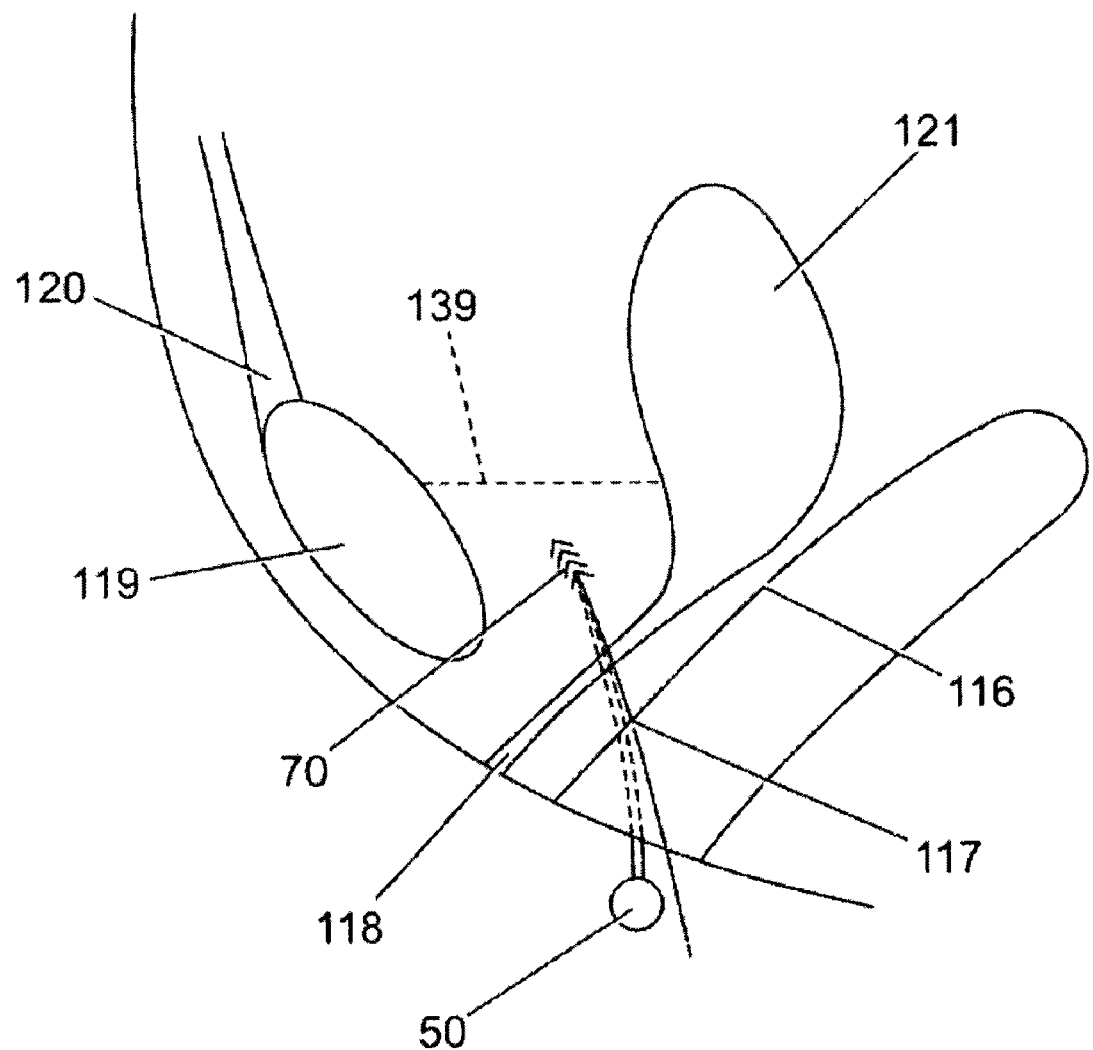
FIG. 22 is a cross-section illustration of FIG. 26 that illustrates insertion of an embodiment of a surgical implant wherein the soft tissue anchors are fixed in the soft tissue of the perineum.
Figure 23:
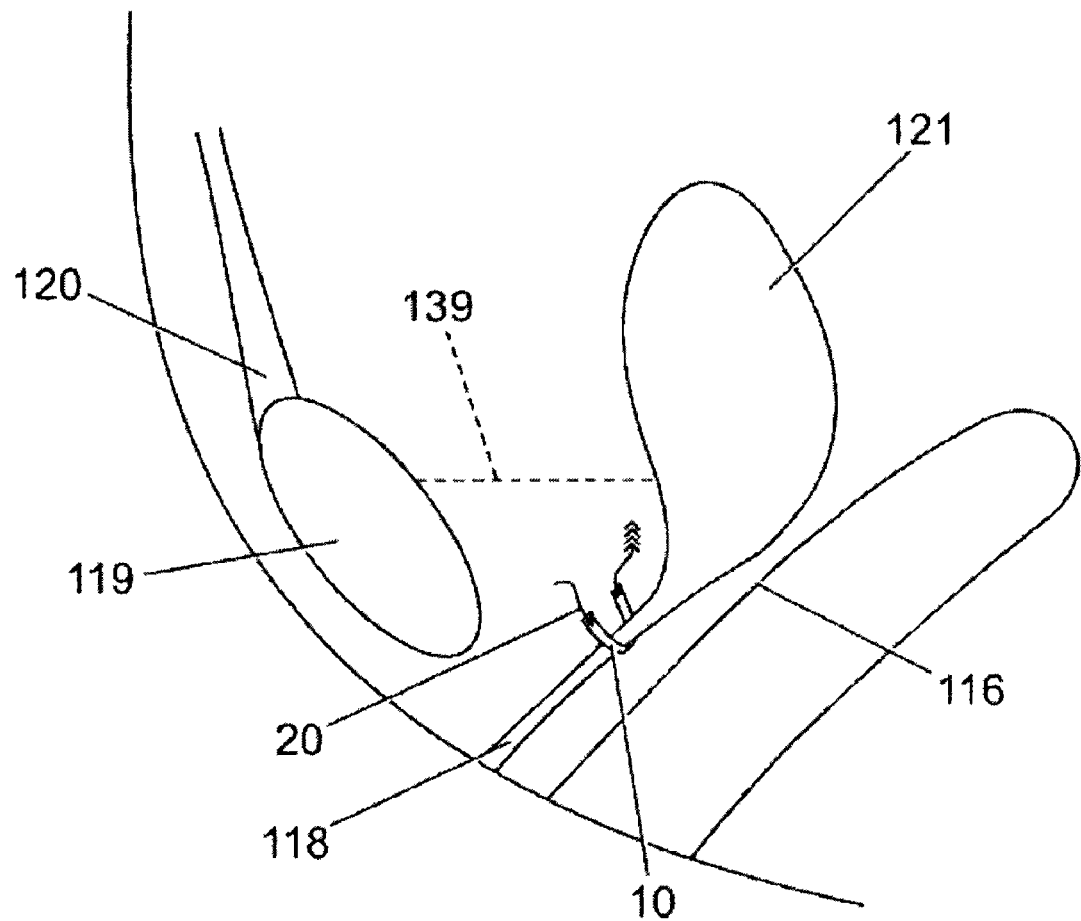
FIG. 23 is a cross-section illustration of FIG. 26 that illustrates an embodiment of a surgical implant wherein the soft tissue anchors are fixed in the soft tissue of the perineum.
Figure 24:
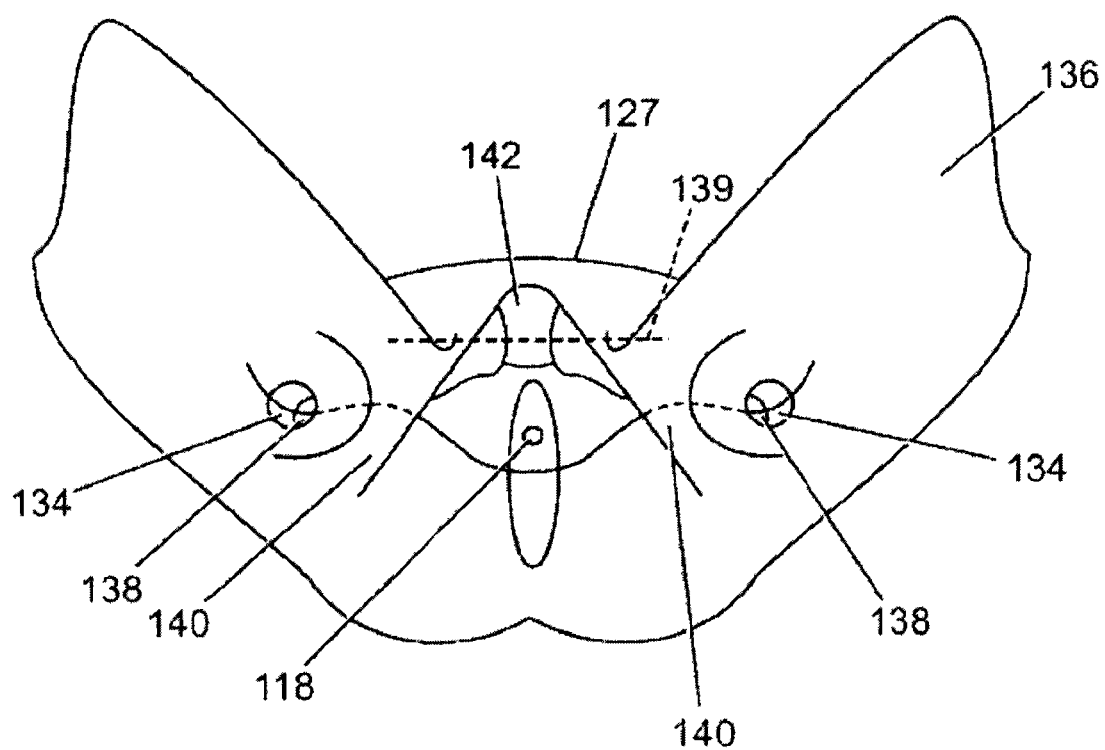
FIG. 24 illustrates a prior art device anchored in the skin above the obturator foramen.
Figure 25:
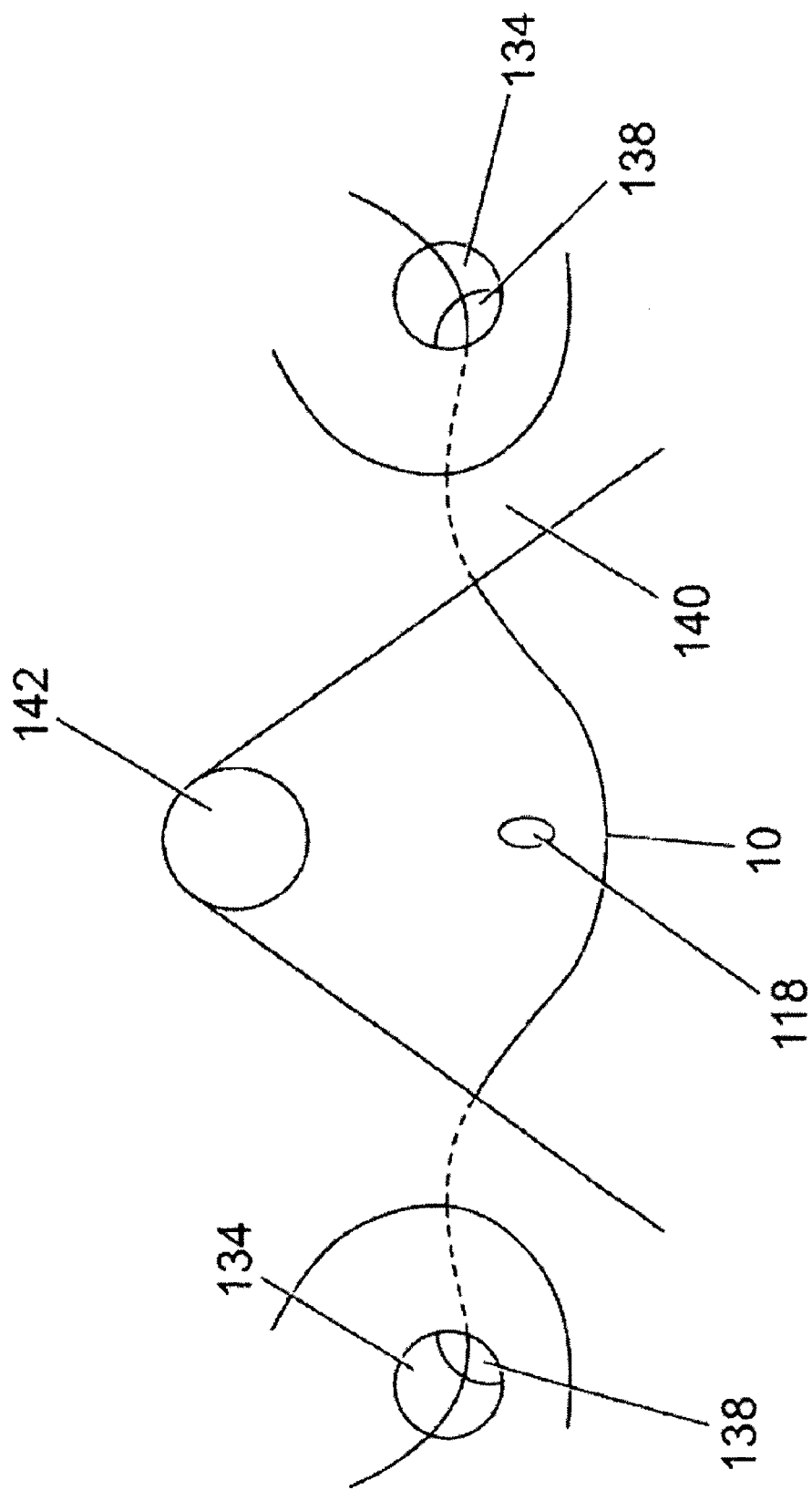
FIG. 25 illustrates a prior art device anchored in the skin above the obturator foramen.
Figure 26:
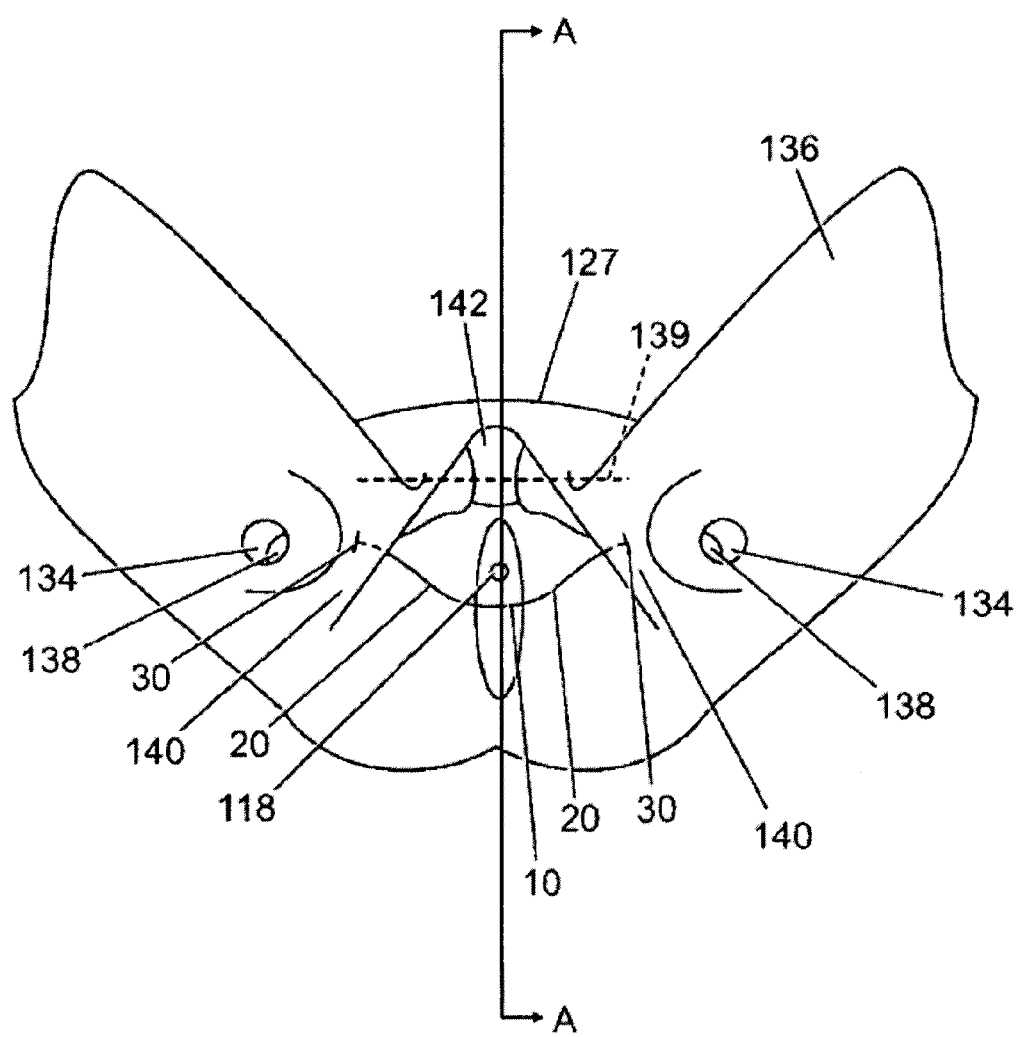
FIG. 26 illustrates placement of an embodiment of a surgical implant in the soft tissue of the perineum without insertion into the obturator foramen wherein the implant is in the body.
Figure 27:
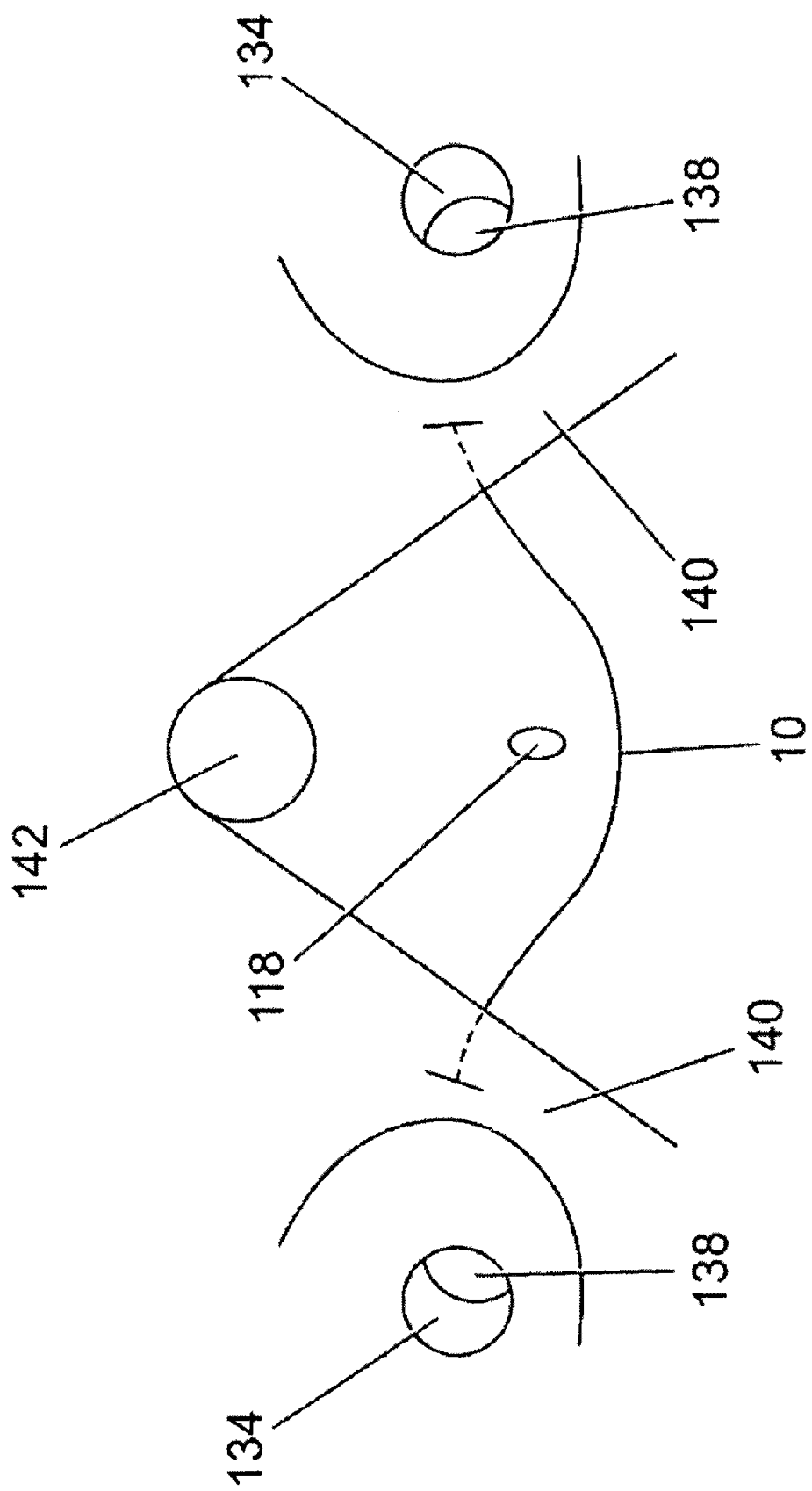
FIG. 27 illustrates placement of an embodiment of a surgical implant in the soft tissue of the perineum without insertion through the obturator foramen.

FIGS. 22, 23, 26 and 27 illustrate an embodiment of the method wherein the soft tissue anchors are inserted in and fix in the tissue of the perineum. It should be noted that FIGS. 22 and 23 are cross-sections of FIG. 26, taken along the line A-A. In accordance with one embodiment of the method, the patient is suitably placed in a modified lithotomy position with hips flexed and the legs (136) elevated. A small incision (117) is made in the upper wall of the vagina (116) followed by pariurethral dissection. A first soft tissue anchor (30) is inserted through the vaginal incision (117) and advanced laterally on a first side of the urethra (118), as illustrated in FIG. 27, into the tissues of the perineum towards and behind the inferior pubic ramus (140), but not through, the obturator foramen (134). The length of surgical implant which is to be inserted into the body for anchorage in the soft tissue of the perineum may be indicated by providing a marker on the implant. In an embodiment of a surgical implant for use in this method around 7 cm of the surgical implant is inserted on each side of the urethra.

The surgical implant and method for anchorage in the soft tissue of the perineum contrasts the devices and methods of the prior art in which the devices are required to be of sufficient length to extend through the obturator foramen (134) in a "safe" zone (138) close to the inferior pubic ramus (140) as illustrated in FIG. 21 and through the skin.

Provision of an implant capable of anchoring in the soft tissue of the perineum without requiring to pass through the obturator foramen is advantageous as it minimizes the likelihood of anatomical damage to nerves and blood vessels which may occur during procedures which penetrate the obturator foramen.

Following insertion of a first soft tissue anchor, a second soft tissue anchor is inserted into said vaginal incision on the second side of the urethra and then advanced in an opposing lateral direction to the first soft tissue anchor, as illustrated in FIG. 27, into the tissues of the perineum towards, but not through, the obturator foramen (134).

Suitably a centering marker (220) provided on the suburethral support is aligned under the urethra such that the first and second anchors are suitably provided into the soft tissue of the perineum.

In the embodiment of the method of locating the anchors in the soft tissue of the perineum illustrated, the soft tissue anchors are not anchored above the endopelvic fascia (139).

Again this device contrasts that described by the prior art device in that it does not extend through the abdominal wall or the obturator foramen and thus does not represent as much implanted mass.

Various embodiments of the present invention can be envisaged within the scope of the invention, for example the soft tissue anchor may comprise a cone or a half cone such that a circular or semi-circular base is provided as a retaining means to prevent retraction of the soft tissue anchor in a direction opposite to that in which it is inserted into the tissue.

Alternatively the soft tissue anchor may comprises a substantially flat or disc shaped head. In this case the introducing tool may have a conical head with a sharp point at its apex and a slot for receiving the flat or disc shaped head.

In yet another example, the soft tissue anchor may be formed of two sections. The upper section, i.e. the portion of the anchor that forms the sharp point 10, may be made from an absorbable material, such as polyglactin such that a sharp point is provided for insertion of the anchor into the body, but this sharp point is later absorbed by the body so as to eliminate any discomfort or disadvantage caused by a sharp pointed object being retained inside the body.

The soft tissue anchor may be made from metal, such as titanium, as this is a hard material that can easily be formed into the head having the sharp point at its apex, and is sufficiently malleable to provide a tube that may be crimped to the suspending means.

II.

Referring to FIG. 30 in one embodiment the surgical implant is a flat tape 192 which has a supporting zone 194 interposed between two fixing zones 196, the fixing zones being discrete zones of fixation extending from the supporting zone 194 to the first 198 and second 1910 ends of the tape 192 respectively. Apertures 1911 extend through the tape 192 approximate to the first and second ends of the tape 192. These apertures 1911 are of suitable size to allow a portion of an introducing tool to be passed through the apertures 1911.

The implant may be 14 cm in length and 1 cm in width, the supporting zone 194 being around 4 cm in length such that it is able to pass under the urethra.

In this example, the implant is made from flat polymer tape. The tape may be comprised of polypropylene. Alternatively all or portions of the tape can be mesh material. The tape need not be entirely flat and may have be curved in one or more directions for example to aid insertion of the tape or to ensure that the fixing zone does not interfere with elements contained in the retropubic space such as the bladder.

As shown in FIG. 32 the longitudinal edges 1930, 1932 of the fixing zone 196 may be tapered such that the width of the fixing zones increases from the first and second ends 198, 1910 of the fixing zones to the supporting zone. The tapered nature of the fixing zones 196 minimises disruption of the tissue of the retropubic space during placement of the tape 192 by the surgeon. The increasing width forms an arrowhead shape, the longitudinal edges of the tape extending from a point at a first and second end of the tape to the longitudinal edges of the support zone. The longitudinal edges extending from the point to the supporting zone may be serrated or notched to provide projections 1922 which in use extend into the tissues of the retropubic space.

The projections 1922 provide multiple points of contact between the tape 192 and the tissues of the retropubic space at multiple planes in the tissue.

The projections 1922 of the retaining means 1920 in the embodiment shown in FIG. 32 are curved such that they extend from the longitudinal axis such that in use the projections 1922 are not medially presented to the bladder 1942 which lies anterio-medially in respect to the passage of tape 192 in the body.

Further as shown in FIG. 32*b* the tape 192 may be of curved or of convex construction such that retaining means 1920 such as the projections 1922 face in a direction opposite or away from the bladder 1942 in use. The curvature of the tape 192 therefore ensures that the projections 1922 lie postero-laterally of the anterio-medial bladder position. This positioning minimises the possibility of bladder erosion by the tape 192 following placement.

The tape 192 of the supporting zone has smooth longitudinal edges to avoid adhesion of the supporting zone of the tape to the urethra.

This is advantageous as it discourages the formation of peri-urethral adhesions.

The polypropylene tape 192 of the fixing zone 196 comprises pores 1912, ranging in width from 50 µm to 200 µm, that extend through a first surface 1914 to a second opposite surface 1916 of the tape 192. The pores 1912 may be formed by post synthesis treatment of the fixing zones of the tape 192 with a laser.

The pores 1912 promote fibroblastic through-growth and lay down of tissue around and through the tape 192.

This aids integration of the fixing zone of the tape 192 to the tissue of the retropubic space.

The pores 1912 may alternatively be created by post synthesis treatment of the fixing zones 196 of the tape 192 by a laser.

In addition to the pores 1912, in the embodiment shown the fixing zone also comprises microgrooves 1918 of width 5 µm and of depth 5 µm. These microgrooves 1918 are shown present on one surface 1914 of the fixing zone of the tape 192, but may also be present on the opposite surface. In the embodiment shown the microgrooves 1918 are aligned such that they are substantially parallel with each other and separated by ridges 1924 of around 5 µm in width. It can be appreciated that the micogrooves may be arranged to create alternative surface patterns on the tape, depending on the direction of the laydown of tissue preferred.

The ridges 1924 are formed by square pillars, the base 1926 of the microgroove 1918 being substantially perpendicular to the square pillars.

Microgrooving can promote orientation and alignment of proliferating fibroblasts on the surface 1914 of the tape 192 of the fixing zone 196 and promotes axial alignment of collagen fibres and formation of at least one strong ordered neoligament. The orientation and alignment of the proliferating cells adds mechanical strength to the tissue which form around the tape such that these tissues support the urethra.

The supporting zone 194 of the tape 192 is preferably not provided with pores or pits to discourage the formation of peri-urethral adhesions. Micro-grooving is preferably provided only on the surfaces of the supporting zone not brought into contact with the urethra when the implant is in use.

As discussed, urinary incontinence may be caused if the pelvic floor muscles and connective tissue cannot support the bladder neck and mid-urethra, when pressure on the bladder is exerted from the diaphragm. Increased intra-abdominal pressure may occur at times such as coughing. The increased abdominal pressure results in the urethra descending from its normal position and failing to retain its seal, permitting urine to escape.

Previous apparatus and methods used for locating an implant such that the implant hangs loosely under the urethra have generally required that the implant be suspended from either the lower abdominal wall, the rectus sheath or other defined anatomical support structures. The suspension of an implant from defined anatomical support structure was thought necessary as the tissues of the retropubic space and endopelvic fascia were not deemed to provide enough resistance to allow appropriate location of an implant such that suitable support would provided to occlude the mid urethra at periods of raised abdominal pressure, by coughing or the like.

Surprisingly the Applicant has determined that suitable support can be provided by the tissues of the retropubic space, if fixation of the implant is achieved in the tissues of the retropubic space. Due to the tissue make up of the retropubic space, it was not previously considered that suitable fixation could be achieved in the retropubic space. Further it was not considered that suitable pressure transmission would be achieved to occlude the urethra, using a tape suspended from the tissue of the retropubic space, doing periods of increased abdominal pressure.

As shown in FIG. 36 the retropubic space 1940 is an extra-peritoneal tissue space lying behind the pubic bone. The retropubic space is defined by an anterio-superior boundary which is the peritoneum and rectus sheath 1944 and an interior boundary of endopelvic fascia 1946. The space defined by these boundaries is medially filled by the bladder 1942, the urethra 1948, fibro-fatty tissue and blood vessels. The blood vessels of the retropubic space generally become larger both in a superior and lateral direction within the retropubic space. The retropubic space approximately extends 8 cm from the endopelvic fascia to the rectus sheath, this distance varying by around 2 cm depending on the individual. The retropubic space comprises the same pressure compartment as the abdomen.

To locate the supporting zone 194 such that it passes loosely under the urethra 1960 it is required that the fixing zones 196 are fixed in the tissues of the retropubic space 1940 with as little tissue invasion as possible, but such that pressure transmission to the tape is maintained. A number of different retaining means can be envisaged including a Christmas tree design (a), a brush (b), a fish hook (c), a triple hook (d), an umbrella (e), one or more rods with memory (f), a corkscrew (g), an inflatable balloon (h), an inflatable flat star (i), a bear trap (j), a bulldog clip (k), a mesh cylinder (l), a buckie ball (m), a staple (n), a barbed portion of tape (o), a sponge (p) or fibre entanglement method (q) to secure the fixing zones of the surgical implant into the tissues of the retropubic space. Examples of these embodiments are shown in FIGS. 39*a* and 39*b*. It should also be noted that a plurality of retaining means may be located alone or in combination along a substantial part of the fixing zone.

As shown in FIG. 40 support to the urethra can be suitably gained by locating at least one anchor strip 1980 on either side of the urethra such that a first portion of the anchor strip 1982 extends into the retropubic space above the endopelvic fascia and is retained therein and a second portion of the anchor strip is located in the suburethral pressure space below the endopelvic fascia such that increases of intra abdominal pressure are transmitted to the pressure compartment containing the urethra and during periods of increased intra-abdominal pressure the urethra is occluded minimising incontinence. Retention of the first end of the anchor strip in the retropubic space is provided by retaining means.

In a first embodiment, retaining means 1920 are a plurality of projections 1922 extending laterally from the longitudinal axis of the implant. These projections 1922 are arranged along a substantial portion of the length of the fixing zone 196 such that when located in the tissues of the retropubic space they provide resistance at multiple levels within the fibro-fatty soft tissue and blood tissues of the para-urethral tunnel in a direction opposite to that in which the fixing zone 196 of the tape 192 is introduced into the tissues. This minimises movement of the tape out of the tissues of the retropubic space, even when a force is applied to the tape which acts to push or pull the tape out of the retropubic space.

Due to the multiple layers of fixation that can be achieved using the plurality of retaining means 1920 along a substantial length of the fixing zone 196 it is not necessary to insert the fixing zone through the rectus sheath 1944. This of significant advantage to the patient as puncture of the retropubic space requires considerable force by the surgeons and also requires larger, heavier needles leading to patient trauma. In addition the tissues around the rectus sheath are inervated leading to pain if these are punctured. The fixing zone 196 is movable within the tissues of the retropubic space by the surgeon during placement of the tape 192 to allow suitable positioning of the supporting zone 194 under the urethra. The retropubic space maximum sagittal length typically ranges between 6 cm to 10 cm defined by the boundaries discussed, thus the fixing zone 196 may be inserted at various positions within the fibro-fatty tissue of the retropubic space. The sagittal plane is that down the longitudinal length of the body. The approximate 8 cm length is the typical length of the retropubic space at the course of the paraurethral tunnel. Towards the pubic bone the retropubic space may be only 3 cm in length. This provides a means of adjustment of the position of the supporting zone 194 in relation to the urethra. The tape 192 may be moved by a surgeon during placement of the tape in the body into and out of the tissues of the retropubic space to suitably locate the supporting zone in relation to the urethra.

As shown in FIG. 32 the projections 1922 which form the retaining means 1920 are curved such that the points 1924 of the projections 1922 are directed away from the supporting zone and the bladder.

In a further second embodiment of the implant as shown in FIG. 32c, the implant further comprises resilient zones 197 interposed between the fixing zone and the supporting zone 194.

The two resilient zones 197 may comprise a geometric design of several strip portions conjoined at a first end to the supporting means and at a second opposite end to fixing means on the implant.

When not under tension these strip portions of tape material are bow shaped and are arranged such that they form a series of alternate and side by side convex and concave strips arranged in substantially the same plane as the tape.

On application of an extending force of up to 3N to the tape along its length, the tape can show 2-3 mm of extension, as the bowshaped portions of the tape are pulled into straight strips, the ends of the bowshaped strips being brought together, enabling extension of the tape. The movement of the tape from the resting bowshape into the tensioned straight strips of tape allows the tape to resiliently extend along its length.

The maximum length to which the tape can be extended, is when the convex and concave portions of the tape are pulled such that these strips are brought into alignment with the longitudinal axis of the implant. Depending on the nature and length of the bow shaped portion, the extended length and the force required to promote extension of the tape can be controlled.

On release of the extending force these now straightened strips of tape of the resilient zone return to their previous non-extended bowshape causing the tape to resiliently return to its non-extended length.

The ability of the tape to show limited extension following the application of an extending force means that the tape more accurately mimics the movement of dynamic bodily tissue.

In order that the bowshape like portions of the tape can be pulled such that they are straightened, the material of the tape must be resilient to an extent, The amount of resilience of the material will influence the resilience of the tape to an extending force. In addition, the micro material design of the material of the tape can be used to limit or promote the resilience of the tape to an extending force.

Micro material design includes the way in which the tape material is woven, knitted of formed such that the tape material is resilient and allows extension along a particular axis.

Different geometric designs to allow extension of the implant in particular directions can be envisaged, for example folding of the tape would provide a concertina design which would allow resilient extension of the table in a direction substantially perpendicular to the folding.

This further embodiment of the implant shown in FIG. 32C also shows elongate slits in the fixing means of the tape. These elongate slits are of 1 mm in length and 50 to 100 μm in width. The elongate slits allow fibroblast through growth into the tape, securing the tape to the tissues.

As shown in FIG. 32c the implant can further comprise a protrusion of fabric 199 which extends laterally from the longitudinal edges of the supporting zone member to indicate to the surgeon the midpoint in the length of the tape to aid the surgeon in locating the implant under the urethra.

The inclusion of the resilient zones within the implant, shown in FIG. 30, provides the implant with limited extension following location of the fixing zones in the retropubic tissues on either side of the urethra. As the supporting zone which lies underneath and supports the urethra can show limited extension, the urethra is therefore supported in a more similar manner to that as when it is supported by dynamic bodily tissue.

The embodiments of the implant described herein may be suitably located in the tissues of the retropubic space using an introducing tool.

As shown in FIG. 35 one embodiment of the introducing tool 1950 comprises a handle 1952, an elongate shaft 1954 and a semi-blunt point 1956, the handle 1952 being located at a first end 1958 of the elongate shaft 1954 and the semi-blunt point 1956 being located at a second end 1960 of the elongate shaft 1954. The elongate shaft 1954 is curved through an angle of approximately 30° to facilitate positioning of the fixing zone 196 of the implant in the tissues of the retropubic space of the human body from an incision in the upper wall of the vagina. A narrowed portion 1962 of the elongate shaft 1954 extends from the semi-blunt point 1956 toward the handle 1952. An abutment 1964 is formed where the shaft widens from the narrowed portion. The narrowed portion of the tool is able to be passed through the aperture 1911 present in the fixing zones 196 of the tape 192. The abutment 1964 prevents the movement of the tape 192 down the full length of the elongate shaft 1954 such that the tape 192 is retained on the narrowed portion 1962 of the elongate shaft 1954, the semi-blunt point 1956 extending through the aperture 1911 in the tape 192.

An alternative embodiment of the tool, shown in FIG. 36 comprises a recess 1970 which extends from the semi-blunt point 1956, the recess being adapted to receive a fixing zone 196 of the implant. The recess may be angled or offset such that when the fixing zone of the tape is positioned in the recess 1970 of the tool, the tape is twisted along its longitudinal length such that on placement of the tape within the tissues of the retropubic space the projections of the fixing zone face postereo-laterally of the anterio-medial bladder position. FIG. 37 shows an illustration of the direction of the retaining means in relation to the bladder.

Further the tip of the tool may be offset such that one portion forming the wall of the recess extends further than the other portion forming the recess. This allows easier positioning of the tape into the recess.

The introducing tool 1950 may be comprised of any suitable material. In the embodiments shown the tool 1950 is 8 cm in length and 2-3 mm in diameter and is comprised of hard plastic. The tool may be disposable or capable of being sterilised.

With regard to the first embodiment of the tool, in use the semi-blunt point 1956 is passed through the aperture 1911 in the tape 192 such that the tape 192 rests on the abutment 1964 preventing the tape 192 from moving further down the elongate shaft 1954 of the tool 1950. The tape 192 is rolled about its longitudinal axis such that the edges 1930, 1932 are brought toward each other. The tape 192 is restrained in this rolled position. The tape 192 may be restrained by the surgeon or by an envelope placed over the rolled tape. An envelope placed over the rolled tape may comprise a medial defect, which allows removal of the envelope when the tape is suitably positioned, by pulling the tape through the defect in the envelope.

The rolled fixing zone 196 of the tape 192 is inserted via an incision in the anterior vaginal wall, past one side of the urethra and into the retropubic space. Ideally insertion of the fixing zone 196 into the tissues of the retropubic space should be as limited as possible, but sufficient to allow suitable location of the fixing zone 196 and adequate pressure transmission to allow occlusion of the urethra. Following insertion of the first end of the tape 192, the fixing zone 196 may be moved within the tissues of the retropubic space by the surgeon such that the fixing zone 196 is suitably located in the fibro-fatty soft tissue. Withdrawal of the introducing tool 1950, described above, causes the narrowed portion 1962 of the tool 1950 to be retracted from the aperture 1911 of the tape 192. This causes release of the tape 192 from the tool. The tape may also be released from its restrained position by the surgeon. As the implant is formed from resilient material, which has memory, release of the implant from its restrained rolled position causes the longitudinal edges 1930, 1932 to expand outwards, away from each other, from the rolled position such that the retaining means, the plurality of projections 1922 at multiple layers, are pushed into the surrounding tissues of the retropubic space.

This causes projections to enter the retropubic tissue at multiple levels. Although the force required to move one projection through the tissue of the retropubic space may be small, the multiple projections, cause a additive effect and increase the force required to move the tape from the tissue of the retropubic space.

With regard to the second embodiment of the introducing tool discussed, in use, an aperture 1911 in the tape 192 is passed over the semi-blunt point 1956 such that a portion of the fixing zone 196 of the tape 192 is retained in the recess 1970, while the rest of the tape 192 comprising the supporting zone and a second fixing zone lies along the longitudinal length of the tool. As discussed, the recess 1970 of the introducing tool may be angled such that the fixing zone 196 retained within the recess 1970 is orientated such that on placement of the fixing zone 196 in the tissues of the retropubic space the retaining means 1920 of the fixing zone 196 face away from the bladder to minimise the risk of erosion of the bladder by the retaining means.

Introduction of the implant into the body using the second embodiment of the tool described is similar to that previously described. Release of the fixing zone 196 of the tape 192 from the recess 1970 is performed by withdrawal of the tool.

The serrated arrowhead shape of the fixing zone of the embodiment described, means that as the fixing zone is pushed into a suitable location by the surgeon using the introducing tool, the distortion of the tissue in which the fixing zone is to be placed is minimised. This ensures that the retaining means of the fixing zone is provided with suitable tissue in which to obtain multi-level fixation. The fixation being of adequate tensile strength against cough until fixation of the implant by tissue through-growth occurs.

Following insertion and suitable placement of the fixing zone 196 of the tape 192, penetration of the fibro-fatty tissue by the multiple projections 1922 occurs at multiple levels in the tissue and increases the grip of the retaining means 1920 on the fibro-fatty soft tissue of the retropubic space. As the entry of the retaining means 1920 is active and not passive, actively inserting the retaining means 1920 into the tissue, the gripping effect of the plurality of the projections 1922 is increased. A second fixing zone comprising retaining means 1920 as described for the first fixing zone is rolled such that the longitudinal edges 1930, 1932 are brought toward each other. The implant is restrained in this rolled position and inserted through the same incision in the vaginal wall as the first fixing zone, past the other side of the urethra to that of the first fixing zone and the rolled second fixing zone 196 released to allow the retaining means to grip the tissues of the retropubic space. The supporting zone 194 of the tape 192 being suitably located and held in position by the fixing zones 196 under the urethra to provide support to the urethra. In such a suitable portion the supporting zone is able to occlude the urethra at periods of increased abdominal pressure and thus minimise urinary incontinence.

In a second embodiment of the present invention retaining means are provided by glue.

Suitable glue such as cyanoacrylate glue or butyl acrylate glue may be applied to the fixing zone 196 of the tape 192. The glue is not applied to the supporting zone 194 of the tape 192, to ensure that the supporting zone 194 does not bind to the urethra.

In use cyanoacrylate glue is applied along a substantial length of a first fixing zone 196 of the tape 192 and this first fixing zone 196 is inserted through an incision in the anterior vaginal wall, past one side of the urethra into the retropubic space. Following insertion of the first end 198 of the implant such that the fixing zone 196 is suitably located in the fibro-fatty soft tissue of the retropubic space, the tape 192 is held to enable an adhesive bond to form between the fixing zone 196 of the tape 192 and the tissues of the retropubic space. As the glue is applied along a substantial length of the first fixing zone 196, the first fixing zone 196 adheres to the fibro-fatty soft tissue of the retropubic space at multiple layers providing suitable resistance.

Cyanoacrylate glue can then be applied along a substantial portion of a second fixing zone 196. The second fixing zone 196 can then be inserted through the same incision in the vaginal wall and past the other side of the urethra such that the supporting zone 194 is located to provide support to the urethra. The glue may be provided within dissolvable spheres which will coat the glue during entry of the tape into the body, the coating dissolving when the implant is suitably located such that the glue can adhere the tape to surrounding tissues.

The glue to adhere the fixing zones of the implant to the tissues of the retropubic space may be provided in capsules or releasable containers mounted or attached to the implant. Once at least one of the fixing zones of the implant has been suitable positioned in the tissues of the retropubic space the capsules containing the glue can be burst using suitable means. For example, the capsule may be burst using a sharp point present on the introducing tool. Alternatively withdrawal of the introducing tool from the retropubic tissues may rupture or burst such capsule or promote the opening of the releasable containers such that the glue contained in the capsule or container is able to adhere the fixing zone of the implant to the surrounding tissues.

Where glue is use to adhere the fixing zone of the implant to the surrounding tissue, the fixing zone may be smaller than the dimensions listed above. Use of glue to fix the implant in the tissues of the retropubic space provides multilevel fixation of the implant. Other methods or means to allow release or activation of the glue, for example heat, can be envisaged by those skilled in the art.

Further embodiments of retaining means can be envisaged such as swelling hydrogels such as gelatin, polysaccharides or Hyaluronic acid. These may be applied to the fixing zone 196 of the implant, such that following introduction of the fixing zone 196 of the implant into the body the hydrogel expands, providing resistance in a direction opposite to that in which the fixing zone 196 of the implant is introduced into the tissues, suitably locating the supporting zone 194 to support the urethra.

In addition retaining means may be substances which have properties changed by heat, cold or light that may be applied to the fixing zone 196 of the implant such that on suitable treatment of the implant, the fixing zone 196 of the implant becomes suitably fixed in tissues of the retropubic space.

The length of the implant of the present invention is considerably less than that described in the prior art, which is typically 25 to 28 cm in length. This is of considerable advantage as the amount of foreign material placed in the body is reduced, decreasing the risk of inflammation and other problems associated with leaving foreign material in the human body for periods of time.

In addition as the present invention does not require the highly innervated and tough structures of the lower abdomen wall or rectus sheath to be punctured, which require considerable force to be applied by the surgeon, to enable location and fixing of the implant the trauma suffered by the patient is considerably reduced. Due to the decreased trauma suffered by the patient the above procedure may be carried out under local anaesthetic in an outpatient or office setting.

As a greater number of major blood vessels are found located in the retropubic space toward the rectus sheath, suitable placement of the anchor lower in the retropubic space minimises damage to blood vessels, reducing the amount of blood which might be lost by the patient.

Further, as there is not a requirement to anchor the fixing zone of the tape toward the rectus sheath, staying medially the tape can be placed lower and more laterally in the retropubic space toward the endopelvic fascia this reduces the chance of damage to anatomical structures such as the bladder. In view of the decreased risk of damaging the bladder the described procedure may be performed without the need for per operative cystoscopy. This reduces the overall time taken to perform the procedure, further reduces the pain and trauma suffered by the patient and reduces the expense of the procedure.

Referring to FIG. 41, a surgical implant for treating female urinary incontinence has a suburethral support 2010, suspending means 2020 and at least two soft tissue anchors 2030, the suburethral support 2010 being positioned in use, loosely under the urethra. The suburethral support has a length L of around 25 mm and a width W of around 10 mm such that it passes around the urethra with a minimum of excess material, although other similar dimensions would also be suitable. In this example, the suburethral support 2010 is made from flat polymer tape. At each side 2011,2013 of the suburethral support 2010 suspending means 2020 are provided which attach to the suburethral support 2010 at a first end 2022, 2024.

The suspending means 2020 are attached at a second end 2026 to a respective soft tissue anchor 2030.

As shown in FIG. 47 the soft tissue anchor 2030 of the embodiment described comprises a central portion 2032 and four winged sections 2034 which are attached to the central portion at a first end 2038 by resilient hinge means 2036 and radially extend from the central portion 2032 such that when viewed from the front the anchor device resembles a cross.

As shown in FIG. 48A the wing sections 2034 of the soft tissue anchor 2030 having a resting position in which they are inclined towards the rear 2040 of the central portion 2032 at an angle of around 45°. In FIG. 48B during penetration of the anchor through tissue (the point 2060 of the introducing tool enabling the soft tissue anchor to be pushed through the tissue and rectus sheath 20120) the wing sections 2034 of the soft tissue element 2030 may adopt a deflected position which means the penetration of the soft tissue anchor through the tissue and rectus sheath 20120 is more effective.

As shown in FIG. 48C once the rectus sheath 20120 has been pierced the resilient hinge means 2036 cause the wing sections 2034 to return to their resting position.

Movement of the soft tissue anchor in a direction opposite to which it was introduced into the soft tissue causes the wing section to be deflected until an endstop 2046 is reached which prevents the wing sections 2034 moving beyond a point substantially perpendicular to the central portion 2032 and prevents retraction of the soft tissue anchor 2030 from the soft tissue.

The soft tissue anchor 2030 further comprises a hollow portion 2048 which extends from the first end 2038 to the second rear end 2040 of the central portion 2032 through which an introducing tool 2050 may be placed.

The introducing tool 2050 extends through the hollow portion 2048 such that it extends as a sharp point 2060 from the first end 2038 of the soft tissue anchor 2030 such that the sharp point 2060 allows penetration of the tissue by the soft tissue anchor 2030.

Stud like projections 2042 which extend radially from the central portion 2032 are angled such that they extend further radially from the central portion 2032 as they extend towards the rear 2040 of the central portion 2032, this inclination allowing the soft tissue anchor 2030 to pass more easily into the soft tissue.

A recessed portion 2044 is positioned toward the rear end 2040 of the central portion 2032 to facilitate attachment of the suspending means 2020 to the soft tissue anchor 2030.

The suspending means 2030 may be respectively attached to the soft tissue anchor 2030 at this recessed point 2044 by crimping a tube around the suspending means 2020 to fix the suspending means 2020 to the soft tissue anchor 2030.

In the embodiment shown the soft tissue anchor may be suitably positioned in the rectus sheath 20120 using an introducing tool 2050. As shown in FIG. 55 the tool 2050 comprises a handle 2052 and elongate body 2054. The elongate body 2054 is curved through an angle of approximately 30° to facilitate positioning of the soft tissue anchor 2030 in the rectus sheath or surrounding soft tissue of the human body from an incision in the upper wall of the vagina (as described below). The soft tissue anchor 2030 is located on the elongate body at a narrowed portion 2058 of the introducing tool such that the soft tissue anchor is held in place by an abutment 2056 such that the narrowed portion 2058 may extend through the hollow portion 2048 of the soft tissue anchor 2030 such that the point 2060 of the insertion tool 2050 protrudes from the first end 2038 of the soft tissue anchor and allows the soft tissue anchor to be inserted into the human body through the soft tissues and more specifically through the rectus sheath 20120 during the placement of the soft tissue anchor.

The placement of the soft tissue anchor 2030 on the insertion tool 2050 is shown in FIGS. 48B and 48C, which shows the soft tissue anchor 2030 being pushed through soft tissue fascia, such as the rectus sheath 20120. Once the soft tissue anchor has penetrated the rectus sheath fascia 20120, as shown in FIG. 48B, the introducing tool 2050 can be withdrawn, as shown in FIG. 48C, leaving the soft tissue anchor 2030 in place.

As shown in FIG. 49 the soft tissue anchor may alternatively be comprised of a central portion 2070 and a plurality of projections 2072 the projections extending radially from the central portion 2070 and arranged along a substantial portion of the length of the central portion 2070. The projections 2072 may be of any shape such that they provide resistance within the fibro-fatty soft tissue and blood tissues of the para-urethral tunnel in the direction opposite to that in which the soft tissue anchor is introduced.

This resistance is also provided by the multiple layers, typically between 5-10 layers of projections 2072 which extend from the central portion 2070.

Using these multiple layers of projections 2072 it is not necessary to insert the soft tissue anchor through the rectus sheath 20120. Instead the soft tissue anchor should be positioned as high in the retropubic space as possible in the fibro-fatty soft tissue.

In the embodiment of the soft tissue anchor comprising multiple layers of projections 2072 which resembles a Christmas tree, as shown in FIG. 50, the introducing tool comprises a collar which releasably retains the projections during insertion into the retropubic space. The collar may comprise a semi-sharp bevelled needle. Following insertion of the Christmas tree like anchor into the fibro-fatty soft tissue of the retropubic space the introducing tool is withdrawn removing the collar from around the plurality of projections 2072 of the soft tissue anchor, which due to their memory expand outwards from the central portion 2070 and grip the fibro-fatty soft tissue of the retropubic space at multiple layers. The collar of the introducing tool which extends around the soft tissue may contain a cross-sectional opening such that once the tool is withdrawn the collar may be removed from the surgical implant by passing the implant through the cross-sectional opening.

Accordingly the invention also provides an introducing tool for use in inserting the soft tissue anchor.

Suspending means 2020 attached to the soft tissue anchors are formed from a strip of plastics material such as polypropylene which is sufficiently soft to avoid damaging the urethra or surrounding body tissue and suitably inert such that it can be left in the human body for a long period of time without causing adverse reactions. Again, other suitable materials will be apparent to those skilled in the art.

The polypropylene mesh strip of 3-5 mm in width which forms the suspending means 2020 has smooth edges to avoid adhesion of the soft tissue to the strip, reducing problems associated with leaving foreign material in the human body for long periods of time. As shown in FIG. 56 the polypropylene mesh strip further comprises pores or pits 2080 ranging in width across the surface of the strip from 50 µm to 200 µm, which extend through the strip from a first surface of the strip 2026 to a second opposite surface 2028 of the strip the pores 2080 allowing tissue in-growth to secure the suspending means 2020 in the body.

The pores 2080 are created by post synthesis treatment of the polypropylene mesh material by a laser.

The polypropylene mesh which forms the suspending means 2020 also comprises microgrooves 2082 of width 5 µm and of depth 5 µm on the surfaces of the polypropylene mesh.

The microgrooves 2082 are aligned such that they are substantially parallel with each other and separated by ridges of around 5 µm in width.

The ridges are formed by square pillars the base of the microgroove being substantially perpendicular to the square pillars or bevelled in relation to the pillars. The microgrooving 2082 being present on both surfaces of the suspending means to orientate and align the proliferating fibroblasts on the surface of the plastics material and cause axial alignment of collagen fibres and formation of at least one strong ordered neoligament.

This orientation and alignment of the proliferating cells adding mechanical strength to the tissue which forms around the plastics material such that it is more able to support the urethra.

The suburethral support is not provided with pores, pits or grooves to discourage the formation of peri-urethral adhesions.

Once the soft tissue anchors have been suitably positioned in either the soft tissue of the para-urethral tunnel or through the rectus sheath 20120 the length of the suspending means 2020 can be altered such that the suburethral support 2010 hangs loosely under the urethra.

As shown in FIG. 42 the suspending means 2020 are attached at a first end 2022, 2024 to the sides 2012, 2014 of the suburethral support 2010, which extend on either side of the urethra.

Figure 46B:
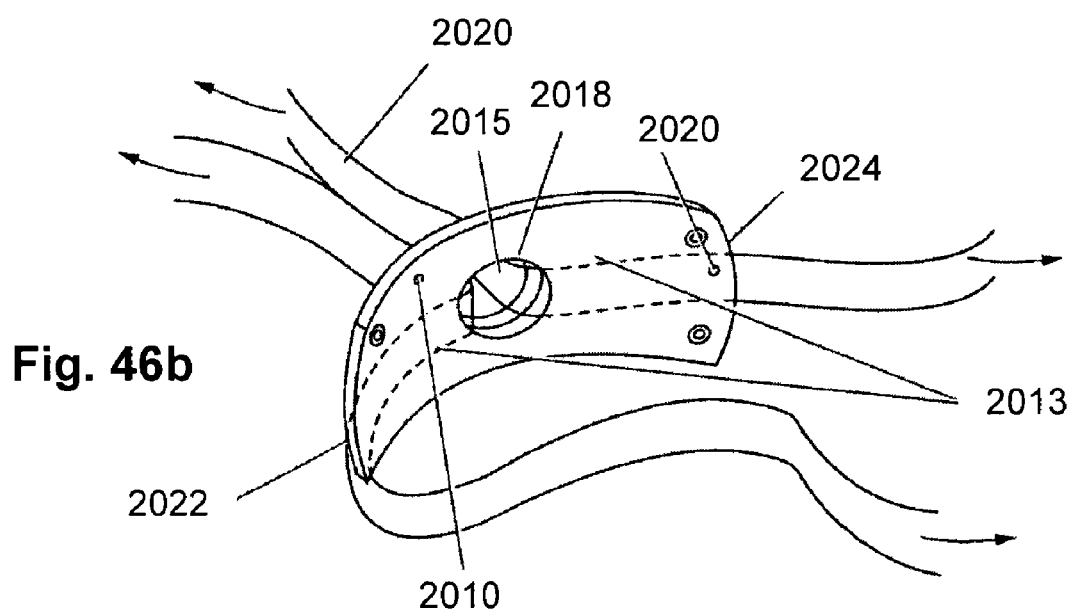
Figure 46C:
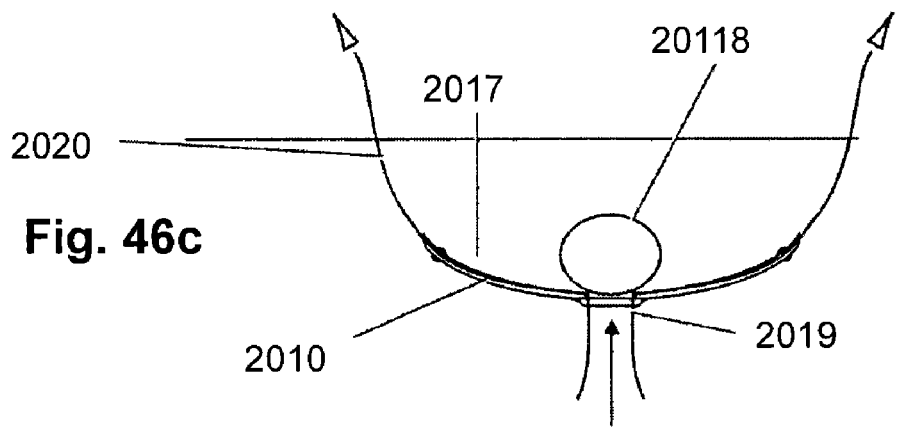

As shown in FIG. 46 a preferred method of altering the length of the suspending means 2020 attached to the suburethral support 2010 comprises a tunnelled element 2013 at each of the free ends 2022, 2024 of the suburethral support 2010 on either side of the urethra. The tunnelled element 2013 extends from the edges of the suburethral support 2010 to an aperture 2015, the aperture being present on the opposite surface 2016 of the suburethral support 2010 to the surface which contacts the urethra 2017, the aperture 2015 having an edge 2018 able to co-operate with a ring element 2019 such that the ring element which has memory can be pushed onto the edge 2018 of the aperture 2015 trapping the suspending means 2020 between the edge of the aperture 2018 and the ring element 2019 thus securing the suburethral support 2010 along a particular desired length of the suspending means 2020 such that the suburethra support 2010 hangs loosely under the urethra.

FIG. 45 shows an alternative method of attaching the suspending means 2020 to the suburethral support 2010, the suspending means 2020 being threaded through jamming slots 2012 such that the suspending means 2020 are permanently attached to the jamming slots 2012 by being pulled into the jamming slots 2012 as shown in FIG. 45 such that the suspending means is held tightly in position.

Alternatively as shown in FIG. 46 the suspending means 2020 may be passed through slots and the suspending means permanently attached to the slots by tying.

In use, as shown in FIG. 52 the soft tissue anchor 2030 is placed on the introducing tool 2050 as described above. An incision 20117 is made in the upper wall 20116 of the vagina, as shown in FIG. 51, and the introducing tool 20112 is passed through the incision 20117, past one side of the urethra 20118, behind the pubic bone 20119 and into the rectus sheath 20120. It is apparent to the surgeon when the rectus sheath 20120 has been penetrated as this stage of insertion presents significant resistance. Once the head 2058 of the introducing tool 2050 and the soft tissue anchor 2030 have passed through the rectus sheath 20120, the resistance diminishes and the surgeon ceases to insert the introducing tool 2050.

The introducing tool 2050 is retracted from the body releasing the soft tissue anchor 2030. Due to the wing sections 2034 on the central portion 2032 of the soft tissue anchor 2030, the soft tissue anchor 2030 is retained by the rectus sheath 20120 as the introducing tool 2050 is retracted. Thus, the suspending means remains in the body, secured by the soft tissue anchor which is opposed by the rectus sheath 20120.

This procedure is repeated, with a second soft tissue anchor 2030 and suspending means 2020, with the introducing tool 2050 being passed through the incision 20117 and past the other side of the urethra 20118. Thus, two suspending means 2020 are provided, attached to the rectus sheath 20120, one passing either side of the urethra 20118.

The suspending means 2020 are passed through the tunnelled elements 2013 of the suburethral support 2010, and the suspending means 2020 are pulled through the aperture 2015 until the suburethral support 2010 is positioned such that it passes under the urethra 20118. The suspending means 2020 are then fixed in place by placing a ring element 2019 over the edge 2018 of the aperture 2015 such that the suspending means are trapped between the edge 2018 and the ring element 2019 securing them in place.

Alternatively as shown in FIG. 45 the suspending means may be fixed in the attachment tabs by threading them through jamming slots 2012 or tying, as described above. The optimal lengths of the suspending means 2020 are such that the suburethral support 2010 passes under the urethra 20118, but exerts no pressure on the urethra 20118 unless the bladder 20121 is displaced. The optimal positioning of the suburethral support 2020 is roughly as illustrated in FIG. 54. When the bladder is displaced, the suburethral support 2010 aids closure of the urethra 20118, thus alleviating urinary incontinence.

In this example, a portion of the surgical implant is impregnated with methylene blue, which is a harmless water soluble dye. At the end of the procedure a small amount of fluid is expelled from the bladder 20121. Should this fluid contain any dissolved methylene blue, it is very likely that the bladder has been perforated on placing the soft tissue anchor 2030. In this case, cystoscopy should be carried out. If no methylene blue is present, the need for cystoscopy is advantageously obviated. Other suitable water-soluble dyes may, of course, be used.

Referring to FIG. 54, it can be appreciated that the surgical implant of the present invention, when inserted in the human body, may extend from the rectus sheath 20120, through the paraurethral space 20130 on one side of the urethra 20118, around the urethra and back to the rectus sheath 20120 on the other side. In contrast, the prior art device comprises a tape 20200 that also extends through the abdominal wall 20127 and represents a far greater implanted mass.

Referring to FIG. 51, in use, the further embodiment of soft tissue anchor illustrated in FIG. 49 for placement in fibro-fatty soft tissue of the retropubic space is placed on an introducing tool. An incision 20117 is made in the upper wall 20116 of the vagina, as shown in FIG. 51, and the introducing tool 20112 is passed through the incision 20117, past one side of the urethra 20118, and located in the fibro-fatty soft tissue and blood vessels of the para-urethral tunnel. In this case the surgeon does not introduce the soft tissue anchor as far into the body as described previously and the rectus sheath 20120 is not penetrated. Once the soft tissue anchor has been suitably positioned in the soft tissue the surgeon ceases to insert the introducing tool and retracts the introducing tool from the body releasing the projections of the soft tissue anchor 2072. The release of the projections 2072 of soft tissue anchor by the introducing tool allows the projections to grip the soft tissue surrounding the soft tissue anchor and provide resistance to movement of the soft tissue anchor in a direction opposite to that which it was inserted.

This procedure is repeated, with a second soft tissue anchor such that the projections 2072 of the soft tissue anchor also provide resistance to movement of the soft tissue anchor in a direction opposite to that which it was inserted the introducing tool being passed through the incision 20117 and past the other side of the urethra 20118.

Thus, two suspending means 2020 are provided, which are held in the soft tissue comprising fibro-fatty tissue and blood vessels.

As described above the suspending means 2020 are passed through the attachment tabs of the suburethral support 2010, and the suburethral support 2010 positioned such that it passes under the urethra 20118.

Again this device contrasts that described by the prior art device in that it does not extend through the abdominal wall 20127 and does not represent as much implanted mass.

Various embodiments of the present invention can be envisaged within the scope of the invention, for example the soft tissue anchor may comprise a cone or a half cone such that a circular or semi-circular base is provided as a retaining means to prevent retraction of the soft tissue anchor in a direction opposite to that in which it is inserted into the tissue.

Alternatively the soft tissue anchor may comprises a substantially flat or disc shaped head. In this case the introducing tool may have a conical head with a sharp point at its apex and a slot for receiving the flat or disc shaped head.

In yet another example, the soft tissue anchor may be formed of two sections. The upper section, i.e. the portion of the anchor that forms the sharp point 2010, may be made from an absorbable material, such as polyglactin such that a sharp point is provided for insertion of the anchor into the body, but this sharp point is later absorbed by the body so as to eliminate any discomfort or disadvantage caused by a sharp pointed object being retained inside the body.

The soft tissue anchor may be made from metal, such as titanium, as this is a hard material that can easily be formed into the head having the sharp point at its apex, and is sufficiently malleable to provide a tube that may be crimped to the suspending means.

I claim:

1. A method for supporting a urethra of a patient, the method comprising:
    making an incision on an upper wall of a vagina of the patient;
    inserting a first end of a surgical implant through the incision and on a first side of a urethra of the patient, the first end including a first fixing zone formed of a plurality of fiber entanglements located along a substantial portion of a length of the first fixing zone and a mesh, at least a portion of the first fixing zone being absorbable, and each fiber entanglement of the first fixing zone forming an enlarged mass of fiber defining an outer surface adapted to anchor the first fixing zone in soft tissue of the pelvis;

anchoring the first fixing zone in soft tissue of a pelvis, without penetrating a rectus sheath, by inserting the first fixing zone in soft tissue of the pelvis such that the first fixing zone is anchored in soft tissue of the pelvis through fiber entanglement anchoring upon insertion of the first fixing zone in soft tissue of the pelvis without using an additional anchoring mechanism;

inserting a second end of the surgical implant through the incision and on a second side of the urethra such that a supporting zone of the surgical implant is located beneath the urethra, the second end including a second fixing zone formed of a plurality of fiber entanglements located along a substantial portion of a length of the second fixing zone and a mesh, at least a portion of the second fixing zone being absorbable, each fiber entanglement of the second fixing zone forming an enlarged mass of fiber defining an outer surface adapted to anchor the second fixing zone in soft tissue of the pelvis, and the supporting zone of the surgical implant being formed of a mesh and being interposed between the first and second fixing zones; and anchoring the second fixing zone in soft tissue of the pelvis without penetrating the rectus sheath, by inserting the second fixing zone in soft tissue of the pelvis such that the second fixing zone is anchored in soft tissue of the pelvis through fiber entanglement anchoring upon insertion of the second fixing zone in soft tissue of the pelvis without using an additional anchoring mechanism, the first and second fixing zones being anchored such that the supporting zone passes under the urethra.

2. The method of claim 1, further comprising anchoring the first and second fixing zones in a retropubic space.

3. The method of claim 1, further comprising anchoring the first and second fixing zones such that the supporting zone passes under a mid-urethra.

4. The method of claim 1, further comprising anchoring the first and second fixing zones in soft tissues of the pelvis such that the surgical implant resists a force of dislodgement of up to 5 N.

5. The method of claim 1, further comprising anchoring the first and second fixing zones in soft tissues of the pelvis such that the surgical implant resists a force of dislodgement of up to 10 N.

6. The method of claim 1, wherein the surgical implant being inserted has a length from 8 cm to 20 cm.

7. The method of claim 1, wherein each of the first and second fixing zones of the surgical implant being inserted has a length that is at least 1 cm and not greater than 8 cm.

8. The method of claim 1, wherein the mesh material of the supporting zone being passed loosely under the urethra includes strands forming major spaces of 1 mm to 10 mm in size.

9. The method of claim 1, wherein each of the first and second fixing zones being inserted has a pointed end.

10. The method of claim 1, wherein the meshes of the first fixing zone, the second fixing zone, and the supporting zone of the surgical implant being inserted are integral.

11. The method of claim 1, wherein inserting the first end of the surgical implant through the incision and on the first side of the urethra of the patient includes inserting a first edge of the first fixing zone and a second edge of the first fixing zone through the incision and on the first side of the urethra of the patient, wherein the first edge and the second edge are tapered toward one another.

12. A method for supporting a urethra of a patient, the method comprising:

making an incision on an upper wall of a vagina of the patient;

inserting a first end of a surgical implant through the incision and on a first side of a urethra of the patient, the first end including a first fixing zone formed of a plurality of fiber entanglements located along a substantial portion of a length of the first fixing zone and a mesh, at least a portion of the first fixing zone being absorbable, and each fiber entanglement of the first fixing zone forming a disorganized mass of fiber defining an outer surface adapted to anchor the first fixing zone in soft tissue of the pelvis;

anchoring the first fixing zone in soft tissue of a pelvis, without penetrating a rectus sheath, by inserting the first fixing zone in soft tissue of the pelvis such that the first fixing zone is anchored in soft tissue of the pelvis through fiber entanglement anchoring upon insertion of the first fixing zone in soft tissue of the pelvis without using an additional anchoring mechanism;

inserting a second end of the surgical implant through the incision and on a second side of the urethra such that a supporting zone of the surgical implant is located beneath the urethra, the second end including a second fixing zone formed of a plurality of fiber entanglements located along a substantial portion of a length of the second fixing zone and a mesh, at least a portion of the second fixing zone being absorbable, each fiber entanglement of the second fixing zone forming a disorganized mass of fiber defining an outer surface adapted to anchor the second fixing zone in soft tissue of the pelvis, and the supporting zone of the surgical implant being formed of a mesh and being interposed between the first and second fixing zones; and anchoring the second fixing zone in soft tissue of the pelvis without penetrating the rectus sheath, by inserting the second fixing zone in soft tissue of the pelvis such that the second fixing zone is anchored in soft tissue of the pelvis through fiber entanglement anchoring upon insertion of the second fixing zone in soft tissue of the pelvis without using an additional anchoring mechanism, the first and second fixing zones being anchored such that the supporting zone passes under the urethra.

* * * * *